(12) United States Patent
Eng et al.

(10) Patent No.: US 10,967,035 B1
(45) Date of Patent: Apr. 6, 2021

(54) AQUACULTURE FEED ADDITIVE

(71) Applicant: HP Ingredients Corp., Bradenton, FL (US)

(72) Inventors: Annie Eng, Bradenton, FL (US); Juan O. Hancke, Valdivia (CL)

(73) Assignee: HP Ingredients Corp., Bradenton, FL (US)

( * ) Notice: Subject to any disclaimer, the term of this patent is extended or adjusted under 35 U.S.C. 154(b) by 0 days.

(21) Appl. No.: 16/992,168

(22) Filed: Aug. 13, 2020

Related U.S. Application Data

(60) Provisional application No. 62/975,255, filed on Feb. 12, 2020.

(51) Int. Cl.
| | |
|---|---|
| *A61K 36/87* | (2006.01) |
| *A61K 9/00* | (2006.01) |
| *A61K 31/365* | (2006.01) |
| *A61K 36/79* | (2006.01) |
| *A61K 36/02* | (2006.01) |
| *A61K 31/12* | (2006.01) |

(52) U.S. Cl.
CPC ............ *A61K 36/87* (2013.01); *A61K 9/0056* (2013.01); *A61K 31/12* (2013.01); *A61K 31/365* (2013.01); *A61K 36/02* (2013.01); *A61K 36/79* (2013.01)

(58) Field of Classification Search
CPC ...... A61K 36/87; A61K 9/0056; A61K 31/12; A61K 31/365; A61K 36/02; A61K 36/79
See application file for complete search history.

(56) References Cited

U.S. PATENT DOCUMENTS

| | | |
|---|---|---|
| 2012/0189706 A1 | 7/2012 | Copp et al. |
| 2018/0289759 A1 | 10/2018 | Campos et al. |

FOREIGN PATENT DOCUMENTS

| | | |
|---|---|---|
| CN | 1290429 C | 12/2006 |
| CN | 102764308 A | 11/2012 |
| JP | 4398172 B2 | 10/2009 |
| WO | 2006008115 A1 | 1/2006 |

OTHER PUBLICATIONS

Basha, Kusunur Ahamed, "Effect of dietary supplemented and andrographolide on growth, non-specific immune parameters and resistance against Aeromonas hydrophila in Labeo rohita (Hamilton)", Fish & Shellfish Immunology, 2003, p. 1433-1441, V35.
Caipang, Christopher Marlowe A., "Influence of alginic acid and fucoidan on the immune responses of head kidney leukocytes in cod", Fish Physio Biochem, 2011, p. 603-612, V37.
El-Boshy, Mohamed, "Dietary fucoidan enhance the non-specific immune response and disease resistance in African catfish, *Clarias gariepinus*, immunosuppressed by cadmium chloride", Veterinary Immunology and Immunopathology, 2014, p. 168-173, V162.
Hernandez, Adrian J., "The effects of supplemented diets with phytopharmaceutical preparation from herbal and macroalgal origin on disease resistance in rainbow trout against *Piscirickettsia salmonis*", Aquaculture, 2016, p. 109-117, V454.
International Search Report, PCT/CL2016/050015, 2016, p. 1-3.
Kang, So Young, "In vitro Antiviral Activities of Korean Marine Algae Extracts against Fish Pathogenic Infectious Hematopoietic Necrosis Virus and Infectious Pancreatic Necrosis Virus", Food Sci. Biotechnol., 2008, p. 1074-1078, V17, I5.
Rattanachaikunsopon, Pongsak, "Prophylactic effect of *Andrographis paniculata* extracts against *Streptococcus agalactiae* infection in Nile tilapia (*Oreochromis niloticus*)", Journal of Bioscience and Bioengineering, 2009, p. 579-582, V107, I5.
Vatsos, Ioannis N., "Seaweed extracts as antimicrobial agents in aquaculture", J Appl Phycol, 2015, p. 2017-2035, V27.
Yang, Qing, "Effects of dietary fucoidan on the blood constituents, anti-oxidation and innate immunity of juvenile yellow catfish (*Pelteobagrus fulvidraco*)", Fish & Shellfish Immunology, 2014, p. 264-270, V41.

*Primary Examiner* — Aaron J Kosar
(74) *Attorney, Agent, or Firm* — Pharmaceutical Patent Atty's LLC

(57) ABSTRACT

A feed additive suitable for use in commercial aquaculture, made from whole dried seaweed powder supplemented with 2.5 percent (w/w) andrographolide, increases feed conversion ratio (the ratio of weight gain to weight of feed used) and growth rate, while reducing vulnerability to water-borne marine pathogens such as *Piscirickettsia salmonis* and white-spot syndrome virus.

21 Claims, 39 Drawing Sheets
(3 of 39 Drawing Sheet(s) Filed in Color)

AQUACULTURE FEED ADDITIVE

RELATED APPLICATIONS

This application asserts priority from United States provisional patent filing Ser. No. 62/975,255 filed 12 Feb. 2020, the contents of which are here incorporated by reference.

UNITED STATES GOVERNMENT INTEREST

None

THE NAMES OF THE PARTIES TO A JOINT RESEARCH AGREEMENT

Certain of the testing described herein was performed on behalf of the Assignee by the Center for Research in Food and Development, A. C. Mazatlan Unit in Aquaculture and Environmental Management, Mazatlan Mexico, by Fundación Chile, Puerto Montt Chile, and by Aquaim S.p.A., Santiago Chile.

REFERENCE TO A SEQUENCE LISTING

None.

STATEMENT REGARDING PRIOR DISCLOSURES BY THE INVENTOR OR A JOINT INVENTOR

None.

BACKGROUND

In aquaculture, congested growing conditions can both impair the cultured species' immune system and, by physically constraining the fish in a limited space, promote the spread of disease.

Many measures have been taken for controlling or preventing the spread of disease in aquaculture. One approach is adding antibiotics to fish feed. This approach is disfavored because it enables the emergence of antibiotic-resistant bacteria and may leave significant antibiotic residue in the meat of the fish so grown.

An alternative approach is vaccination. Vaccines do not favor the emergence of antibiotic-resistant pathogens, and leave no antibiotic residue in the fish. Vaccines, however, are expensive. Further, injecting individual fish is labor-intense and thus add significant expense. Thus, for smaller species such as prawn, vaccines are cost-prohibitive. Further, vaccination is not effective against some relevant pathogens such as *Piscirickettsia salmonis*, SAV virus, *Francisella noatunensis, Renibacterium salmoninarum*, IPN virus, if the fish is infected before being vaccinated. This is due to the intracellular nature of the pathogens.

An alternative approach is taught by Paula MIRANDA-CAMPOS et al., Veterinary Composition Of Marine Algae And *Andrographis* Sp. Extracts, Which Can Be Used To Treat Infections In Fish, Patent Cooperation Treaty publication No. WO 2016/161534 (available in the English language as counterpart Canada national stage application Serial No. 02981989, filed 2017 Oct. 6). Miranda-Campos teaches a combination of two aqueous plant extracts. The first extract contains at least 5% of fucoids. The second extract contains least 5% of andrographolide. Miranda-Campos teaches that the extract combination that she describes is commercially marketed under the FUTERPENOL® trademark. See pg. 20 line 8. The FUTERPENOL® product, however, does not work particularly well.

To find a more-effective improvement, we thus set about making variations and modifications of the extract combination described in Miranda-Campos. We found that one can produce a far more effective composition by varying the composition taught by Miranda-Campos in three critical ways.

First, Miranda-Campos teaches to make aqueous extracts and eliminate any water-insoluble plant fiber and water-insoluble plant pigments etc. We surprisingly found that replacing Miranda-Campos' fucoid-containing aqueous extract with whole seaweed, dried and powdered and including the insoluble fibrous material, makes a far more effective product.

Without intending to be bound by a theory, our experimental data (discussed in detail below) imply that the insoluble, fibrous plant material provides two functions. First, insoluble, fibrous plant material appears to aid gut motility. This enables a fish infected with gastro-intestinal pathogens to more quickly eliminate pathogens from its gastrointestinal tract.

Second, the insoluble, fibrous plant material appears to aid in the systemic absorption, or "bioavailability," of andrographolide. That is, andrographolide does not to our knowledge naturally occur in fish food sources. We thus posit that the fish gastrointestinal tract has not evolved to absorb andrographolide efficiently. Thus, when one administers andrographolide to a fish, the fish gastrointestinal tract does not absorb that andrographolide efficiently, so it simply passes through the fish without being absorbed systemically. We posit that the concomitant administration of insoluble fiber resolves this and enables the fish gastrointestinal tract to better absorb andrographolide systemically.

Similarly, Miranda-Campos teaches to combine her two aqueous extracts, but to use far less of the fucoid extract than the andrographolide extract. Specifically, Miranda-Campos teaches to use a ratio of 5:95 to 20:80, preferably a ratio of 10:90. See Miranda-Campos pg. 22 lines 6-8. We surprisingly found that one can improve effectiveness by reversing the ratio taught by Miranda-Campos. While Miranda-Campos teaches a ratio of 5:95 to 20:80 and prefers in a ratio of 10:90, we have found that the opposite ratio—about 96:5—significantly improves function. Without intending to be bound by theory, our experimental data imply that our new ratio is important because the gastrointestinal tract of a fish does not readily absorb andrographolide unless a relatively small amount of it is combined with a relatively large amount of insoluble seaweed fiber. Thus, the surfeit of *Andrographis* sp. extract taught by Miranda-Campos is excreted, rather than absorbed.

Third, Miranda-Campos teaches to use any of seventeen different species of *Andrographis* plants. See pg. 16 lines 7-13. In contrast, we posit that the best results are obtained with only one of these species—*A. paniculata*.

We therefore here teach an improved aquaculture feed additive comprising whole seaweed, dried and powdered and including the insoluble fibrous material, combined with andrographolide in a ratio of about 95:5.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

We first describe our in vitro experiments. We then describe comparative in vivo experiments.

Example 1

Our goal in Example 1 was to assess the effect of our modified composition on the expression and activity of IL-12 and type I interferon in SHK-1 cells.

Materials & Methods

The SHK-1 cell line was established from primary cultures of adherent cells from Atlantic salmon head kidney. The cells have been used in the study of the infectious salmon anemia (ISA) virus. SHK-1 cells are recognized by monoclonal antibodies that are specific for Atlantic salmon peripheral blood leucocytes. In contrast, SHK-1 cells are not recognized by monoclonal antibodies specific to polymorphonuclear leucocytes. SHK-1 cells have been shown to phagocytose the fish pathogen *Aeromonas salmonicidia* to some extent, but no bactericidal activity was observed over a period of 72 hours. From these results it has been concluded that SHK-1 cells are derived from leucocytes, yet have some of the properties of macrophages. Studies have shown that the cells can be passaged more than 60 times.

FUTERPENOL™ fish feed additive, commercially available from MNL Group, is labeled as having a composition as described in Paula MIRANDA-CAMPOS et al., Veterinary Composition Of Marine Algae And *Andrographis* Sp. Extracts, Which Can Be Used To Treat Infections In Fish, Patent Cooperation Treaty publication No. WO 2016/161534, and is labeled for use at 1 kg per ton of commercial feed.

OCEANFEED™ dried powdered mixed seaweed having 4-9% (w/w) crude fiber and 30-45% crude ash is commercially available from Ocean Harvest Technology Inc., Milltown Ireland.

PARACTIN® andrographolide 50% (w/w) is commercially available from HP Ingredients Inc., Bradenton Fla. USA.

Andrapholide 99% ("AP") and poly I:C are commercially available from Millipore-Sigma, St. Louis Mo. USA.

ZYMOSAN™ glucan is commercially available from InvivoGen Inc., San Diego Calif. USA.

We combined OCEANFEED™ and PARACTIN® in a 95:5 ratio (w/w) to make a treatment combination. In the accompanying figures, this test or "non-control" treatment is sometimes denoted "NC" or "NatC". We then dissolved NC in a stock solution of dimethyl sulphoxide (DMSO). Different dilutions were then prepared in culture L-15, to create dilutions providing andrographolide doses of 5 nM and 10 nM.

We plated wells with SHK-1 cells in monolayer. We then exposed the plates variously to one of our DMSO solutions, andrographolide 99%, poly I:C and commercial glucans, and incubated the plates for 2, 4, 6, 12 and 48 hrs. We then trypsinized the cells to detach the cells from the plates, harvested the cells, extracted the total RNA and assayed the RNA using real-time PCR (RT-PCR) according to standardized protocols from the Aquatic Organisms Biotechnology Lab of the Universidad Austral de Chile with probes for IL-12 and type I interferon.

Results

Figure 1:
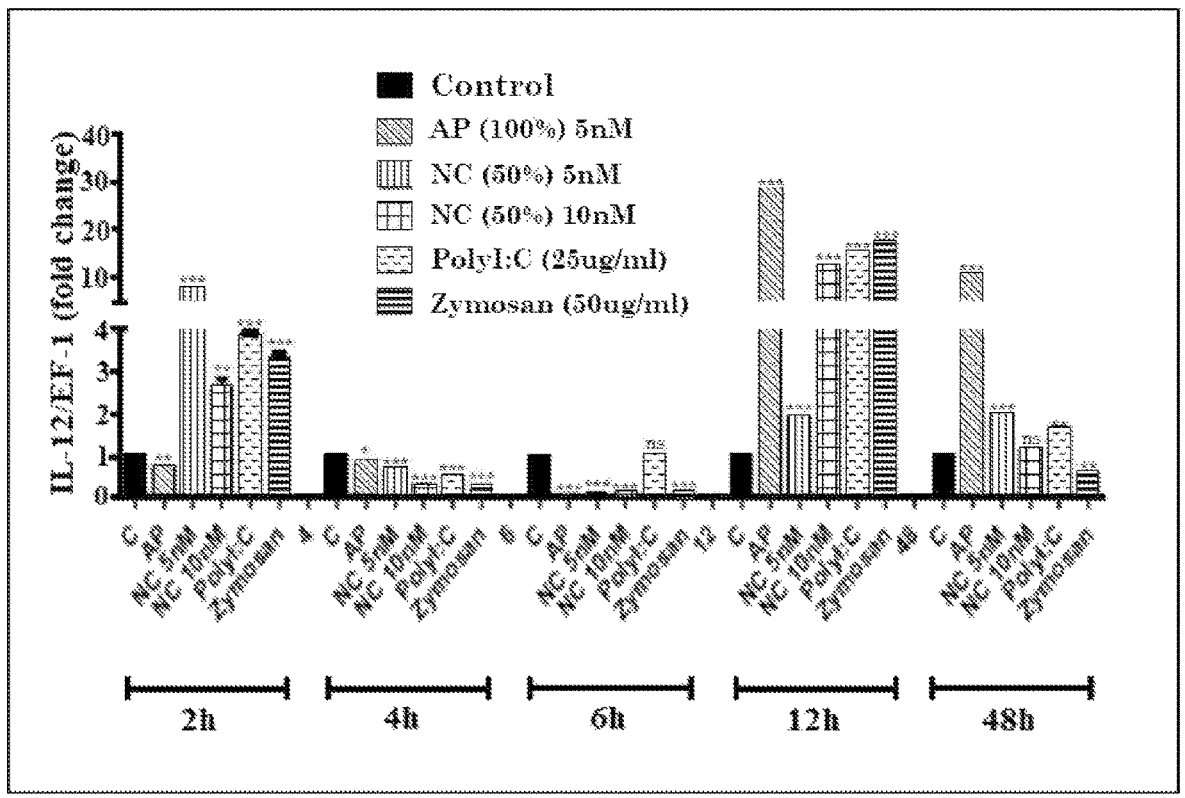
FIG. 1 measures IL-12/EF-1 mRNA expression over time in vitro in SHK-1 cell cultures exposed to andrographolide 99% Active Pharmaceutical Ingredient ("API" or "AP"), poly I:C, ZYMOSAN™ brand glucan, and the claimed non-control ("NC") test combination in several concentrations.

The effect of treatment on IL-12 mRNA transcription is shown in FIG. 1. At 0 hours, IL-12 mRNA levels remained in the range of 1 for each treatment, as a base-line expression. (data not shown) At 2 hours, for both evaluated doses of our DMSO solution (5 nM and 10 nM), we observed heightened IL-12 mRNA levels. By 4 and 6 hours, IL-12 mRNA levels returned to below the base-line level. Surprisingly, the highest expression of IL-12 mRNA was achieved at 12 hours after treatment. At 12 hours, the dose of 10 nM NC produced mRNA expression 10-fold greater than the control sample. At 48 hrs after stimulation, the level of IL-12 mRNA expression tended to decrease.

Interferon mRNA expression at time=0 was in the range of 1 for all treatment groups (data not shown). At 2 hours, the early stimulation of the molecular marker is presented for both doses of NC (5 nM and 10 nM). At 4 and 6 hours no differences were observed with the control sample, except for the NC 5 nM dose. The highest expression of this marker was observed at 12 hrs, with 10 nM NC causing a 4-fold increase in the expression compared to negative control samples. In general, levels of IFN expression for all treatment groups tended to decrease by 48 hrs.

Conclusion

NC caused a 10-fold increase in IL-12 expression and 4-fold increase in IFN-1 expression compared to negative controls, at a dose of 10 nM and 12 h of exposure in SHK-1 cells.

Example 2

Our goal for this experiment was a dose-finding study designed to assess the MIC of our NC preparation in in vitro cultures of *P. salmonis*, comparing five (5) different doses of NC.

Materials & Methods:

All experiments were performed in Austral-SRS broth medium. For the analysis, *Piscirickettsia salmonis* strain type LF-89 was used in order to analyze the effect of treatment on inhibiting bacterial growth. Bacterial growth was measured using optical density according to the protocol described by Yañez et al. (2014).

As a positive control for growth inhibition, we used LF-89 with florfenicol antibiotic. Likewise, *E. coli* was used as another positive control of the vehicle were the natural compound was dissolved, in this case DMSO. Also, a positive control of growth without the compound nor the antibiotic was used The dilutions of NC and andragrapholide (AP) were 500, 250, 125, 62.5, 31.25, 15.6, 7.8, 3.9, 1.95 and 0.98 g/ml.

Figure 3:
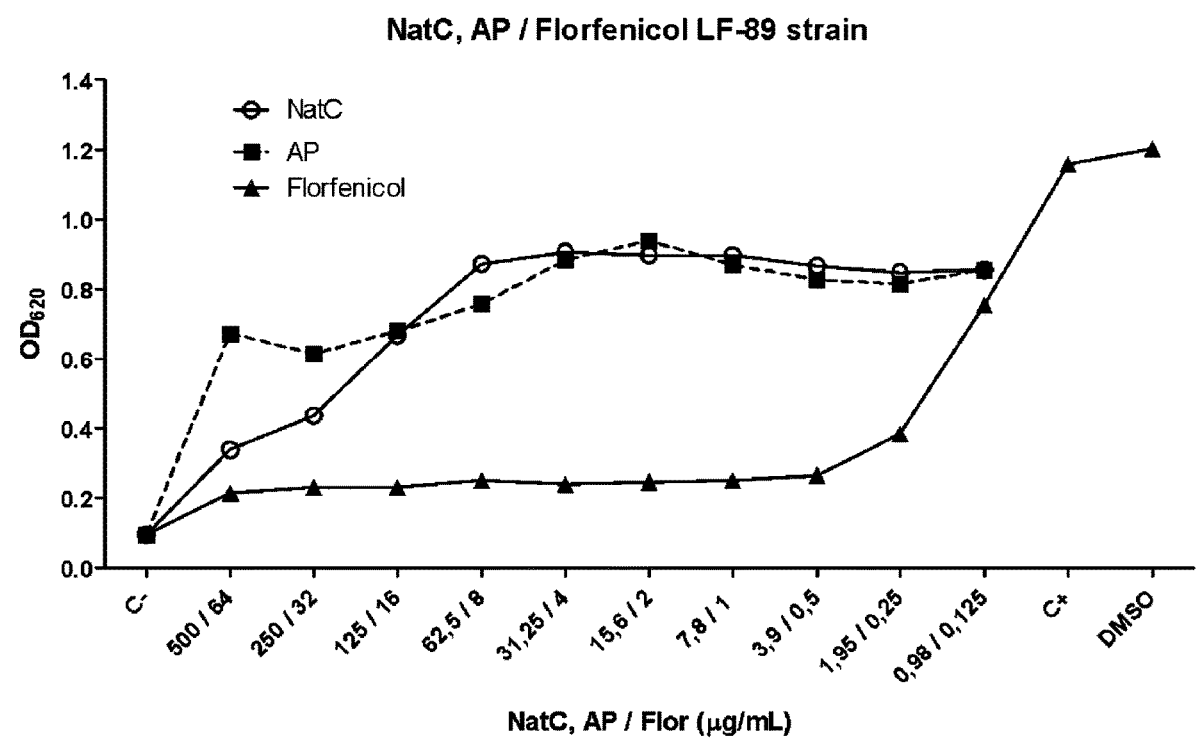
FIG. 3 measures bacterial growth measured using optical density according to the protocol described by Yañez et al. (2014), for *Piscirickettsia salmonis* strain type LF-89, in cultures treated with florfenicol, andrographolide 99% ("AP") and the subject (non-control) composition ("NC" or "NatC").

Results:

FIG. 3 shows that NC had an inhibitory effect on bacterial growth using concentrations of 250 µg/ml. Likewise, a 1.4-fold inhibition of bacterial growth was observed at 500 µg/ml. In the case of AP, no significant differences in the inhibitory effect was observed at the analyzed concentrations. In the case of florenicol, the concentrations of 64, 32 and 16 µg/mL present a 5-fold mean inhibition in bacterial growth.

Figure 4:
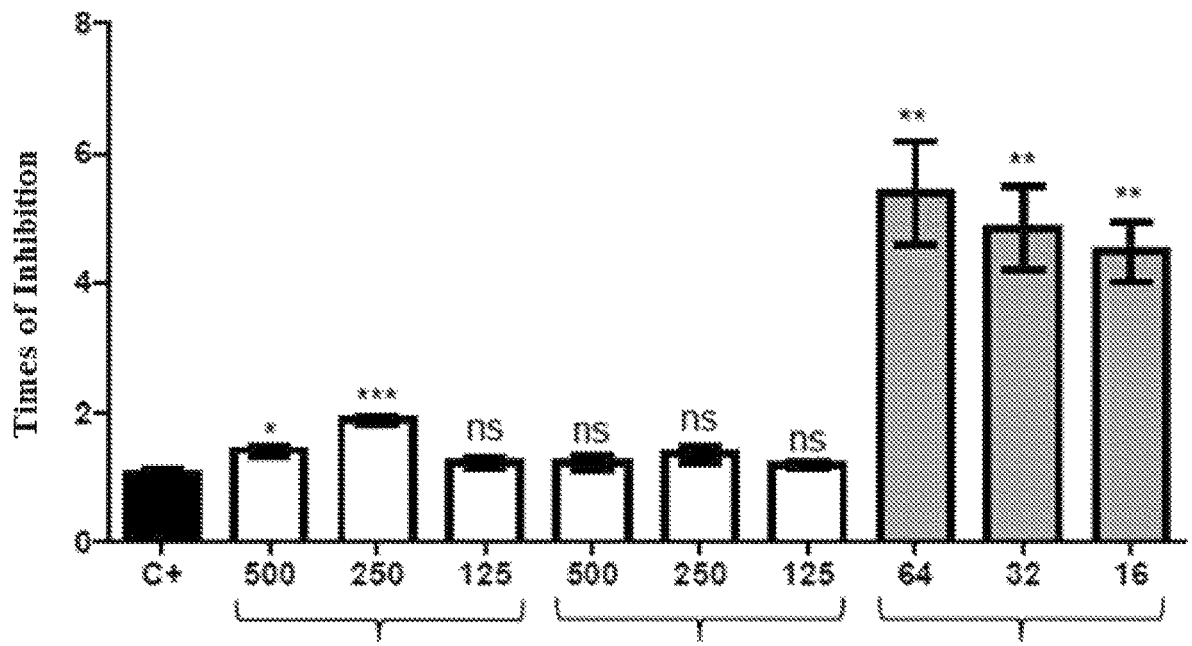
FIG. 4 quantifies and compares bacterial growth inhibition for *Piscirickettsia salmonis* strain type LF-89, in cultures treated with florfenicol, andrographolide 99% ("AP") and the subject (non-control) composition ("NC"). Column 1=control; columns 2-4=NC; columns 5-7=AP; columns 8-10=florfenicol.

FIG. 4 shows the relative effect of NC, AP and Florfenicol on the growth of *P. salmonis*. FIG. 4 column (A) measures the bacterium cultured in Austral-SRS medium, bacterial growth derived from optical density measured by spectrophotometer at 620 nm. Column (B) shows the relative analysis of bacterial growth inhibition of the analyzed compounds. C−, control sample culture, C+, *P. salmonis*, DMSO, control vehicle. The asterisks show significant differences compared to the control vehicle (DMSO) using t-student (*P<0.05, P<0.01 y*P<0.001).

Example 3

The goal of this experiment was to assess the effect of our test (not control, or "NC"/"NatC") composition in vivo in a rainbow trout marine facility, located in Chiloé, Chile, on molecular marker IL-12 and CD8+, compared to AP, for a treatment pulse of 15 days.

Materials & Methods:

We compared several aquaculture diets suitable for use in commercial aquaculture. The standard diet was fishmeal commercially available from Salmones Antartica S.A., Los Angeles, Chile. A second diet was the standard diet supplemented by AP (1 kg/ton of feed). A third diet was the standard diet supplemented by our test (non-control or "NC"/"NatC") preparation at the amount of 0.5 kg/ton of feed.

Fish were segregated into nine separate cages, 55,000 fish per cage, with fish having an average weight of 600 grams at t=0. Each diet was administered to each of three (3) cages for 15 days.

At day 15, anterior kidney samples were taken from three (3) fish from each cage. We extracted total RNA from each sample, and then quantified the expression of IL-12 and $CD8^+$ using real-time quantitative PCR, according to the standardized protocols of the Aquatic Organisms Biotechnology Lab of the Universidad Austral de Chile.

Figure 5:
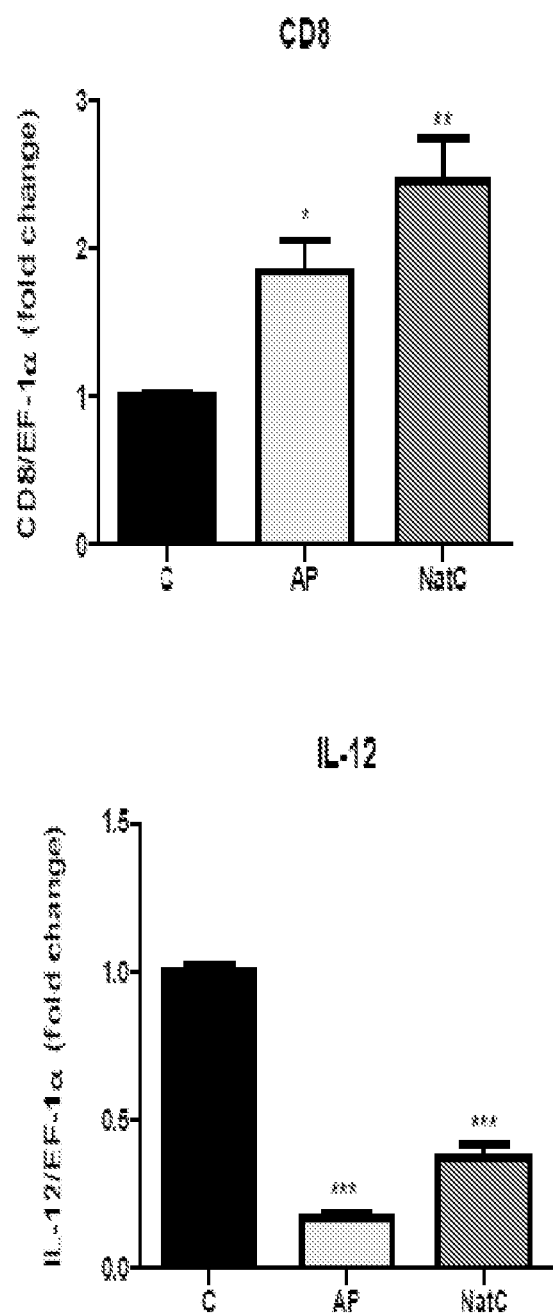
FIG. 5 shows the analysis of RT-qPCR for IL-12 and CD8+ expression in anterior kidney of fish treated with C, AP and NC "NatC") in all sampled cages.

Results:

Our results are shown in FIG. 5. FIG. 5 shows the analysis of RT-qPCR for IL-12 and CD8+ expression in anterior kidney of fish treated with NC and AP in all sampled cages. The control samples correspond to the results from trout fed the control diet ("C").

Our data show that both NC and AP increase the expression of CD8+ as compared to the control group, but NC increases CD8 expression significantly more than does AP.

Similarly, both NC and AP depress the expression of IL-12 as compared to the control group, and the difference is significant. FIG. 5 shows the ±standard error for the three individuals taken from each treatment group. Asterisks indicate differences compared to the control sample that are statistically significant using the Student's t-test (*=p<0.05; =p<0.01 and *=p<0.001).

Conclusions $CD8^+$ expression up-regulates cell-mediated immunity. The higher expression of this marker is associated with a greater presence of cytotoxic T lymphocytes, which are required for the elimination of intracellular pathogens.

Our data show that both NC and AP stimulate $CD8^+$ expression in anterior kidney of rainbow trout compared to control, and the increase in expression compared to control is significant. NC, however, produces an increase in expression significantly greater than does AP. These data indicate that both NC and AP offer a protective effect against an infective challenge with *P. salmonis*, but NC is surprisingly more effective than AP.

The importance of IL-12 in provoking a harmful Th1-like auto-immune response in fish, have been recently described using the rainbow trout model (Wang et al. 2014). This damaging auto-immune mechanism, activated mainly by IL-12, orients the generation of a Th1-type response (Hamza et al, 2010; Pearce, 2017).

Our data indicate that both AP and NC suppress IL-12 expression, and the difference from control is significant. This is advantageous in the absence of infection because in the absence of infection, IL-12 expression may provoke a harmful auto-immune reaction.

NC inhibits the growth of the *P. salmonis* agent in culture medium. See Examples 1 and 2, above. Under commercial in vivo fish farming production conditions, we expect a lower infection pressure in fish that are fed diets supplemented with this additive.

The NC combination of ~4% (w/w) andragrapholide and ~95% dried powdered whole seaweed improves feed uptake by fish and, at the same time, shifts the immune response to one mediated by cells (Th1), shown to be efficient in the elimination of intracellular pathogens such as *P. salmonis*.

NC inhibits growth of *P. Salmonis* in culture conditions, as shown in Examples 1 and 2 above. In this in vivo pilot test, when compared to control NC showed more stimulation of the immune activity markers (2.5, $p<0.05$) than did AP (2.0, $p<0.01$).

Example 4

The aim of this study is to quantify the in vitro immune-stimulant properties of NC using SHK-1 cells.
Materials & Methods:

The expression of innate immunity marker was assessed in relation to the activation of anti-bacterial and anti-viral immune mechanisms. We also quantified the protecting effect of the NC formulation in the same type of cells in an in vitro challenge with *P. salmonis* and infectious pancreatic necrosis virus (IPNv).

Finally, the effects of treatment were analyzed on the growth inhibition of *P. salmonis* through minimum inhibitory concentration assays. In the case of the immunity markers analyzed, these corresponded to IL-12 and IFN-I. The expression of the mRNA of these markers have been analyzed both in vitro and in vivo, showing changes in their expression as an effect of fish bacterial and viral molecules.

We assessed the cell protection effect of NC in cells treated for 6 h (time with the highest expression of inter-leukins with a dose of 5 nM of NC) and a later challenge with *P. salmonis* at $1\times10^4$ bacteria/mL. We quantified the cell protection effect by measuring the liberation of lactate dehydrogenase enzyme (LDH) for 9 days.

We also assessed the cell protection effect of NC in cells treated for 6 h, (time with the highest expression of inter-leukins with a dose of 5 nM of NC) and later challenge with infectious pancreatic necrosis virus (IPNv) at a MOI of 0.1 infectious viral particles/cell. We again measured the cell protection effect by measuring the liberation of Lactate dehydrogenase enzyme (LDH) for 9 days.

Our evaluation consisted in assessing the in vitro effect of NC and AP on the capacity of *P. salmonis* to generate a cytopathic effect (cellular lysis), quantified by measuring the amount of free LDH in the culture medium. In this case, and according to the previous description, a pre-challenge of 6 hours treatment with NC and AP (5 nM) was chosen. Afterwards, the cells were infected with $10^2$ and $10^3$ total bacteria in 1 mL of culture medium for each plate.
Results:

In the case of *P. salmonis*, a protector effect was detected on the cells pre-treated with NC for 6 hours until day 20 post-infection, when the cells were infected with $10^2$ and $10^3$ bacteria (FIG. 1).

Worth mention is the fact that the cells treated with NC showed no cell death at the beginning of the experiment. This could be explained by an apparent cellular protecting effect of NC on cellular viability.

Figure 6:
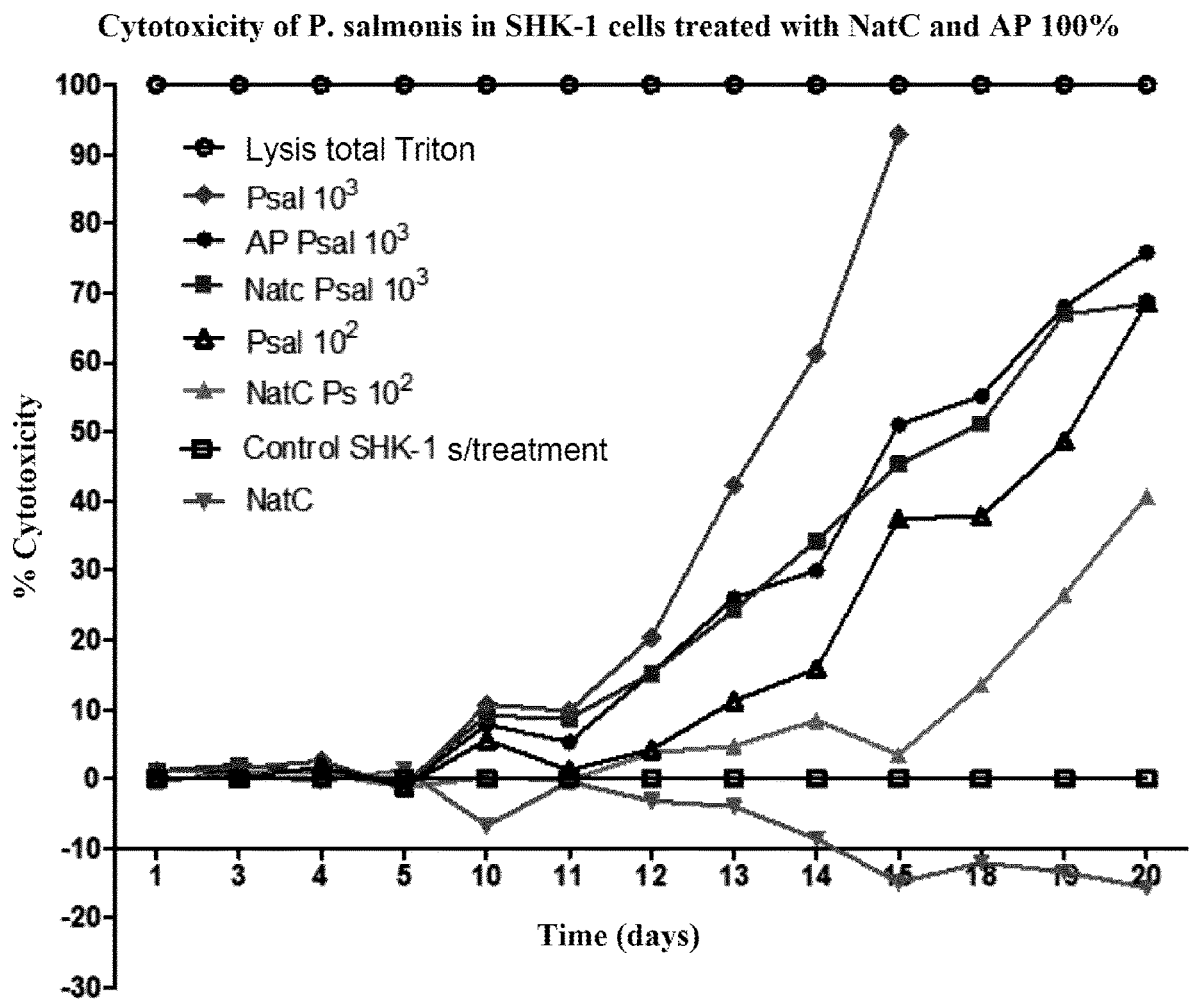
FIG. 6 shows results for a cytotoxicity analysis of SHK-1 cells treated with different treatments, and then exposed to *P. salmonis*. "NatC Psal $10^2$" and "NatC Psal $10^3$": cells treated with NC 5 nM and exposed to *P. salmonis* $10^2$ and $10^3$ bacteria/mL respectively. "AP Psal $10^3$": SHK-1 cells treated with andrographolide 5 nM (1.75 ng/mL) and exposed to *P. salmonis* $10^3$ bacteria/mL. "Psal $10^2$" and "Psal $10^3$" SHK-1 cells exposed to *P. salmonis* $10^2$ and $10^3$ bacteria/mL respectively. "NatC": NC 5 nM (3.5 ng/mL).

FIG. 6 shows results for a cytotoxicity analysis of SHK-1 cells treated with different treatments, and then exposed to *P. salmonis*. NatC+Psal $10^2$ and NatC+P.sal $10^3$: cells treated with NC 5 nM and exposed to *P. salmonis* $10^2$ and $10^3$ bacteria/mL respectively; AP Psal $10^3$, SHK-1: cells treated with andrographolide 100%, 5 nM (1.75 ng/mL) and exposed to *P. salmonis* $10^3$ bacteria/mL; Psal $10^2$ and Psal $10^3$: SHK-1 cells exposed to *P. salmonis* $10^2$ and $10^3$ bacteria/mL respectively; NatC: NC 50%, 5 nM (3.5 ng/mL).

Figure 2:
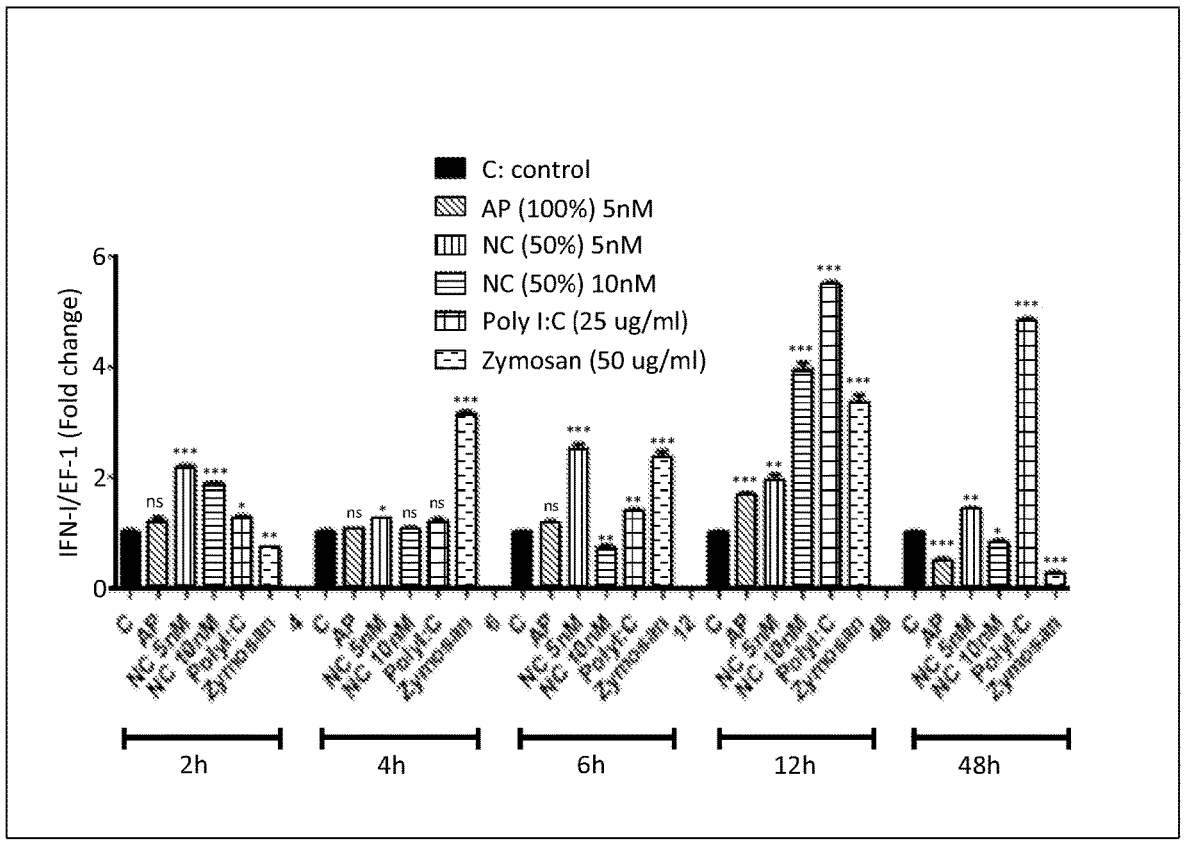
FIG. 2 measures type I interferon mRNA expression over time in vitro in SHK-1 cell cultures exposed to andrographolide 99% ("AP"), poly I:C, ZYMOSAN™ glucan and the claimed non-control ("NC") composition in two concentrations.

In the case of IPN virus, a protective effect could be observed on the lysis in SHK-1 cells pre-treated for 6 h with NC (5 nM) from 5 to 9 days post-infection. NC pre-treatment was associated with less cytotoxicity (FIG. 2), showing a difference from day 5 post-infection, which difference was sustained until day 9.

Figure 7:
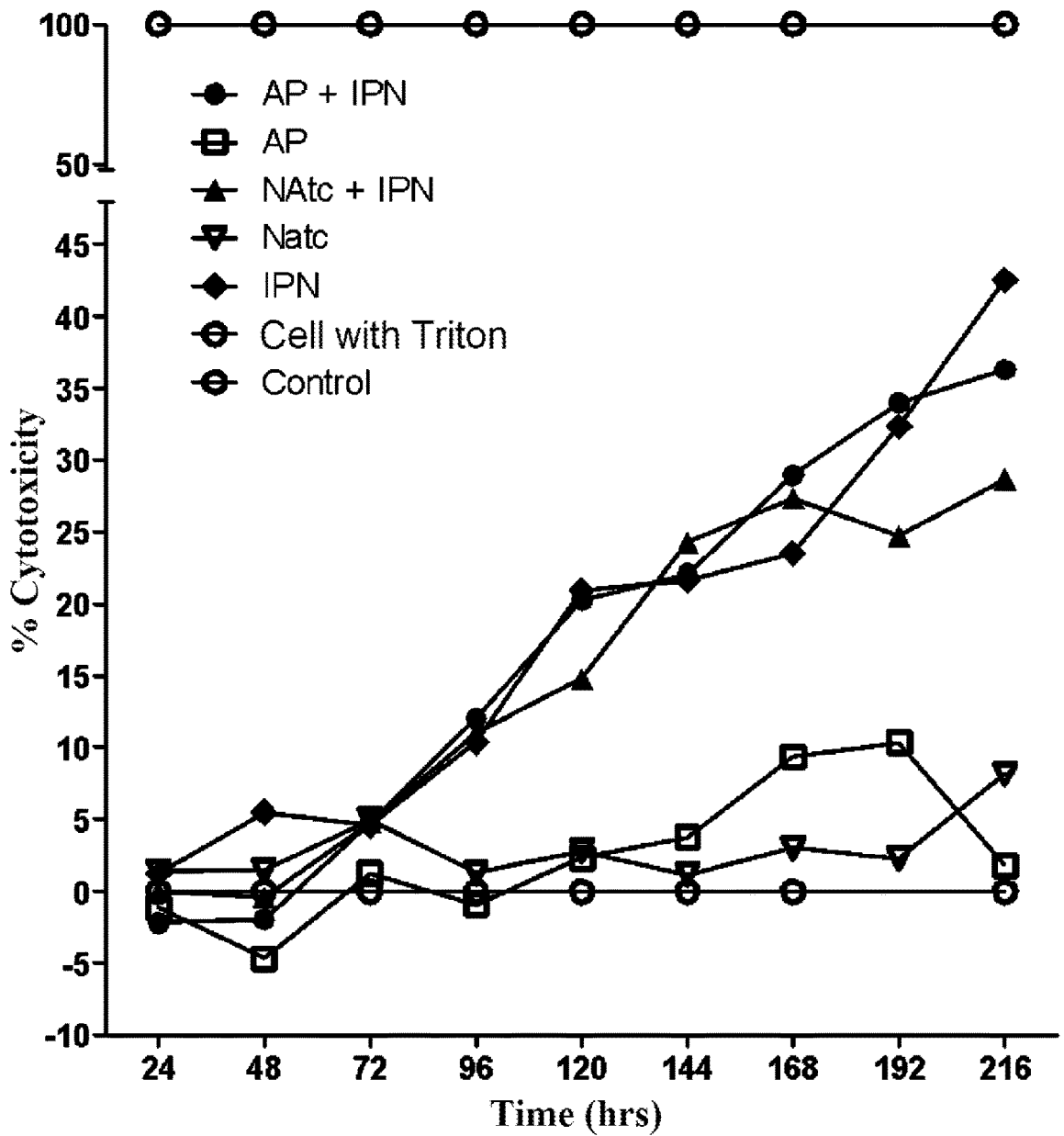
FIG. 7 plots the results of a cytotoxicity analysis of SHK-1 cells treated with different interventions and then exposed to IPNv.

FIG. 7 plots the results of a cytotoxicity analysis of SHK-1 cells treated with different interventions and then exposed to IPNv. Key: AP: Andrographolide 100%, 5 nM (1.75 ng/mL); AP+IPNv: Andrographolide 5 nM and IPNv (100 TCID); NatC: NC 50%, 5 nM (3.5 ng/mL); NatC+IPNv: NC 5 nM and IPNv (100 TCID); IPNv: SHK-1 cells infected with IPNv Conclusions Pre-treatment with NC protects SHK-1 cells against a single challenge with *P. salmonis*, showing a Relative Percent Survival (RPS, a relative survival rate) of 87.5% with $10^2$ $LD_{50}$ (lethal dose for 50% of cells) at 15 days and a RPS of 50% with $10^3$ $LD_{50}$ at 15 days.

Pre-treatment with NC protects SHK-1 cells against a single challenge with IPNv (Pancreatic Necrosis Virus), with a RPS of 45% at 9 days post challenge.

Example 5

The shrimp industry, particularly the industrial farming of white shrimp (*Litopenaeus vannamei*), has intensified in recent years, providing many countries with great economic and social benefits. At the time there have been great challenges, including the emergence of diseases such as white spot syndrome virus (WSSV). These diseases, when occurring in densely-populated industrial farms, have led to high mortality both for post larvae and juvenile shrimp in a few days. This has caused the collapse of production in some of the world's leading shrimp-producing countries.

WSSV has been detected in several shrimp species such as *P. monodon*, *P. japonicus*, *P. chinensis*, *P. indicus*, *P. merguiensis*, *P. setiferus*, *L. stylirostris*, *L. vannamei*, *P. stylirostris*, *P. aztecus*, *P. duorarum*. Infection is associated with stress and low temperatures (<27°), as well as factors typical of the development of the disease itself. Infected shrimp have also been shown to be asymptomatic carriers, which poses the greatest risk of worldwide contagion. Clinical signs when the disease develops are empty intestinal tract, anorexia, erratic swim lethargy, reddish coloration, and often the presence of white spots on the cuticle, among others. Cumulative mortality of 100% have been observed in the first 10 days after the first signs appear. This represents a great challenge that must be thoroughly researched and documented in order to eradicate or control it.

Histology represents the best way to do WSSV detection and be confirmed by PCR. With the optimization of cultivation systems and techniques, various products have emerged with the intention of optimizing processes, controlling disease incidence, promoting growth and increasing survival.

It is recommended to use adequate diets, avoid sudden changes in salinity and temperature, do not exceed recommended densities and handle a correct acclimatization, lengthening times before planting. Currently there is a wide variety of probiotics, prebiotics, immunostimulants, vitamin mixtures, mixtures of fatty acids and amino acid, among other products that are available on the market with the intention of reducing mortality. However, the nutritional aspect is very relevant, because a well-nourished organism has greater resistance to stress and disease, so that we must have control over the quality (digestible energy content), type of food and frequency of food, without neglecting the good management of the food, because this can impair the quality of it.

Maintenance of proper water temperature and water quality (dissolved oxygen [OD], pH, salinity, nitrites, nitrates and ammonium) to improve growth, survival and reduce the incidence of disease should also be considered.

This study corresponds to Stage I which aimed to evaluate growth in juveniles of L. vannamei when feeding them on commercial shrimp meal alone or supplemented with NC. The objective of this study was to evaluate the effect of inclusion in commercially-available shrimp meal of two concentrations of NC, 500 mg NC/kg meal and 1000 mg NC/kg meal, on the growth of white shrimp juveniles (Litopenaeus vannamei) under controlled laboratory conditions.

In a further study (Example 6, discussed below), we challenged the shrimp with the virus that causes white spot syndrome (WSSV).

Materials & Methods:

Shrimp from a production laboratory in the region were moved to a container with a capacity of 600 L and constant aeration. Once in that container, the shrimp were acclimatized in fiberglass tanks with a capacity of 300 L, constant aeration and water flow, controlled photo period (12 hours light, 12 hours darkness), at a temperature of 25.0±0.5° C. and fed three times a day on a commercial diet. The organisms remained in these conditions for a period of five days to check the normal behavior and good health of the same pre-requirement to start the bioassay. At the time, a histopathological analysis was carried out in order to know the initial condition of the organisms. We also performed qPCR analysis for WSSV, TSV, IHHNV and AHPND/EMS to rule out the presence of these pathogens in the shrimp.

Figure 8:
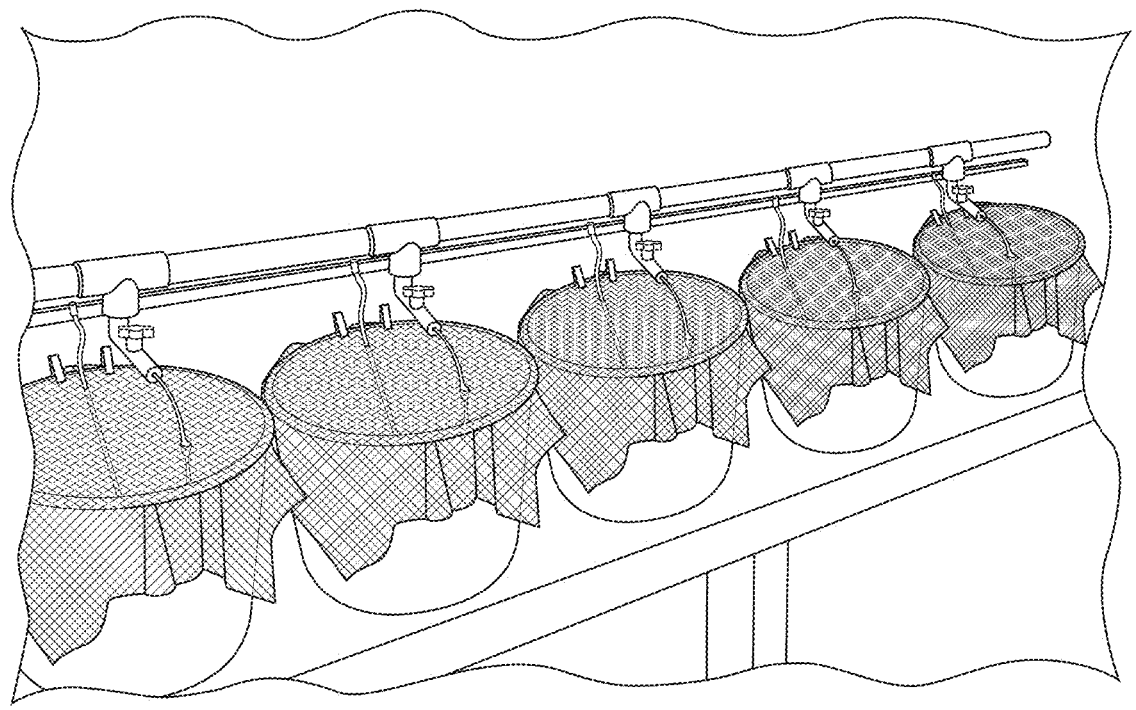
FIG. 8 illustrates the aquaculture apparatus used in certain experiments.

Once the acclimatization period was completed, the organisms were distributed into 16 Experimental Units (EU) of fiberglass with black walls and white bottom with a usable capacity of 50 L, constant aeration and continuous flow of filtered seawater at (10 m) total water replacement at approximately 7:30 h and drainage to the center (FIG. 8). In each EU, 40 organisms were placed (1.49±0.19 g in weight and 65.49±2.49 mm in length).

Figure 9A:
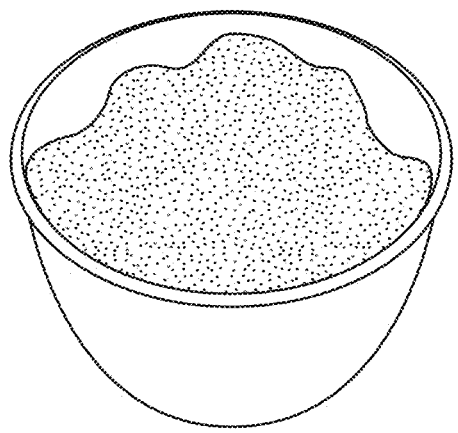
FIG. 9A, FIG. 9B, FIG. 9C, FIG. 9D and FIG. 9E illustrate the process to prepare the feed meal.
Figure 9B:
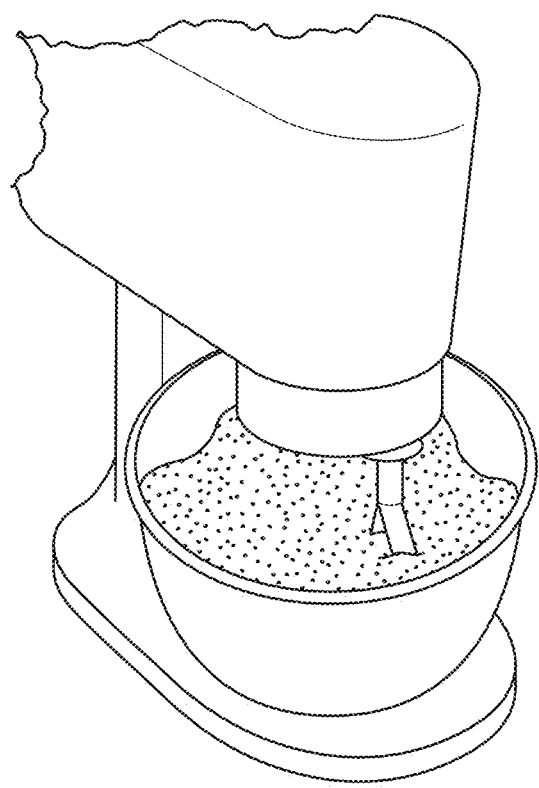
Figure 9C:
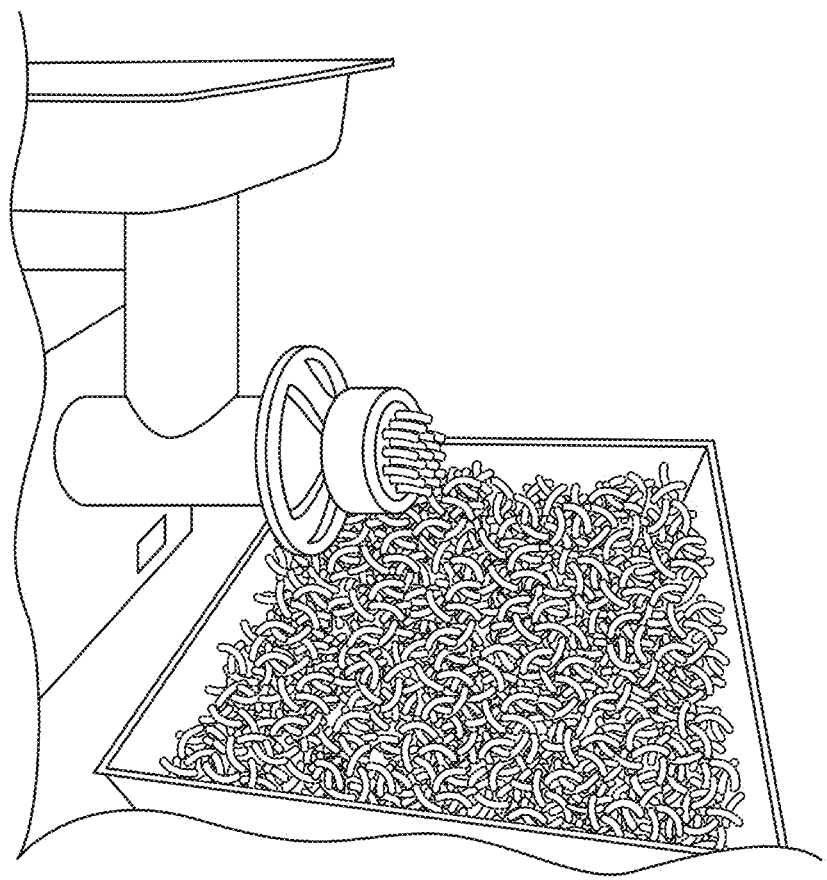
Figure 9D:
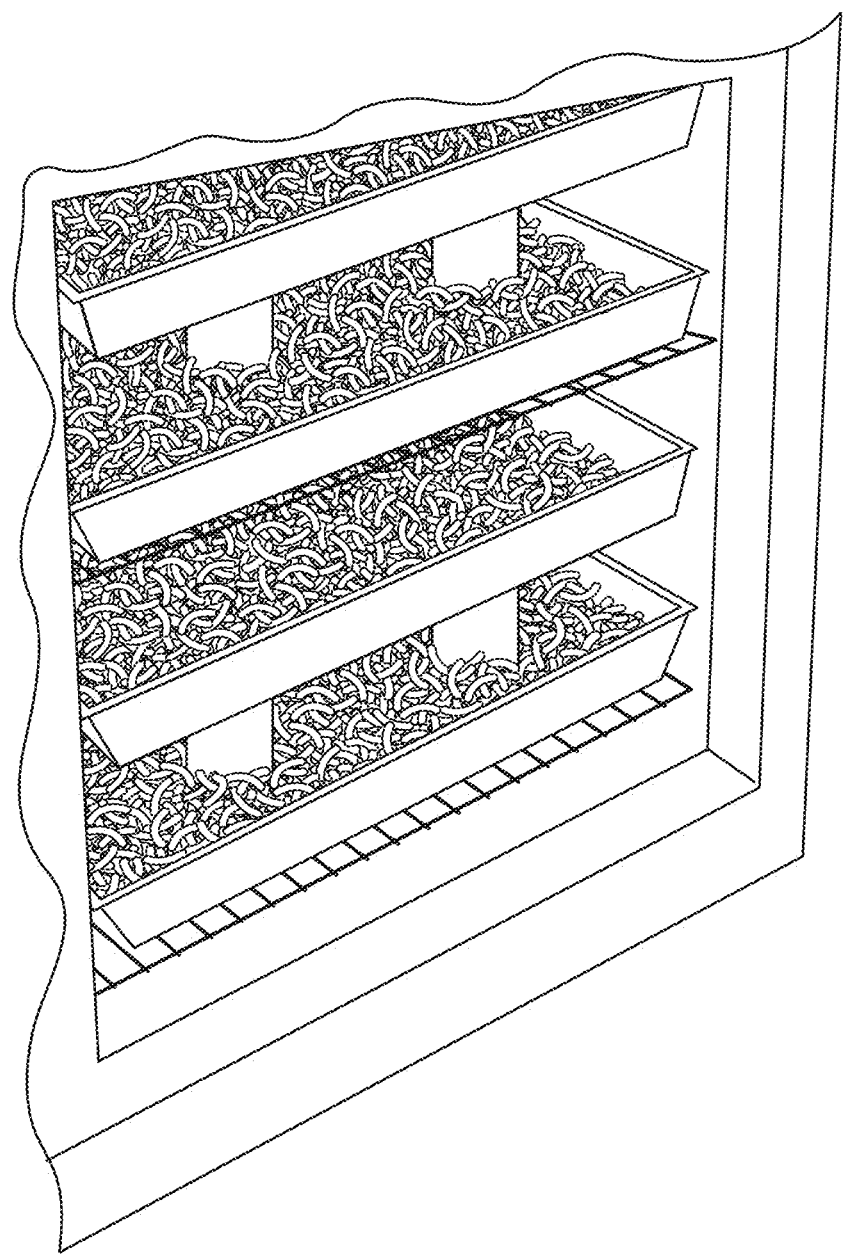
Figure 9E:
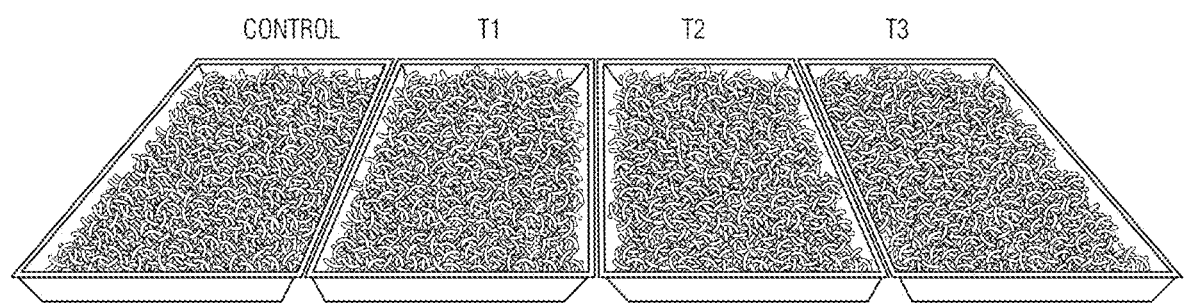

The commercial shrimp meal was ground (FIG. 9A), and reconstructed in four treatments, two with the inclusion of the different concentrations of NC, another with VIUSID™ (a commercially-available dietary supplement comprising malic acid, ascorbic acid, folic acid, glycyrrhizic acid, glucosamine, cyanocobalamine, zinc sulfate, arginine, glycine, pyridoxal and calcium pantothenate), and the control diet without any extra products (FIGS. 9B and 9C). Subsequently, the pellets were dried for 12 h in an oven at 50±2° C. (FIG. 9D), broken to the desired size (2 mm) (FIG. 9E), placed individually in labeled plastic bags and stored in refrigeration (±4° C.).

Four treatments were considered according to the labeling of the different diets tested (Table 1). The commercial diet contained 35% protein and a minimum of 7.7% fat. Each treatment featured four replicas that were randomly distributed in the culture system. All shrimp were weighed and measured individually on a digital balance (A&D EK-4100i) and with an electronic vernier respectively.

The experiment lasted 21 days, during which time the organisms were fed, calculating 9% of each EU's biomass and adjusting it according to the demand for shrimp throughout the bioassay. The feed is divided into three servings per day (08:00, 12:00 and 16:00 h). In addition, prior to the first feeding of the day, all tanks were siphoned in order to remove feces and unconsumed food. The weight of the food consumed was recorded daily.

Once the bioassay (21 days) of each EU of the system was completed all shrimp were weighed and measured individually on a digital balance (A&D EK-4100i) and with an electronic vernier, respectively, in addition to determining the number of survivors. To assess the effect of different diets on shrimp, the following biological indices (formulas are included):

a) Survival: percent of living organisms at the end of the assay
b) Weight gain
c) Length increase
d) Weight gain rate/time
e) Feed conversion rate (Shrimp weight gain/Feed weight)

Statistical Analysis:

Survival results obtained were analyzed with the Kaplan-Meier nonparametric test. For the case of the difference between weights and sizes at the beginning and end of the experiment, all the data were analyzed using a Kruskal Wallis range-difting analysis and a Dunn post hoc analysis, with the exception of the weight data at the end of the experiment, which were parametric and therefore analyzed using a 1-way variance analysis (ANOVA) and a Yourkey-Kramer post hoc analysis for different sample sizes. All analyses were performed with a 0.05 significance.

Results of weight gained (PG), increase in size (IT), Specific growth (TCE) and Food Conversion Rate (TCA) were not analyzed using statistical methods as we obtained only four data points per treatment. Such a small n does not provide reliable results, so only the values obtained for each treatment are reported.

Temperature monitoring (C), salinity (UPS, pH and OD (mg L−1), with a YSI-multimeter was performed daily. As well as ammonium (mg L−1), nitrites (mg L−1) and nitrates with a commercial kit (Saltwater Master Test Kit, Marine, API, USA).

Results:

All diets had uniform texture without fractures, nor porosity (seen from the eoscopic ester microscope). The feed pellets were stable in the water, remaining firm and compact long enough for the shrimp to consume them. The sizes of all diets were adequate, the organisms were able to hold them, swim and consume them without any problem. The feed color was beige and homogeneous for all diets (Table 1), generally considered fitness and good quality feed.

TABLE 1

Keys and general characteristics of the four diets

| CIAD Key | Treatment | Color | Smell | Buoyancy |
|---|---|---|---|---|
| C | Commercial diet | Homogeneous beige | Nice | Semifloat/submersible |
| T1 | Commercial diet inclusion NC 500 mg kg$^{-1}$ | Homogeneous beige | Nice | Semifloat/submersible |
| T2 | Commercial diet inclusion NC 1000 mg kg$^{-1}$ | Homogeneous beige | Nice | Semifloat/submersible |
| T3 | Commercial diet commercial immune-stimulant inclusion | Homogeneous beige | Nice | Semifloat/submersible |

The organisms exhibited normal activity throughout the experiment. Once siphon cleaning was completed and when providing the first feeding, the organisms responded immediately (<2 seconds) by searching for and consuming the pellets, this was observed in all treatments evaluated, including some organisms climbing to the surface at the time of uncovering the tanks before the food was supplied. "Threads" of firm stool were observed to maintain their shape, even though they were siphoned from the tank, suggesting normal food behavior in organisms in all treatments. The water in the tanks never showed turbidity or unpleasant odors in any of the treatments.

The weights and sizes of treatments at the start of the experiment did not have significant differences between them (P>0.05) (Table 2). All treatments showed significant differences (P<0.05) between the initial and final weights and sizes, indicating growth (Table 3), demonstrating that all diets were consumed and nutritiously suitable for juveniles of *L. vannamei*.

It was observed that T1 treatment showed significantly higher weight values with respect to T3 and Control (P<0.05) treatments, however, it showed no significant differences with T2 treatment. The value obtained in the "q" statistic between the T1 and T2 treatments for the Tukey-Kramer test was 3.63, the value identical to the critical value of the test, so the lack of significant differences between the treatments should be taken with caution (Table 2).

treatment and a so small n (n-4) a statistical analysis could produce unreliable results, so only the values obtained for each treatment (Table 4).

TABLE 4

Results obtained for the biological indices evaluated in this study in white shrimp (*Litopenaeus vannamei*) fed different treatments for a period of 21 days

| Treatment | PG (g) | IT (mm) | ECA (g d$^{-1}$) | ECA (% d$^{-1}$) | Tca |
|---|---|---|---|---|---|
| Control | 1.61 | 17.43 | 1.12 | 111.82 | 2.05 |
| T1 | 1.78 | 18.47 | 1.17 | 116.58 | 1.92 |
| T2 | 1.64 | 17.35 | 1.12 | 111.92 | 1.97 |
| T3 | 1.46 | 16.02 | 1.06 | 106.28 | 2.22 |

Weight Gained (PG), Size Increase (IT), Specific Growth Rate (TCE) and Food Conversion Rate (TCA)

The water quality parameters, over the experimental period, had no significant variations, the temperature ranged between 29 and 30° C., salinity from 33 to 32 UPS, pH between 7.8 and 8; dissolved oxygen from 4.0 to 5.5 mg L$^{-1}$. The values of ammonium (0.0 to 1.0 ppm), nitrites (0.0 ppm) and nitrates (0.0 ppm) remained stable and constant at low and acceptable levels for shrimp culture. None of the diets affected water quality, however, it is worth mentioning that

TABLE 2

Initial and final weights of white shrimp juveniles (*Litopertaeus vannamei*) fed different treatments for 21 days

| | Initial weight (g) | | | | | Final weight (g) | | | | |
|---|---|---|---|---|---|---|---|---|---|---|
| Treatment | Average | Maximum | Minimum | O.d. | N | Average | Maximum | Minimum | O.d. | N |
| Control | 1.51 | 190 | 120 | 0.18 | 160 | 3.12$^b$ | 4.20 | 2.00 | 0.45 | 150 |
| T1 | 1.49 | 190 | 120 | 0.19 | 160 | 3.27 a.m. | 5.00 | 1.80 | 0.57 | 145 |
| T2 | 1.48 | 180 | 120 | 0.19 | 160 | 3.12$^{tob}$ | 4.40 | 1.90 | 0.49 | 153 |
| T3 | 1.49 | 180 | 120 | 0.20 | 160 | 2.95$^c$ | 4.00 | 1.40 | 0.49 | 153 |

The averages correspond to three replicates for each treatment and n for each treatment The size values of the treatments had significant differences between themselves, with T1 and Control treatments having the highest growth, followed by T2 treatment and finally with T3 treatment, treatment that had significant differences with T1 and Control, but not with T2 treatment (Table 3).

the flow of water was always open and with total replacement approximately every 7:30 h.

No AHPND, TSV and WSSV were detected in the batch analyses of the seed shrimp. However, the presence of the IHHN virus was detected, this virus is considered endemic

TABLE 3

Initial and final sizes of white shrimp juveniles (*Litopenaeus vannamei*) fed different treatments for 21 days

| | Initial size (mm) | | | | | Final size (mm) | | | | |
|---|---|---|---|---|---|---|---|---|---|---|
| Treatment | Average | Maximum | Minimum | O.d. | N | Average | Maximum | Minimum | O.d. | N |
| Control | 65.69 | 70.79 | 61.67 | 2.40 | 160 | 83.12 a.m. | 92.57 | 71.93 | 4.01 | 150 |
| T1 | 65.50 | 70.79 | 61.67 | 2.53 | 160 | 83.97a | 95.33 | 71.25 | 4.71 | 145 |
| T2 | 65.35 | 69.49 | 61.67 | 2.43 | 160 | 82.71a$^b$ | 93.20 | 64.98 | 4.48 | 153 |
| T3 | 65.43 | 69.49 | 61.67 | 2.60 | 160 | 81.44$^b$ | 89.27 | 65.78 | 4.58 | 153 |

Figure 13:
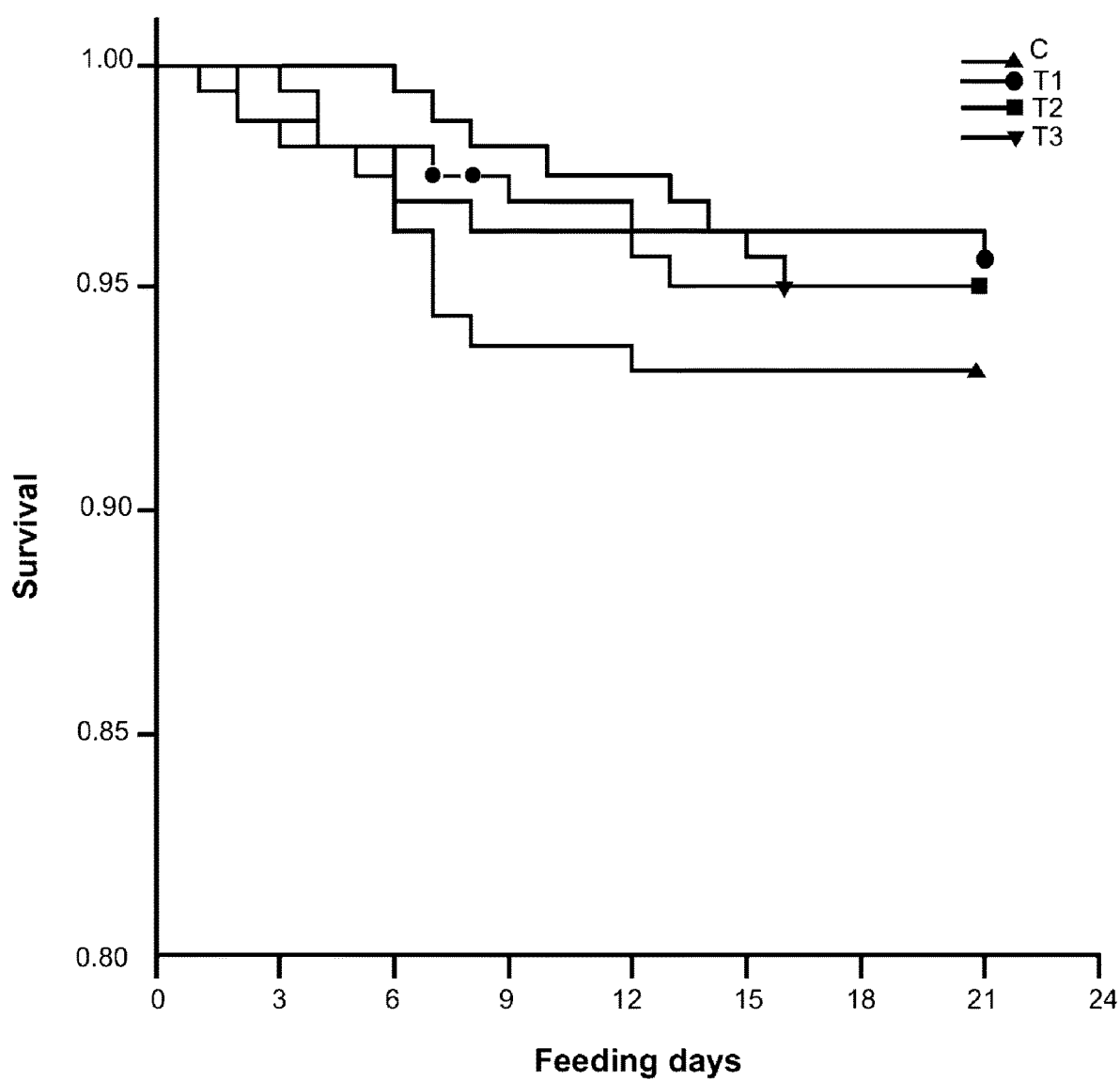
FIG. 13 provides Kaplan-Meier survival curves for Experiment 5. Control (C), Treatment 1 (T1), Treatment 2 (T2) and Treatment 3 (T3).

The averages correspond to three replicates for each treatment and n for each treatment At the end of the evaluation period the average survival recorded for all treatments was 96, 93, 95 and 95% for treatments C, T1, T2 and T3, respectively. No significant differences were found in the survival of treatments (P>0.05) (FIG. 13).

The results of (PG), IT, ECA and ACT were not analyzed using statistical methods as only four data are available per in the region. The main reported effects of this virus are deformities in rostrum and reduction in shrimp growth. In the organisms analyzed at the beginning of the experimentation, no associated histopathological lesions were observed to the virus, nor were clinical signs attributable to IHHNV presented during the development of the bioassay. Taking into account the above and in line with the results obtained in growth with respect to weight and size, it is still that the virus does not have a negative effect on the organisms used in this trial.

After the Stage I Nutrition Bioassay was completed, the organisms were transferred to the CIAD Virology Bioassay Laboratory, Mazatlan Unit, where Stage II (dEsafio WSSV) was carried out.

Conclusions

The inclusion of NC is simple as the product is perfectly pulverized, dry and homogeneous. The inclusion of NC does not change the appearance or acceptability of the pellet to consumption by the shrimp. All treatments were accepted by the organisms, presenting almost immediate reaction (<2 sec) to capture and start consuming.

Shrimps were negatively tested for AHPND, TSV and WSSV. Presence of IHHNV was detected, with no effect on bioassay results. The growth (weight) results obtained suggest a positive effect on shrimp from treatments in which NC was Included™. Apparently, the inclusion of 500 mg NC per kg of standard meal is sufficient to cause such an effect.

The ACT also suggests better consumption of food, with lower consumption against greater weight gain for treatments in which NC was Included™.

Example 6

This study evaluates the effect of NC included in the feed of juvenile Pacific white shrimp (Litopenaeus vannamei) for a 21 day feeding period. Two different concentrations were tested, 500 mg NC/kg conventional meal and 1000 mg NC/kg conventional meal. Significant growth improvements (p<0.05) was demonstrated in shrimp fed with 500 mg NC/kg meal concentration, when compared to the control (no NC). No significant differences in survival were observed between treatments. Also histological analyses showed a healthy digestive tract in shrimps fed with 500 mg NC/Kg of conventional meal.

For this study we prepared a mixed seaweed powder to improved shrimp survival and growth. Two different concentrations were incorporated in a standard commercially-available shrimp meal (35% protein and >7% lipids content) and evaluated efficiency on growth (size and weight), survival and healthy condition with Hp and gut structures.

Materials And Methods:

Approximately 1,500 shrimps were obtained, without a selection protocol, and with no distinction made as to whether the shrimp were male or female, from a local hatchery and transported to the facilities where the trials were conducted. Before the experiment, we sorted the fish to obtain a group with a homogeneous baseline size. A five days period was left to evaluate shrimp's health status. Pooled samples were tested for Acute Hepatopancreatic Necrosis Disease (AHPND), White Spot Syndrome Virus (WSSV), Taura Syndrome Virus (TSV) and Infectious Hypodermal and Hematopoietic Necrosis Virus (IHHNV) using a commercial real time PCR detection method (Real Time IQReal™). Additionally, nine shrimps were taken for histological analysis. During acclimation, shrimps were kept in 300 L fiberglass tanks with a 12/12 hour light/dark photoperiod, 24.0±1° C. and fed a standard commercially-available shrimp meal (protein 35% lipid 7.7%) three times a day.

After acclimation, 40 shrimps (1.49 g average±0.19 g, 65.50±2.50 mm) were stocked randomly in each of the 18 tanks (50 L) in the Nutrition Culture System. Four treatments were considered, with four replicates each (Table 1). All shrimps were weighted and measured with A&D EK-4100i balance and a digital caliper, respectively. Before the first feeding with experimental diets, shrimps were left to fast for 12 h. During the experiment, shrimps were fed (9% of biomass) three times a day, at 8:00, 12:00 and 16:00 h. Daily, before first feeding, feces and uneaten pellets were siphoned out from each tank.

NC was incorporated into the standard meal as follows: Pulverize commercial feed pellets using a mill. (Nixtamatic®, Mexico). Mix the pulverized feed pellets with the different products to evaluate (Table 1) until they are perfectly integrated using a mixer (Blazer® by JR, China). Hydrate the mix with water to create a homogeneous mass (Blazer® by JR, China). Re-pelletize the moistened mixture in a meat mill (Tor Rey®, Fundición Torrey S.A. de C.V., Mexico). Dry the resulting feed pellets at 40° C. during 12 hours in a conventional oven (Shel Lab®, Sheldon manufacturing Inc. USA). Cut and sieve the feed to assure proper size (<3 mm).

This process also was done to the standard (control) meal, albeit without the addition of any product, in order to maintain the resulting pellets at equal conditions.

TABLE 1

Characteristics and codes of treatments used in experiment with Litopenaeus vannamei.

| Treatment | Code | Immunostimulant | % products inclusion |
|---|---|---|---|
| Control | C | None | 0 |
| 1 | T1 | NC | 500 mg NC/Kg of control diet |
| 2 | T2 | NC | 1000 mg NC/Kg of control diet |
| 3 | T3 | VIUSID ™ | 1 mL VIUSID/Kg of control diet |

Water parameters (temperature, salinity and dissolved oxygen) were determined on a daily basis using an YSI-multimeter 85. Commercial kits (Saltwater Master Test Kit, Marine, API, USA™) were used to measure pH, total ammonium, nitrate and nitrite. Weight (AND Ek-4100 balance) and length (digital calliper) were measured of all survival shrimps of each tank at the end of the experiment (21 days).

Histology:

Previous fixation, shrimps were selected after uropods were checked at the microscope (Olympus® CX31) to evaluate the appearance of the epidermis and cuticle to guarantee all shrimps were in intermolt stage (Thuong et al. 2016). Nine shrimps were fixed in Davidson's solution at the beginning of the experiment. At the end of the experiment (21 days), six shrimps from each treatment were also fixed. Afterwards, shrimp's tissue was dehydrated and embedded in paraffin, 4 μm sections were sliced and stained with hematoxylin & eosin (Bell and Lightner, 1988) before being observe at the microscope (Olympus CX31) to identify tissue microanatomy.

Statistical Analyses:

Survival results were analyzed with nonparametric Kaplan-Meier's test. Difference between weights and sizes at the beginning and at the end of the experiment were analyzed with Kruskal Wallis ANOVA on ranks and a post hoc analysis of Dunn. Weight data at the end of the experiment, which were parametric, were analyzed using a 1-way analysis of variance (ANOVA) and a post hoc analysis of Tukey-Kramer for different sample sizes. All analyzes were performed with a 0.05 significance.

Results of weight gain (WG), size increment (SI), specific growth rate (SGR) and food conversion rate (FCR) were not analyzed by statistical methods, there are only four data per treatment and with one n so small (n=4) a statistical analysis could generate inaccurate results, so only the values obtained for each treatment are reported.

Results:

No significant differences between treatments (p>0.05) were observed in shrimps, at the beginning of the feeding period, with an average initial weight and size of 1.49±0.19 g and 65.49±2.49 mm, respectively. At the end of the feeding period, treatment T1 showed significantly higher weight values compared to treatments T2, T3 and C (p≤0.05) (Table 2). Size values between treatments were significant different (p≤0.05), treatments T1 and C had the highest size values, followed by T2 and, at last, treatment T3 (Table 2). At the end of the evaluation period, the average survival was 96, 93, 95 and 95% of each treatment C, T1, T2 and T3, respectively. No significant differences were observed (p>0.05).

Figure 11:
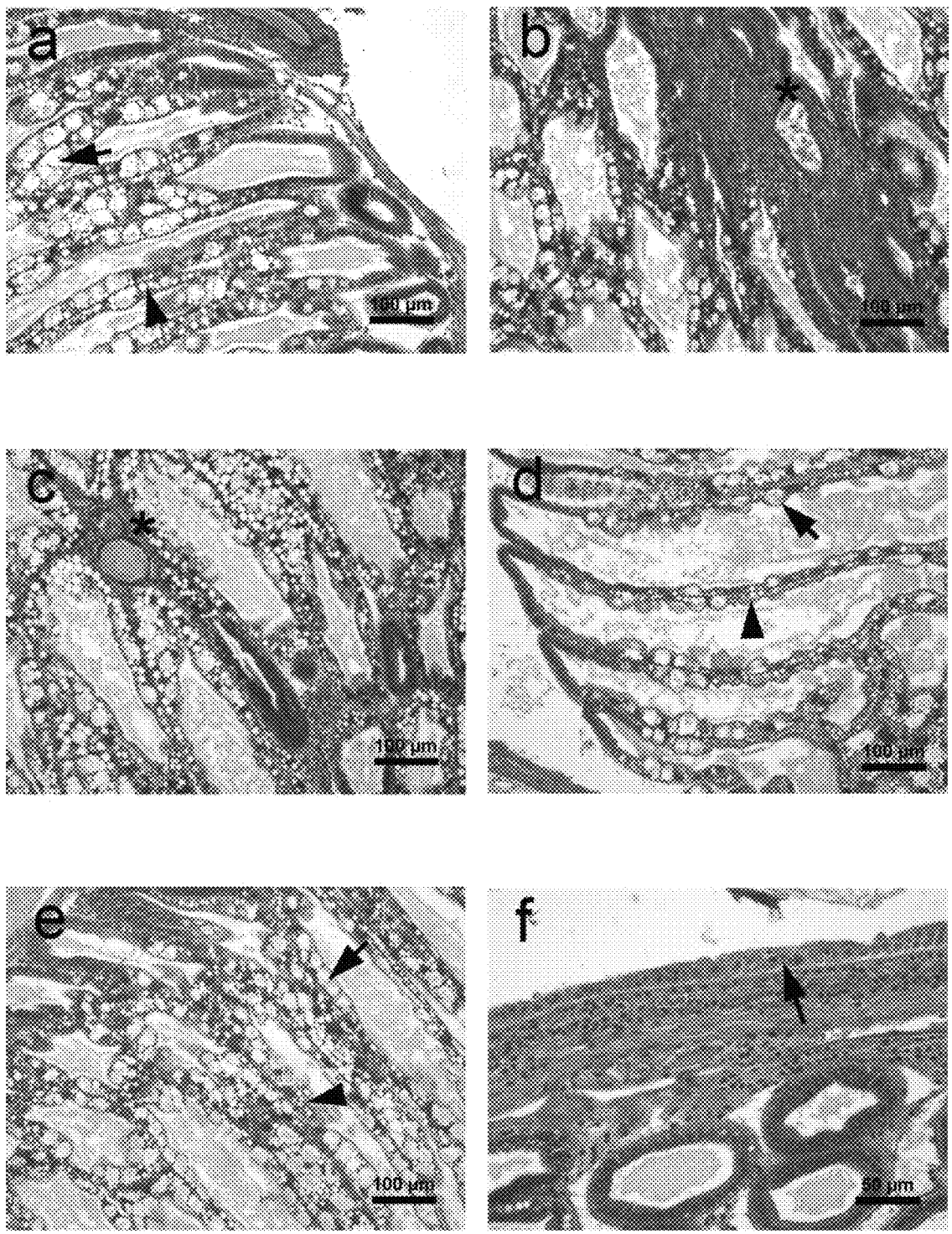
FIG. 11 shows microphotography of hepatopancreas (a-e) and anterior intestine (f) of *L. vannamei* shrimp fed the treatments on day 21. a) Tubular epithelium with abundant B cells (arrow) and R cells (arrow head) in T1. B) and c) Tubule with necrosis and hemocytic infiltration in intertubular tissue (*) in T2 and T3 respectively. d) Tubular epithelium with reduction of the size of vacuoles in cells B (arrow) and R (arrow head) in T3. e) Tubules with abundant B cells (arrow) and R cells (arrow head) in C. f) Epithelium intestine with focal necrosis (arrow) and slight hemocytic infiltration in T3. H & E staining.

At the end of the experiment (21 days), Hp of treatment T1 organisms showed a normal tubular structure and epithelium with abundant vacuoles in R and B cells (FIG. 11a). Focal tubular necrosis (G1) and hemocytic infiltration were found in intertubular tissue (FIGS. 11b and 11c) in 2/6 and 1/6 organisms of the treatments T2 and T3 respectively. In addition, 2/6 and 3/6 organisms from treatments T2 and T3 respectively, presented a smaller size of vacuoles in R and B cells (FIG. 11d), in comparison with treatment T1.

From treatment C, 5/6 organisms showed a normal condition (FIG. 11e), similar to that observed in treatment T1; only one shrimp from treatment C presented a slight reduction in the size of vacuoles in R and B cells. On the other hand, the intestinal tract did not present lesions in the organisms fed with the treatments T1, T2 and C; however, in the treatment T3, it was observed that 50% (3/6) of the organisms showed a slight hemocytic infiltration and focal necrosis of the epithelial cells of the anterior intestine (FIG. 11f).

Lymphoid organ was another tissue that showed alterations in its structure due to the development of spheroids

| | | | Shrimp growth rate | | | | | | |
|---|---|---|---|---|---|---|---|---|---|
| T | $W_0$ (g) | $W_f$ (g) | $S_0$ (mm) | $S_F$ (mm) | $n_F$ | WG | SI | SGR | AFC |
| C | 1.51 ±0.18 | $3.12^b$ ±0.45 | 65.69 ±2.40 | $83.12^a$ ±4.01 | 150 | 1.61 | 17.43 | 1.12 | 2.05 |
| T1 | 1.49 ±0.19 | $3.27^a$ ±0.57 | 65.50 ±2.53 | 83.97a ±4.71 | 145 | 1.78 | 18.47 | 1.17 | 1.92 |
| T2 | 1.48 ±0.19 | $3.12^b$ ±0.49 | 65.35 ±2.43 | $82.71^{ab}$ ±4.48 | 153 | 1.64 | 17.35 | 1.12 | 1.97 |
| T3 | 1.49 ±0.20 | $2.95^c$ ±0.49 | 65.43 ±2.60 | $81.44^b$ ±4.58 | 153 | 1.46 | 16.02 | 1.06 | 2.22 |

T = Treatment Initial and Final weight ($W_{0/F}$), Initial and Final size ($S_{0/F}$), Weight gain (gm) (WG), Size increment (mm) (SI), Specific growth rate (grams/day) (SGR) and Average food consumption (AFC) of White shrimp (*Litopenaeus vannamei*) fed different diets with or without NC for a 21 days period. Letter indicate significant differences (p ≤ 0.05) a < b < c. n = 160

The experiment was in an open water system, with the total water replaced every 7:30 hr.

Water quality parameters during the 21 experimental days demonstrated no significant differences between treatments and tanks. Temperature was 29±1.0° C., salinity values were 33±1.0 PSU, pH varied 7.8±0.2; and dissolved oxygen was 4.0 to 5.5 mg $L^{-1}$. Total ammonia (0.0 a 1.0 ppm), nitrites (0.0 ppm) and nitrates (0.0 ppm) values kept stable and acceptable for shrimp culture conditions.

The qPCR test for AHPND, WSSV and TSV were negative. Nevertheless, IHHNV was positive with very low viral load (<$10^1$). Histopathological results demonstrated non-viral inclusion bodies, neither signs or lesions attributable to the virus before or during the experimental period. As mentioned before, all treatments produced growth (weight and size) significantly different between initial and final measurements (Table 2). No clinical signs attributed to IHHNV were observed during the acclimatization period nor the experimental period.

Figure 10:
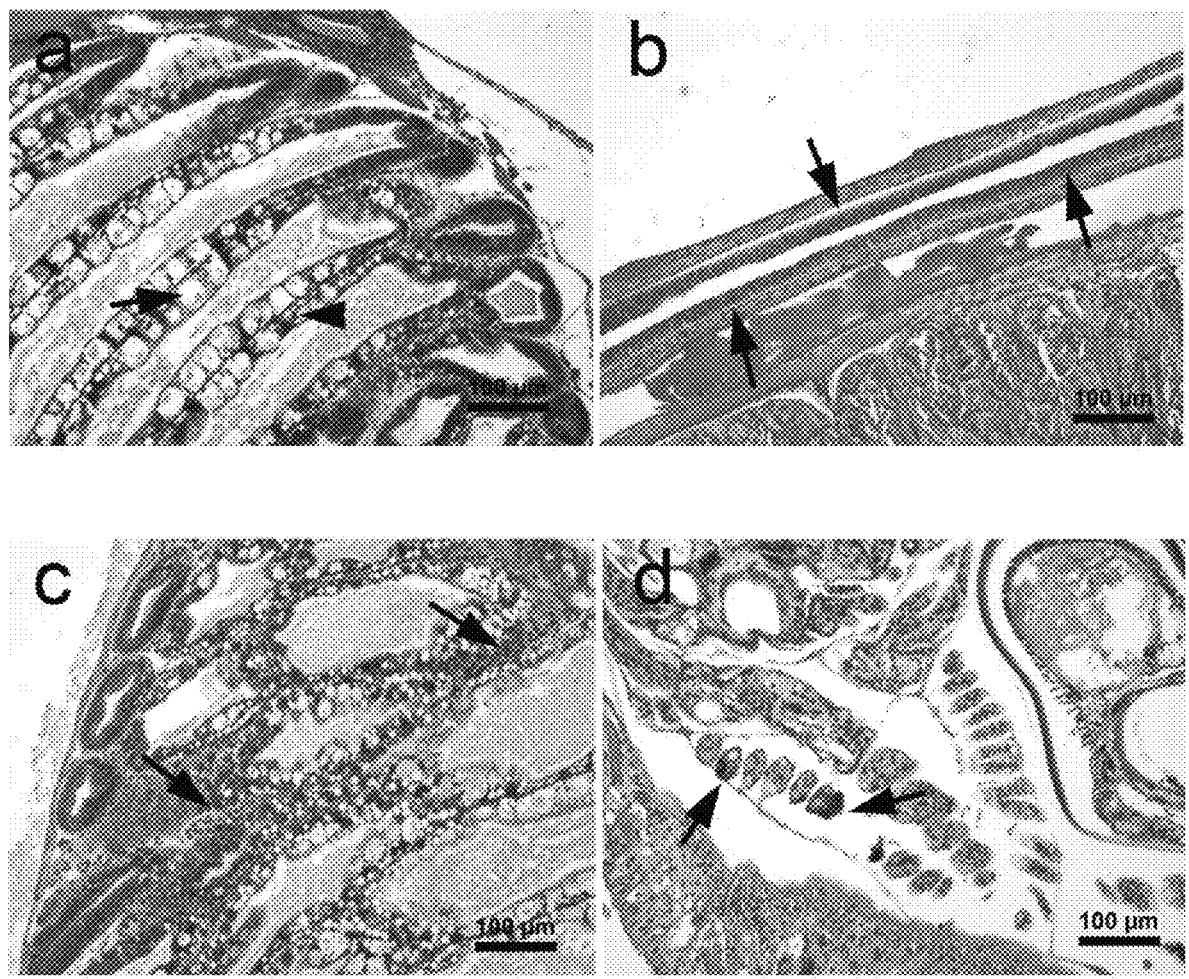
FIG. 10 provides microphotography of *L. vannamei* shrimp tissues at the beginning of feeding with experimental diets. a) Tubules of the hepatopancreas in longitudinal section, where a normal tubular structure is observed, with abundant vacuoles in cells R (arrow head) and B (arrow). b) Normal epithelium of the midgut (arrow). c) Tubules of hepatopancreas, showing focal hemocytic infiltration (arrow) in intertubular tissue. d) Branchial tissue with melanization and necrosis (arrow) in secondary filaments. H & E staining.

The histopathological analysis performed on the organisms collected at the beginning of the experimentation exhibited an Hp and intestine with normal tissue structure (FIGS. 10a and 10b). We observed 7/9 organisms without significant pathological changes in organs and tissues. Focal hemocytic infiltration in inter-tubular tissue (FIG. 10c) of the Hp was observed, with no evidence of tubular epithelial damage. In addition, 2/9 organisms presented spheroid formation in lymphoid organ; melanization and focal necrosis in cuticle and secondary lamellae (FIG. 10d) possibly derived from mechanical injuries during transportation.

Figure 12:
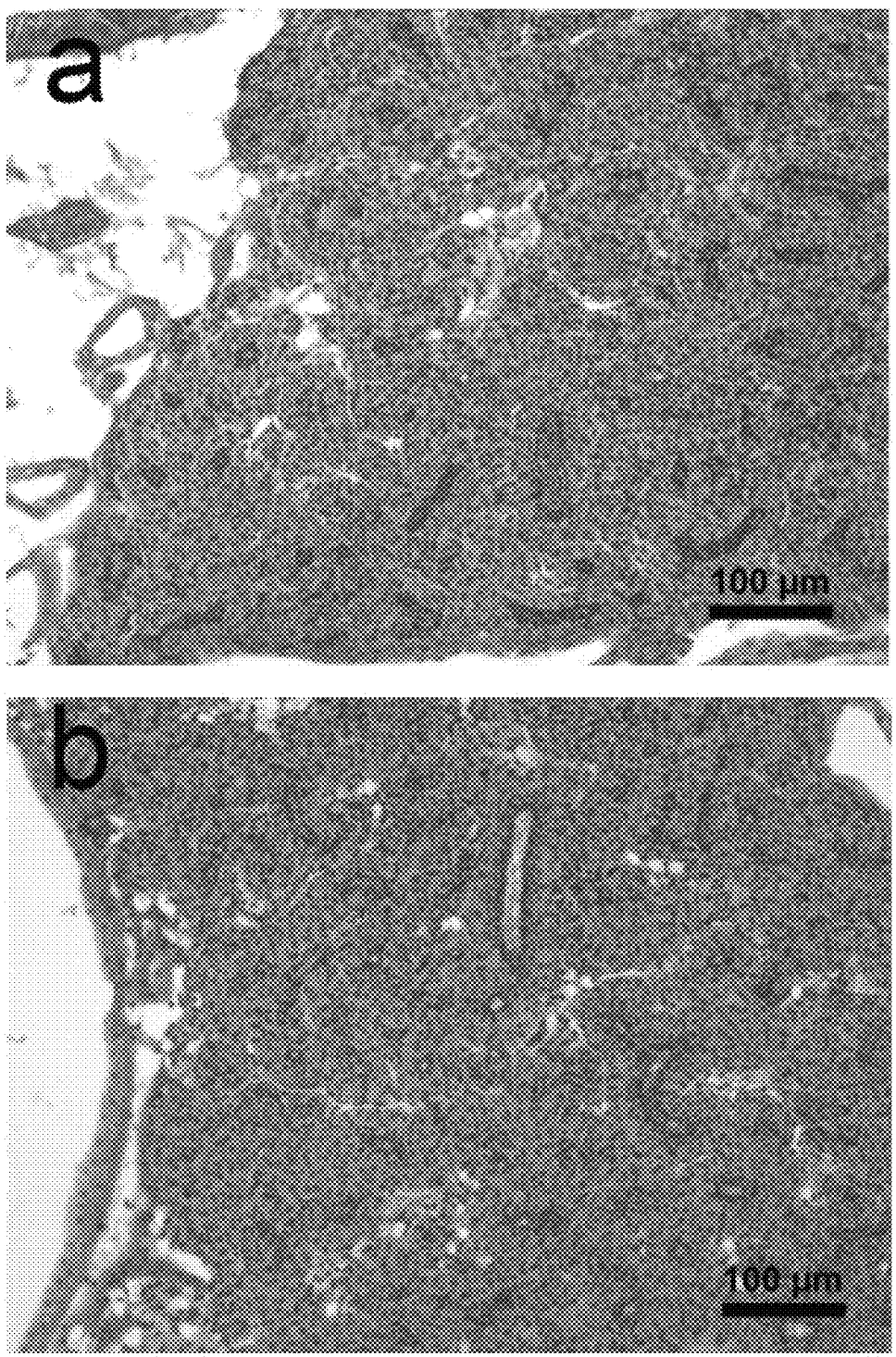
FIG. 12 shows microphotography of lymphoid organ (a and b) of *L. vannamei* shrimp fed the treatments on day 21. a) Tubules of the lymphoid organ where spheroid development and accumulation of hemocytes are observed in the lumen of the tubules. b) C. H & E staining.

(FIG. 12a). Treatments T2 and T3, presented the same alteration, 4/6 and 3/6 organisms respectively, compared with the treatments T1 and C (FIG. 12b) where it was observed only in 1/6 and 2/6 organisms, respectively. In addition, it was observed that in the four treatments (T1, T2, T3 and C) some organisms (3/6, 4/6, 5/6 and 1/6 respectively) present accumulation of hemocytes in the lumen of the tubules of the lymphoid organ.

Discussion:

Considering that feeding is 50% of the total cost productions in a shrimp hatchery, the importance of an adequate diet is relevant in order to optimize harvesting time and increasing survival. NC is a well presented, seaweed-based powder with characteristics that make it an easy and suitable additive for optimizing commercial fish-farming diets. According to our data, the best inclusion of NC is 500 mg NC per kilogram of conventional feed. We found that inclusion of NC improves average food consumption (AFC) and produces heavier shrimp.

Intriguingly, our results also demonstrate that even with viral infection by IHHNV (<$10^1$), shrimps demonstrated a positive effect in growth, gaining 0.6 g body weight per week (Table 2). According to Leyva-Madrigal et al. (2011) IHHNV impairs growth, producing dwarfism, cuticle deformities and size heterogeneity. However, during our observation period (10 days) prior to the development of the trial, no clinical signs associated with the virus were observed. The introduction of IHHNV into shrimp farms in northwestern Mexico and wild shrimp stocks was done during the late 1980s and early 1990s (Pantoja et al., 1999). Due to its prevalence and incidence, the authorities responsible for the health of aquatic organisms in the country, consider it as endemic (DOF, May 4, 2016).

Although IHHNV was detected by PCR, histopathological analysis did not show the characteristic viral inclusion bodies of the disease (eosinophilic inclusion body Cowdry type "A"). This fact and the lack of external signs related to IHHNVs infections, could be attributed to the low viral charges detected ($<10^1$) and the tolerance, or low susceptibility to the virus, developed by the organisms (viral accommodation). Several publications have reported the high prevalence of the virus in populations of *L. vannamei* wild and cultivated along the Northwest coast of the American continent (OIE, 2017).

Example 7

The study was conducted at the Aquadvise Quillaipe Aquaculture Center (CAQ)—Fundación Chile, located on Route 7, Carretera Austral km 23.8, Quillaipe sector, Puerto Montt, Chile. The objective of the study was to evaluate the efficacy against *Piscirickettsia salmonis* of NC added to food in an Atlantic salmon cohabitation challenge model. Materials & Methods:

Experimental Design

Species: Atlantic salmon (*Salmo salar*), number of fish=540, hainvg an average initial weight of 150 g (CV<15%) were obtained from the fish farm Caliboro, Trusal S.A, located in Los Angeles, Chile. The fish were sanitary analyzed to confirm the absence of pre-existing pathogens such as Infectious Pancreatic Necrosis Virus (IPNV), *Renibacterium salmoninarum* (BKD), Infectious Salmon Anemia Virus (ISA) and Piscine reovirus (PRV).

Feed was an industry-standard aquaculture feed. N1 is a feed additive comprising 96% (w/w) dried seaweed powder (the dried seaweed contains a mixture of various types of seaweed but does not contain *Macrocystis pyrifera* seaweed) and 2% (w/w) andrographolides. Gold 71 is a feed additive comprising 71% (w/w) dried seaweed powder (the dried seaweed contains a mixture of various types of seaweed but does not contain *Macrocystis pyrifera* seaweed), 10% (w/w) grape seed extract, 10% (w/w) shisandra berry extract, 4.75% (w/w) curcuminoids and 2% (w/w) andrographolides.

The trial began with an acclimatization period on day −20. We obtained 18 aquaculture tanks each of a 350 L capacity. Each was configured with 35 Atlantic salmon. We divided the tanks into two groups of nine tanks, one for the "shedder" (infected) group and the other for the non-infected group. Starting weights of the fish averaged ~148.3 g/fish for the test population and 173.1 g/fish for the control population.

The fish were kept in fiberglass ponds in a 70/30 water reuse system during the acclimatization and experimental period and a 90/10 during the challenge with *P. salmonis*. The ponds had a water flow that allowed a replacement of 1.2 spare parts hour prior to the challenge and 0.8 L/h during the challenge with *P. salmonis*, were supplied with seawater pumped directly from the sea at room temperature and salinity and during the challenge the water was maintained at 15° C. by gas boiler. In addition, incoming seawater was filtered at 60 µm and disinfected with a UV system. The ponds were illuminated with fluorescent lights located on the roof of the building. The photoperiod was 24 hours light.

At day=0, a measurement of weight and length of each of the fish was made.

At day=1, we began delivery of the experimental diets and three experimental groups were set up in triplicate: industry-standard feed as the control diet, industry-standard feed supplemented with Gold 71™ and industry-standard feed supplemented with N−1. This period lasted 14 days.

On day=15, the fish were transferred to a unit, to begin the challenge by cohabitation with "Shedder" fish infected with *P. salmonis*. Prior to the transfer, basal samples of 5 fish per pond were taken.

Figure 14:
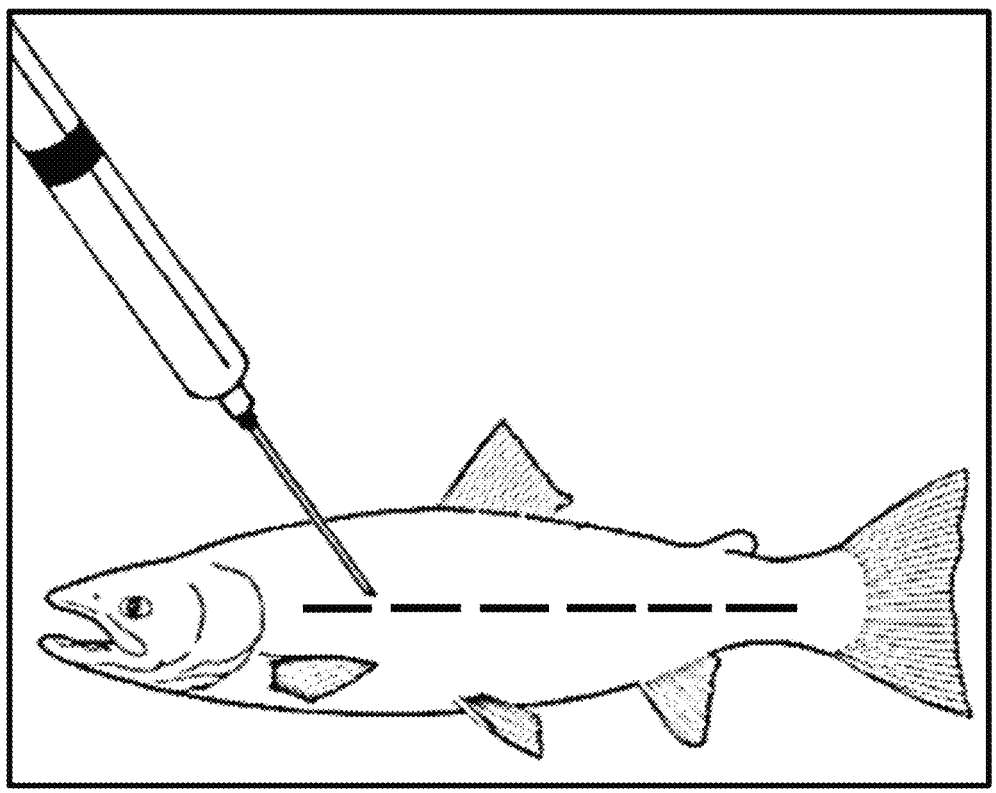
FIG. 14 is a diagram of the site of intra-peritoneal injection.
Figure 14:
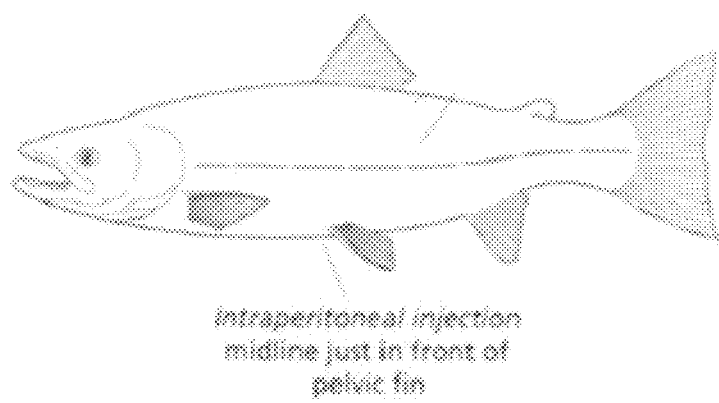

Two hundred seventy (270) healthy fish were inoculated with *P. salmonis*. The inoculation was performed intra-peritoneally (IP) by injecting 0.2 mL (approximately 8,532 bacteria) of an inoculum of *P. salmonis* strain EM90 from the Fraunhofer laboratory, with an inoculum titer 102.25 DICT50/mL, obtaining a theoretical bacterial quantification of 104.63 Bacteria/mL (42,658 bacteria/mL). The inoculation procedure was as follows. The fish were anesthetized with a dose of 17-20 mL of 50% isougenol in 100 L of water to induce deep sedation. Inoculation was performed with a SOCOREX® brand multi-dose syringe. FIG. 14 is a diagram of the site of intra-peritoneal injection. Before the injection, a needle evaluation was performed to prevent damage to the internal organs. The inoculation was performed via intra-peritoneal (IP) injection. The inoculation procedure lasted one day and all the fish were weighed and measured.

In addition, the inoculated fish (we often here refer to such fish as "Shedders" because they can shed pathogenic bacteria into the tank. We also occasionally refer to such fish as "Trojans" because, like a Trojan horse, they serve as a vector to introduce pathogenic bacteria into an otherwise-healthy population) were marked with a cut in the fat fin to differentiate them from cohabiting (non-inoculated) individuals.

Once the inoculation process was completed, these "Shedder" fish were then distributed in nine 350 L ponds, 30 Shedders/pond. In addition, an equal number of healthy (non-inoculated) fish were transferred into each pond to co-habit with the Shedders. Each pond therefore included 30 inoculated Shedder fish and 30 non-inoculated or "cohabiting" fish.

The fish were so maintained for 70 days. During this period different ponds were fed different test diets. Throughout the study the food was supplied manually at apparent satiety at least four times a day, trying to recover at least 15% of the food not consumed, to ensure satiety. Unconsumed food was collected twice a day by flushing method. Then 30 pellets were counted for each pond collected and weighed, with this the amount of pellets not consumed per pond was estimated. The amount of food not consumed was calculated by multiplying the amount of pellets not consumed by the average weight of 1 dry pellet (after sampling weight of 100 dry pellets and calculating the average weight of 1 pellet of each diet).

The fish were weighed and measured daily. The mortalities generated during the trial were identified by pond and by whether the individual had been inoculated. The fish were weighed and measured daily.

On the 70$^{th}$ day, the entire surviving population was sacrificed and we recorded each individual fish's weight, length, degree of internal necropsy, individual photography and organ sampling.

During the main challenge, samples of the previous kidney and liver were taken at the entire mortality of cohabiting fish and 1 Shedder from each pond, for confirmation of *P. salmonis*. The same samples were taken at day 70 (final sampling) at 10 cohabitants and 1 surviving Shedder from each pond. The samples were stored in RNA later at −20° C.

We analyzed 27 organ tissue samples (including Shedders and co-inhabitants, and including mortalities and survivors) by qPCR, by means of DNA detection, the results obtained are shown in Annex 5.

Figure 15:
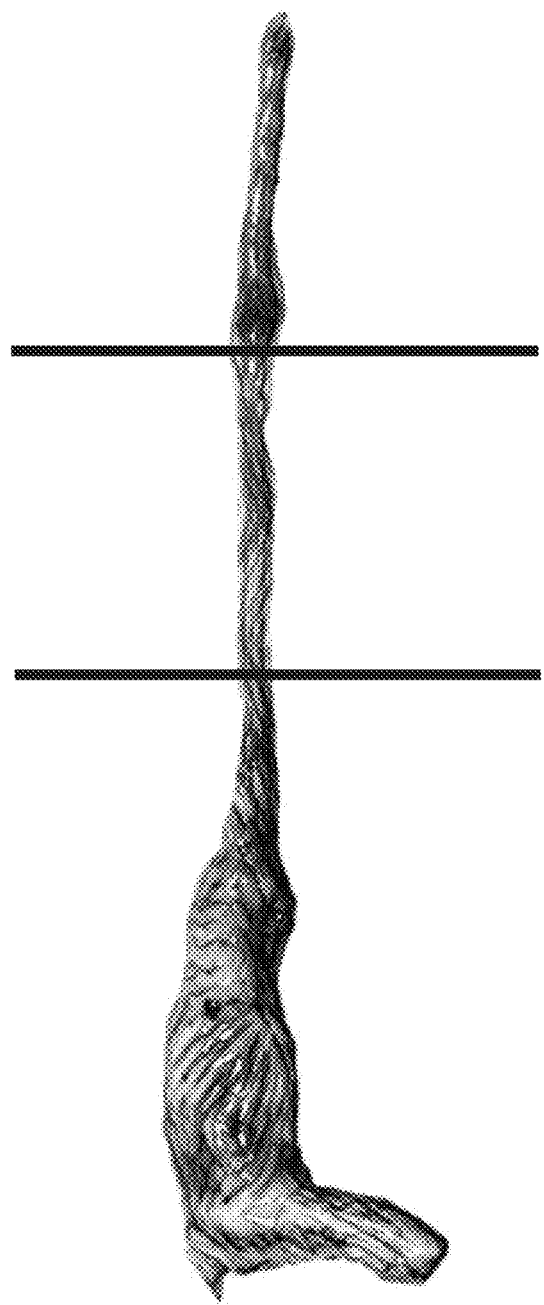
FIG. 15 shows a fish gastrointestinal tract indicating the divisions of the three areas evaluated.

In addition, necropsy was performed on each fish, assessing the gastrointestinal content at all mortality, defining the degree of this content as; empty (no stool or only in the distal I.), full (middle and posterior intestine), half of the distal intestine (50% of the distal intestine) or last stretch of the distal intestine (25%). FIG. 15 indicates the different gastrointestinal regions.

Liver, anterior kidney and intestine samples were taken before 10% of mortality, 10 cohabitants and 1 surviving Shedder per pond and were fixed in 10% buffered formalin for histoscore analysis (data not shown). Also, the following information of all the fish was recorded: Pond of origin, Group, Weight, Length, and an individual photograph of mortality and 11 survivors per pond (Annex 5).

At the end of the study all surviving fish were euthanized with an anesthetic overdose. The elimination of all euthanized fish was recorded during and at the end of the study. Fundación Chile was responsible for the elimination of fish and ensured that the elimination was carried out in accordance with all relevant guidelines, codes of good practice, procedures and legal regulations.

Adverse Events.

On day 48 post challenge, at approximately 9:30 p.m., the night operator responsible for the unit, when proceeding with the usual round, observed a problem with the oxygen diffuser of the Pond No. 13 (Gold 71 Diet), which diffuser had detached itself from the bottom of the pond and was injected on the water column. Seeing this, the night operator proceeded to call the maintenance staff, who immediately addressed the room and repaired the diffuser. For this, he closed the oxygen regulating key of the pond and involuntarily forgot to open it again, leaving the place at 10:20 p.m. Upon entering the night operator again, at approximately 00:00 hours, it was noticed that in pond 13, replica of the Gold 71 diet, there had been mortality, when checking the pond he observed that the oxygen valve was closed and proceeded to open it. This event caused the death of 29 fish due to low oxygen, leaving 8 fish in the pond as survivors. The number of dead fish were as follows: 25 Cohabitants and 4 Shedders. The surviving fish were weighed, measured and subsequently eliminated.

To evaluate the continuity of the study when evaluating two replicates of the Gold 71 diet, compared to the 3 replicas of the N1 and Control diet, after the 48th post-challenge week, cumulative mortality was evaluated, to verify if there were significant differences. Where it was observed that there were no differences in evaluating the treatments with each other, with two and three aftershocks.

Figure 16:
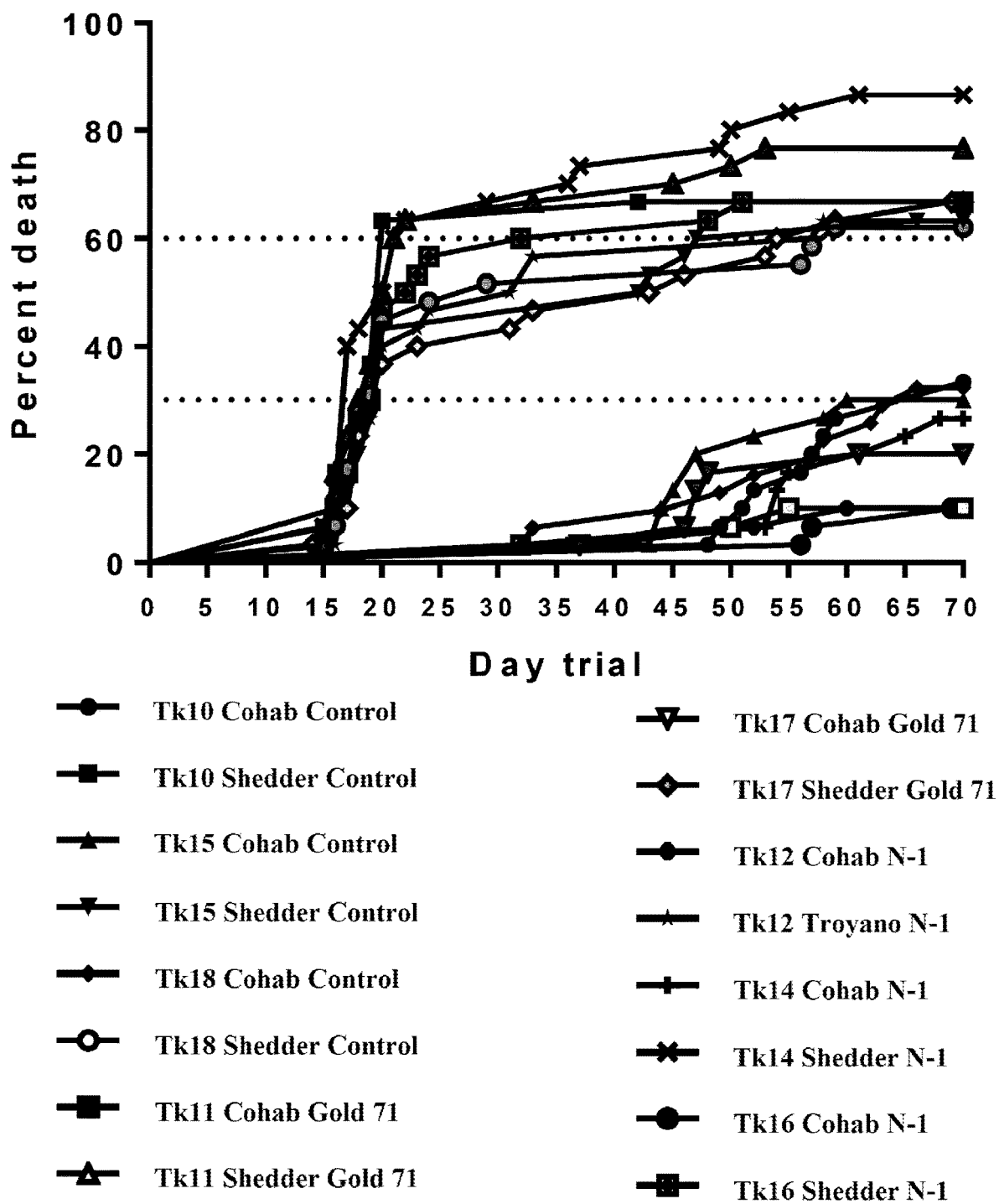
FIG. 16 shows cumulative mortality of inoculated ("shedder" or "Trojan") and non-inoculated ("cohabitation") populations, challenge with *P. salmonis*, day 70 post-challenge.
Figure 17:
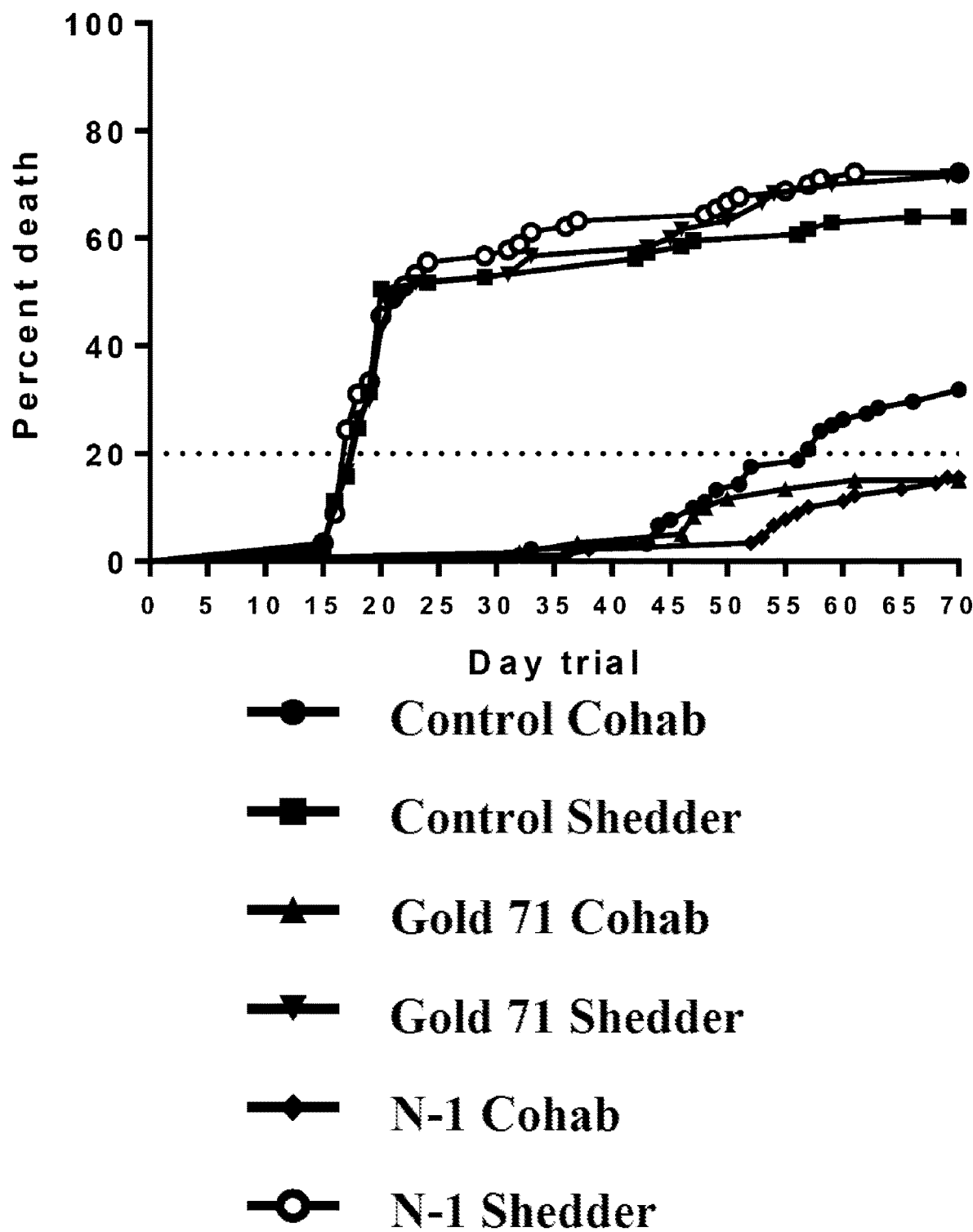
FIG. 17 shows cumulative mortality by main challenge group, day 70 post challenge.
Figure 18:
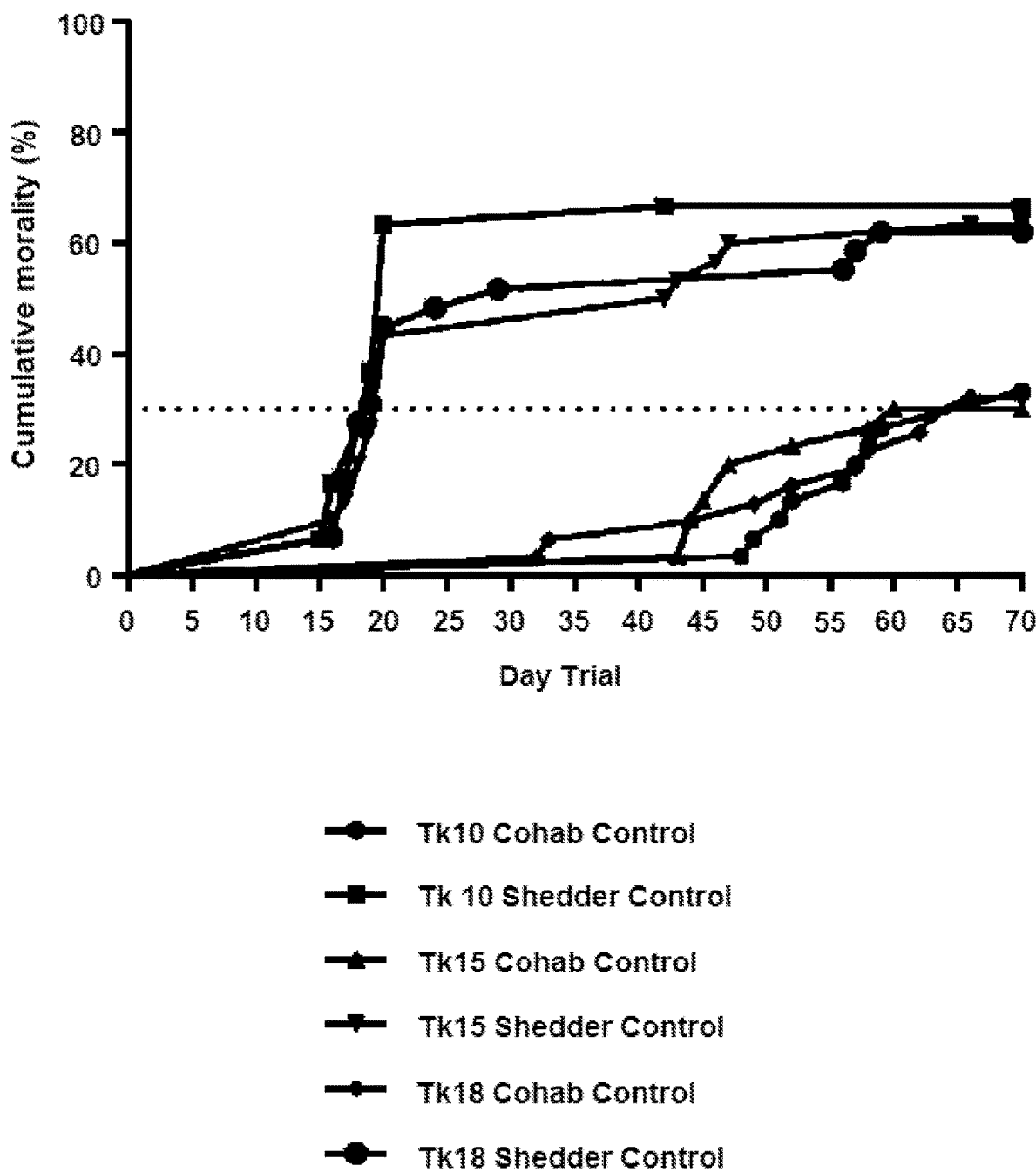
FIG. 18 provides cumulative mortality curves for tank numbers 10, 15 and 18.
Figure 19:
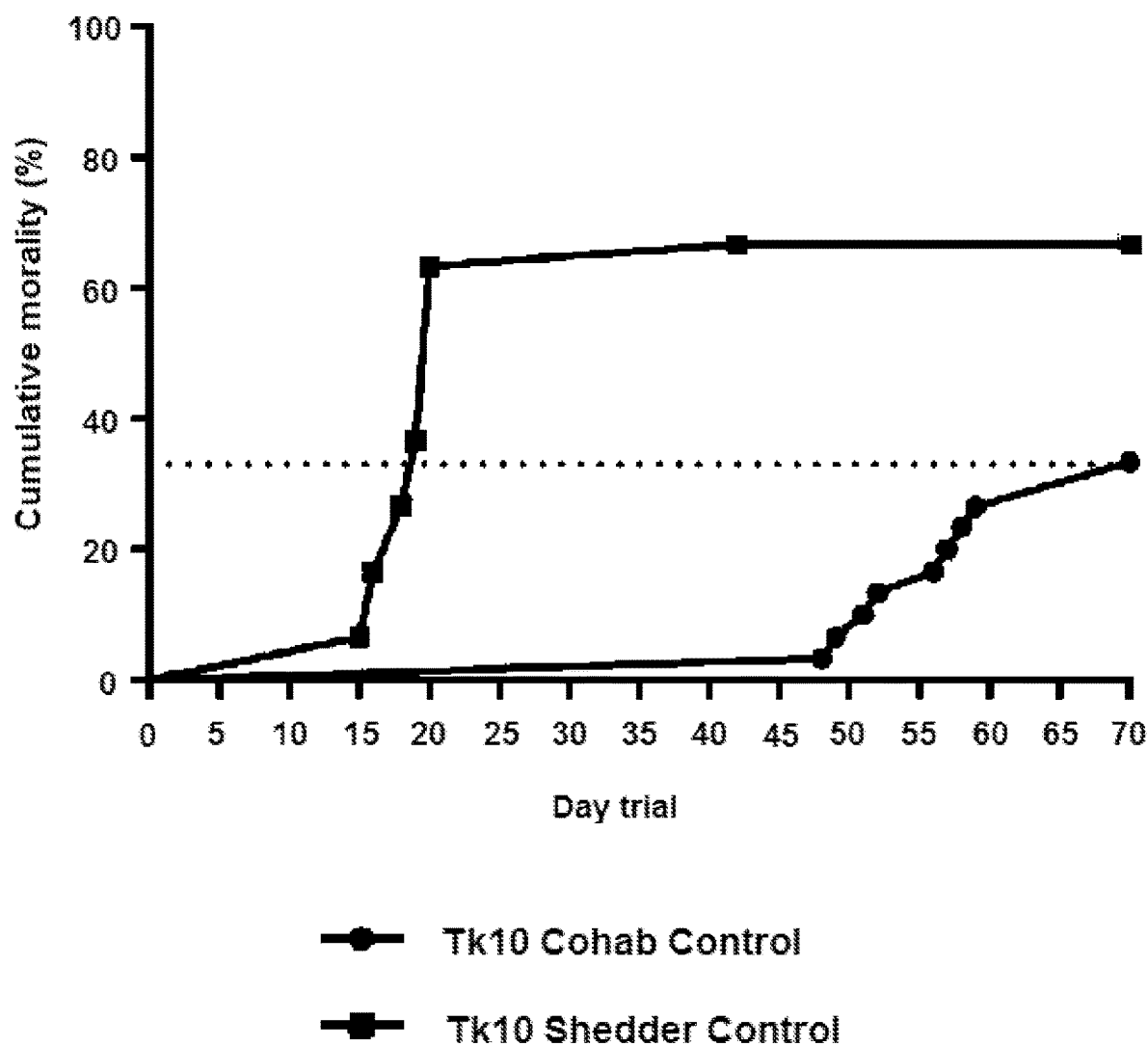
FIG. 19 provides cumulative mortality curves for tank number 10.
Figure 20:
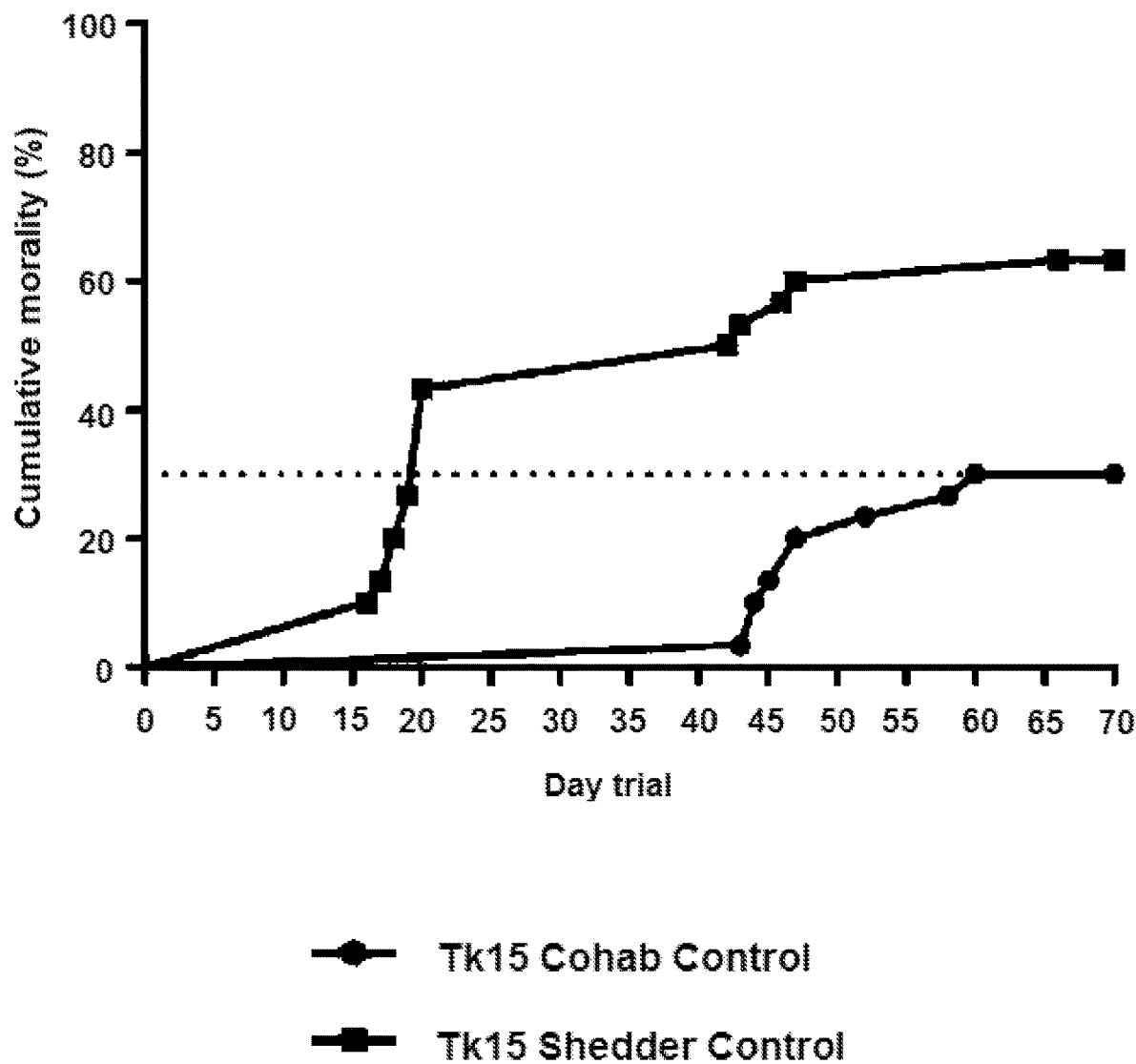
FIG. 20 provides cumulative mortality curves for tank number 15.

Calculations and Parameters to Evaluate:

The fish population was weighed and measured to assess growth performance parameters, such as weight gain percentage (WI), feed conversion rate (FCR), specific growth rate (SGR), rate Specific feed (SFR) and condition factor (K). The cumulative mortality curves were analyzed using the Kaplan-Meier function and statistically evaluated with the Log Rank test, with the GrahPad Prism V6 statistical program. Results are shown in FIG. 16. The effectiveness of the diets was determined by the Relative Percentage Survival (RPS) method (Ellis, 1988).

TABLE

Survival Summary
Comparative Mortality of Shedder and Cohabitant Fish

| Pond N° | | Mortality | | Survival | |
|---|---|---|---|---|---|
| Diet | Group | N° | % | N° | % |
| E 10 | Cohabitant | 8 | 26.7 | 22 | 73.3% |
| Control | Shedder | 20 | 66.7 | 10 | 33.3% |
| E11 | Cohabitant | 3 | 10.0 | 27 | 90.0% |
| Gold 71 | Shedder | 23 | 76.7 | 7 | 23.3% |
| E 12 | Cohabitant | 3 | 10.0 | 27 | 90.0% |
| N-1 | Shedder | 19 | 63.3 | 11 | 36.7% |
| E14 | Cohabitant | 8 | 26.7 | 22 | 73.3% |
| N-1 | Shedder | 26 | 86.7 | 4 | 13.3% |
| E 15 | Cohabitant | 9 | 30.0 | 21 | 70.0% |
| Control | Shedder | 19 | 63.3 | 11 | 36.7% |
| MG | Cohabitant | 3 | 10.0 | 27 | 90.0% |
| N-1 | Shedder | 20 | 66.7 | 10 | 33.3% |
| E 17 | Cohabitant | 6 | 20.0 | 24 | 80.0% |
| Gold 71 | Shedder | 20 | 66.7 | 10 | 33.3% |
| E18 | Cohabitant | 10 | 33.3 | 20 | 70.0% |
| Control | Shedder | 18 | 60.0 | 12 | 36.7% |

*Observation: Pond No. 13 (Gold 71 diet) was not evaluated, due to the incident recorded on day 48 of the trial, where mortality occurred.

Summary of Survival - Mortality by Diet and Challenge

| | | | Mortality | | Survival | | |
|---|---|---|---|---|---|---|---|
| Diet | Group | n | N° | % | N° | % | RPS |
| Control | Cohab | 90 | 27 | 30.0 | 63 | 70 | 100 |
| | Shedder | | 57 | 63.3 | 33 | 37 | |
| Gold 71 | Cohab | *60 | 9 | 15.0 | 51 | 85 | 150 |
| | Shedder | | 43 | 71.7 | 17 | 28 | |
| N-1 | Cohab | 90 | 14 | 15.6 | 76 | 84 | 148 |
| | Shedder | 65 | 72.2 | 25 | 28 | | |

N = starting number of fish in group.
RPS = Relative Percent Survival.
*Gold 71 Tank #1 not included due to oxygen inflow error discussed above.

Comparison between diets/Test Log Rank (Man tel-Cox)

| Diet | Control | Gold 71 | N-1 |
|---|---|---|---|
| Control | = | 0.046 | 0.016 |
| Gold 71 | 0.046 | = | = |
| N-1 | 0.016 | 0.989 | 0.989 |

For each diet in isolation, we compared the results of the different tanks to measure the variance of results for each diet.

Variance of Results Within Each Diet
Test Log Rank (Man tel-Cox)
Tank to Tank comparisons for same diet

| D | Tank | #10 | #11 | #12 | #14 | #15 | #16 | #17 | #18 |
|---|---|---|---|---|---|---|---|---|---|
| C | #10 | = | | | | 0.661 | | | 0.591 |
| | #15 | 0.661 | | | | = | | | 0.862 |
| | #18 | 0.591 | | | | 0.862 | | | = |
| 7 | #11 | | = | | | | | 0.279 | |
| | #17 | | 0.279 | | | | | = | |

| | Variance of Results Within Each Diet Test Log Rank (Mantel-Cox) Tank to Tank comparisons for same diet | | |
|---|---|---|---|
| N | #12 | = 0.184 | 0.972 |
| | #14 | 0.184 = | 0.146 |
| | #16 | 0.972 0.146 | = |

Key:
D = Diet.
C = Control,
7 = Gold 71,
N = N-1.

Cumulative mortality curves for control diet tanks 10, 15 and 18 are provided in FIGS. 18-21. For each chart, the upper curve measures the shredder population, the lower curve measures the cohabitation population. Horizontal dotted line indicates cumulative mortality of cohabitant population at end of study period, showing when the shredder population achieves an equivalent mortality.

Figure 22:
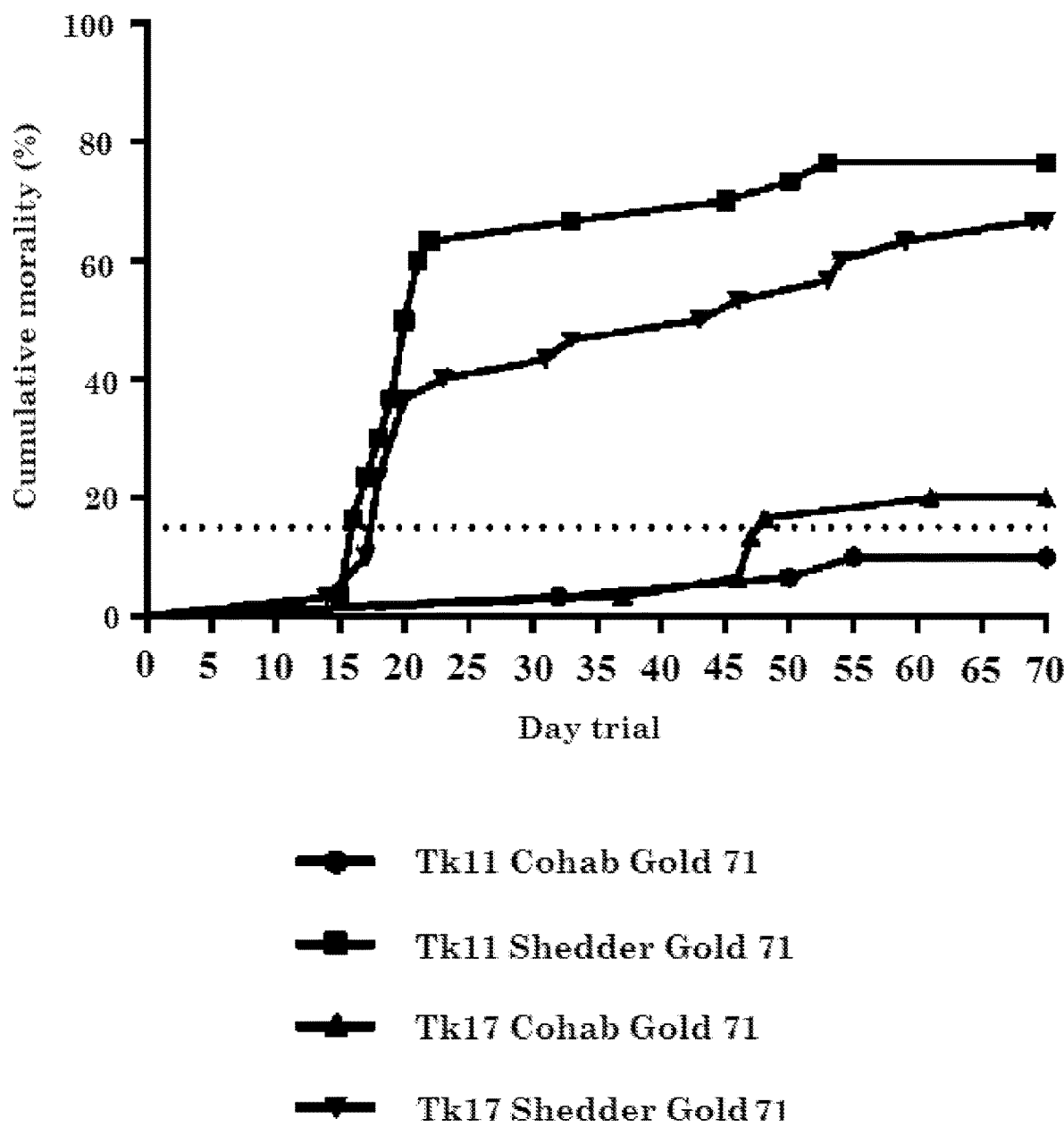
FIG. 22 provides cumulative mortality curves for tank numbers 11, 17.
Figure 23:
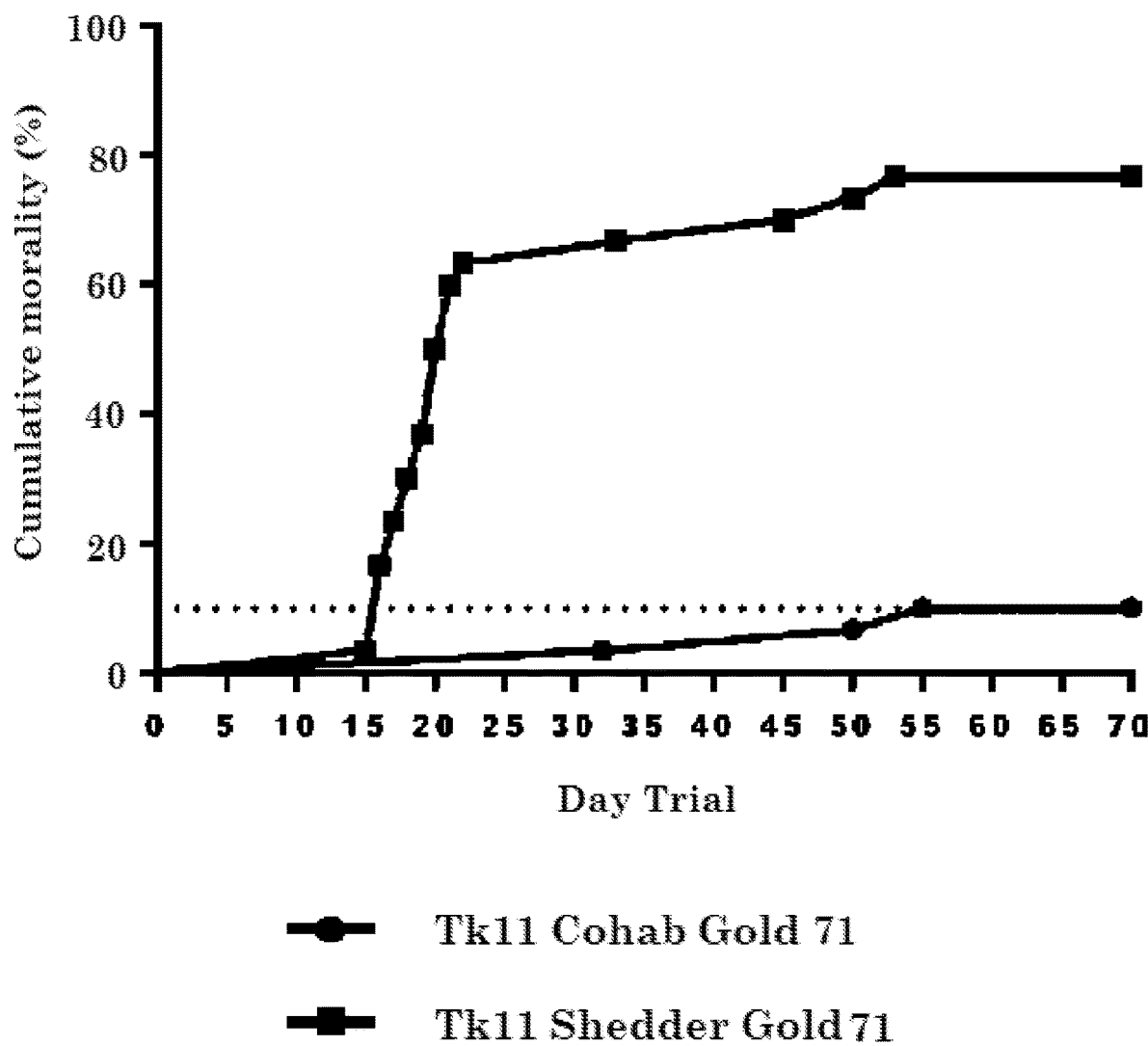
FIG. 23 provides cumulative mortality curves for tank number 11.
Figure 24:
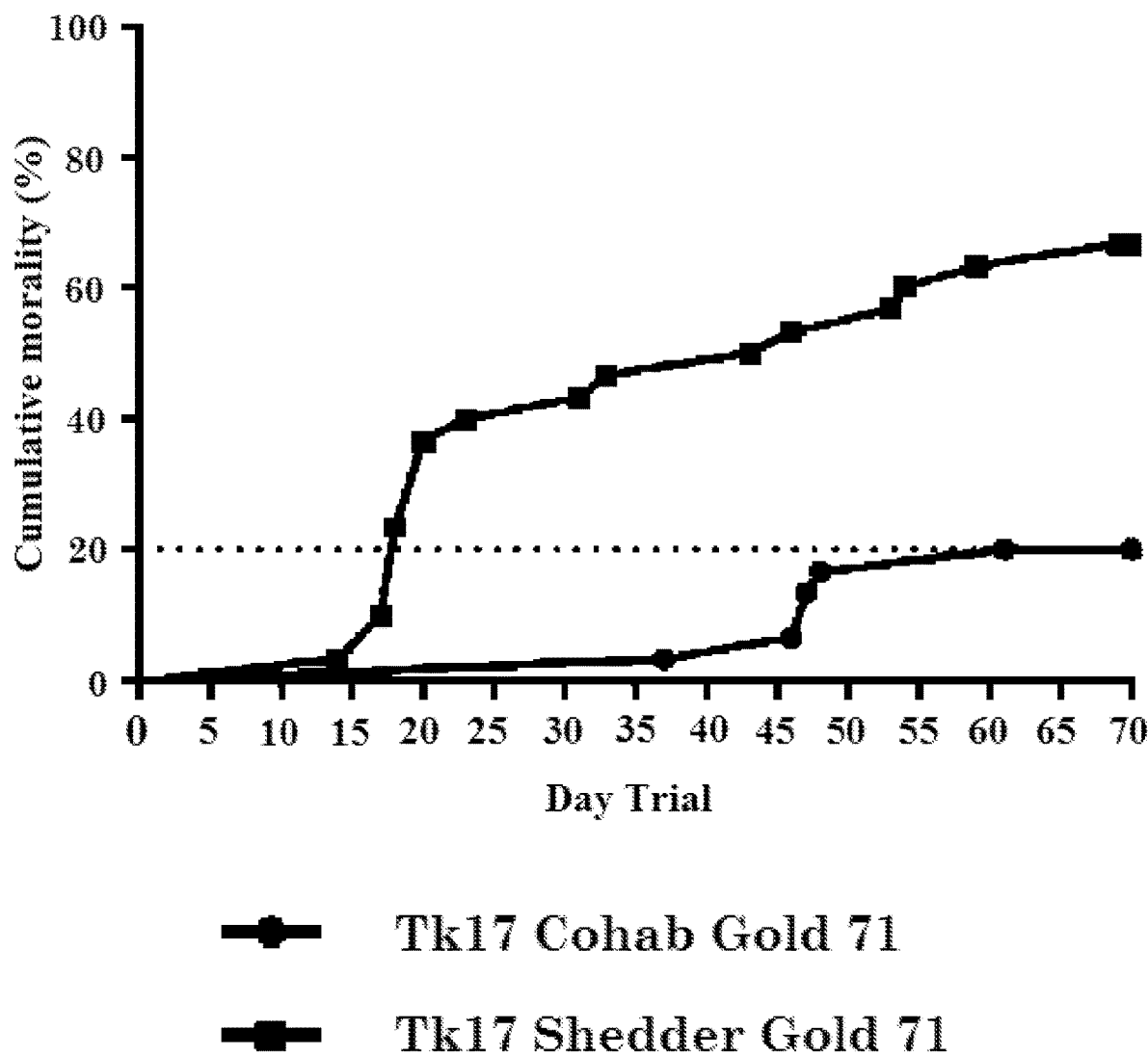
FIG. 24 provides cumulative mortality curves for tank number 17.
Figure 25:
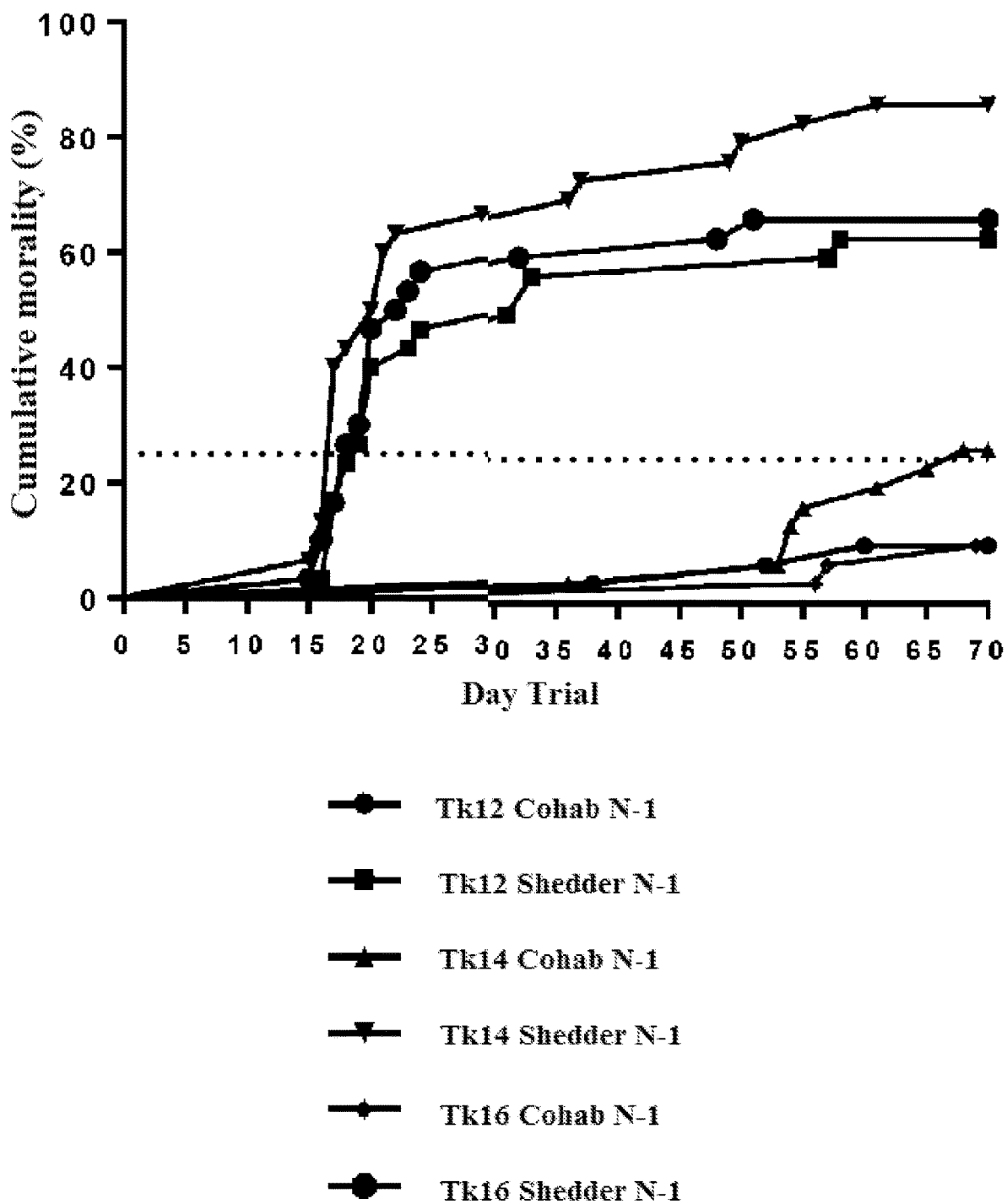
FIG. 25 provides cumulative mortality curves for tank numbers 12, 14, 16.
Figure 26:
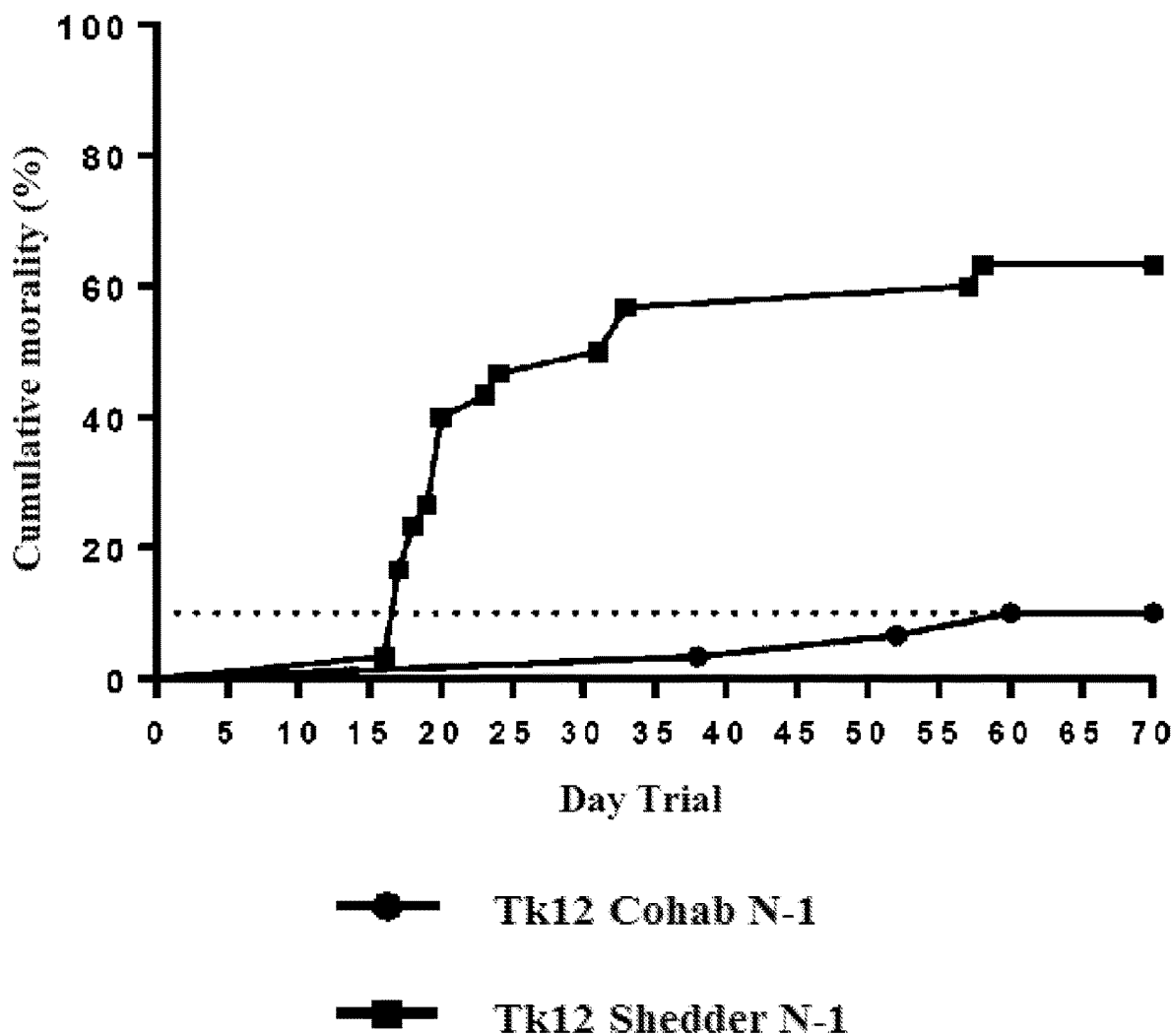
FIG. 26 provides cumulative mortality curves for tank number 12.
Figure 27:
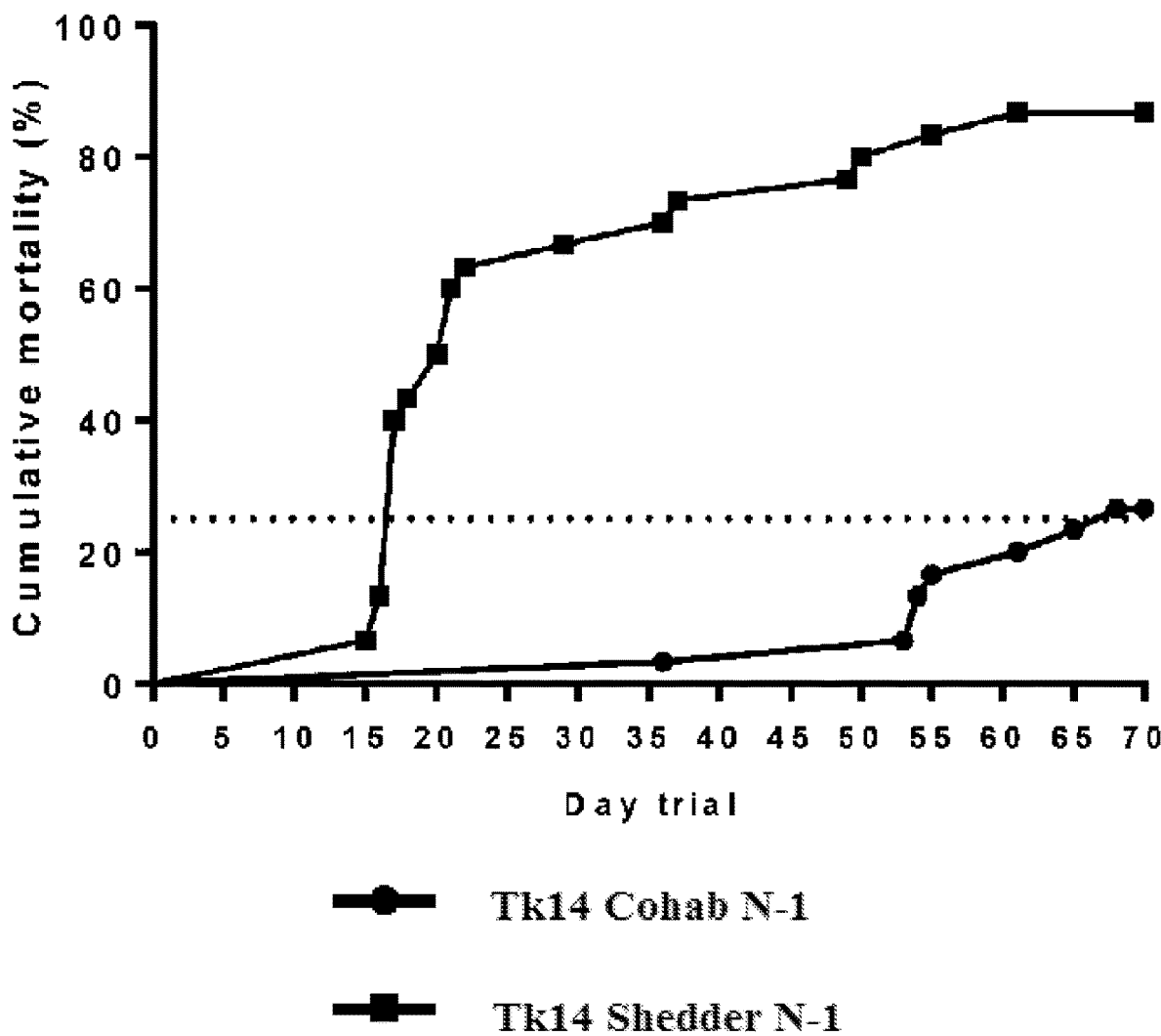
FIG. 27 provides cumulative mortality curves for tank number 14.
Figure 28:
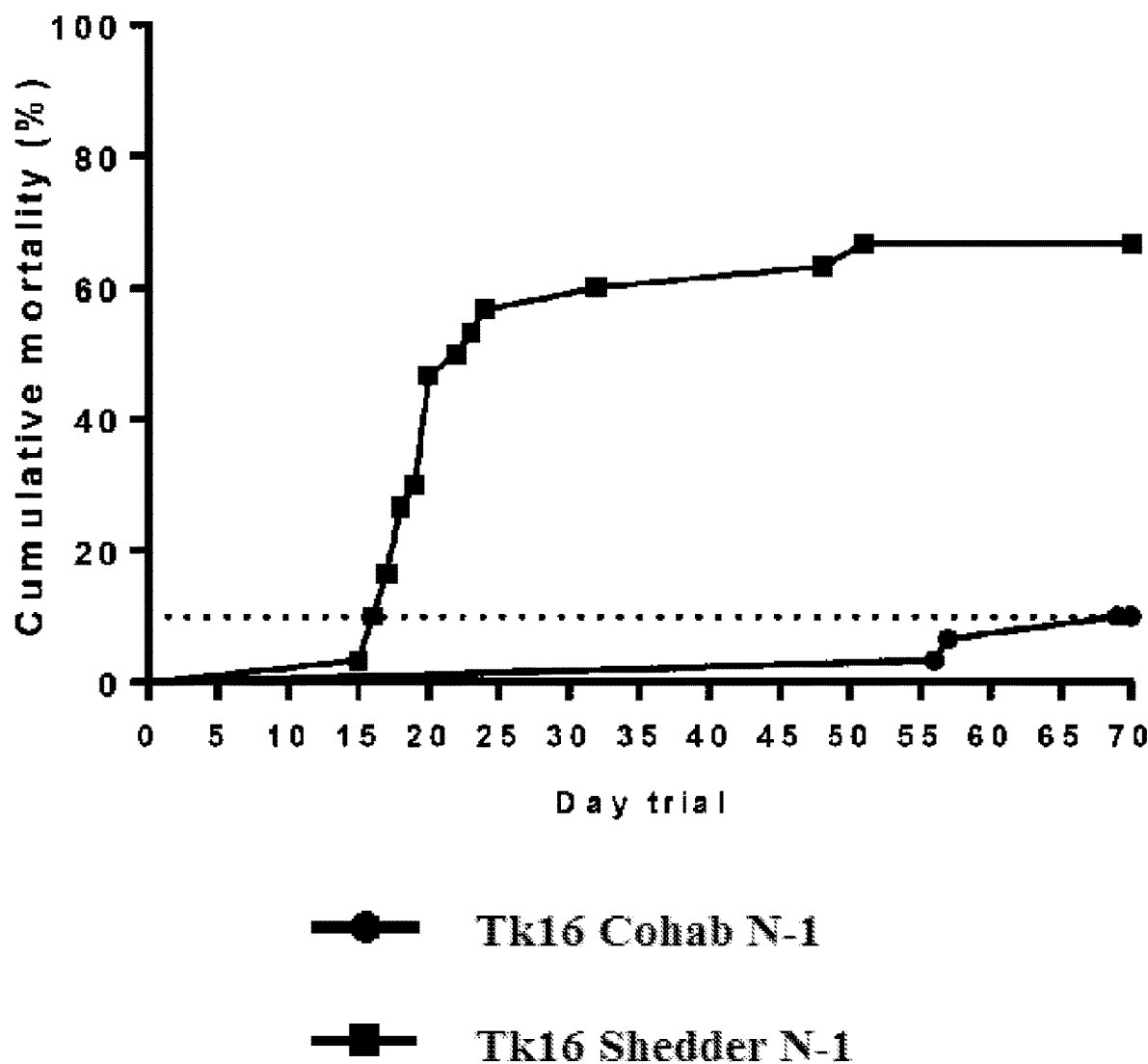
FIG. 28 provides cumulative mortality curves for tank number 16.
Figure 29:
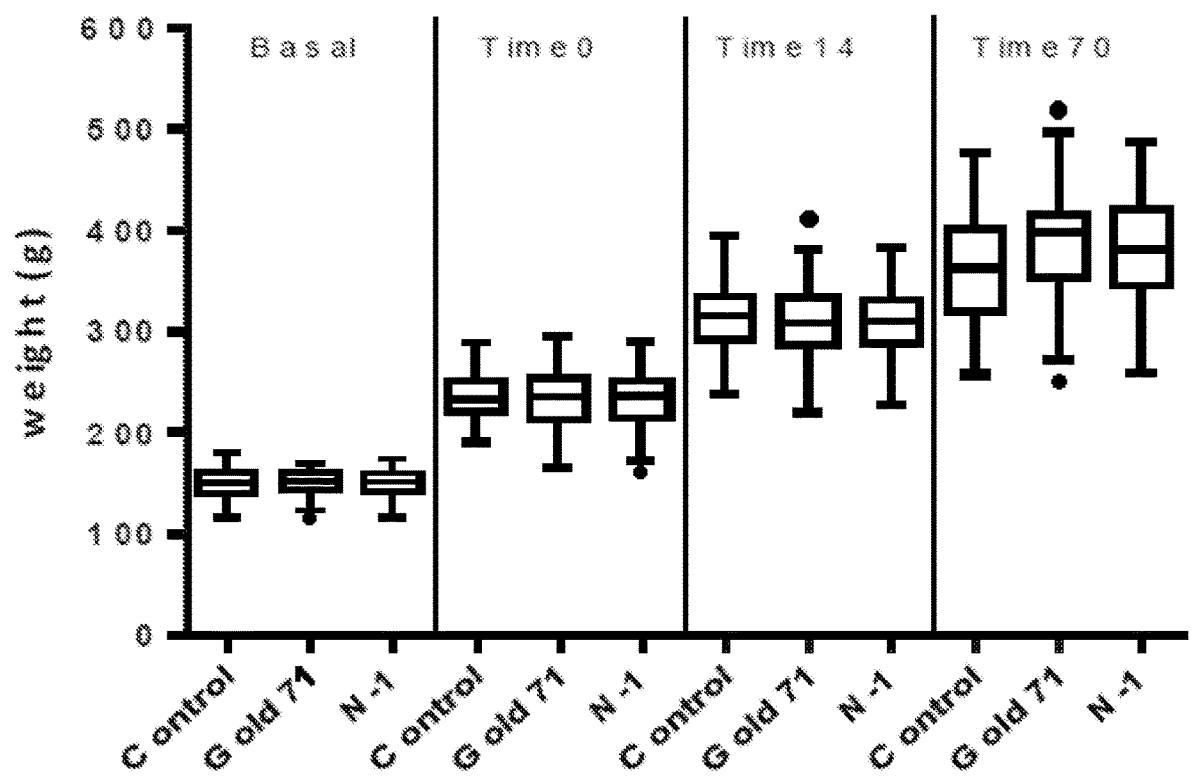
FIG. 29 provides a summary of weight samples by diet/stage of the study.
Figure 30:
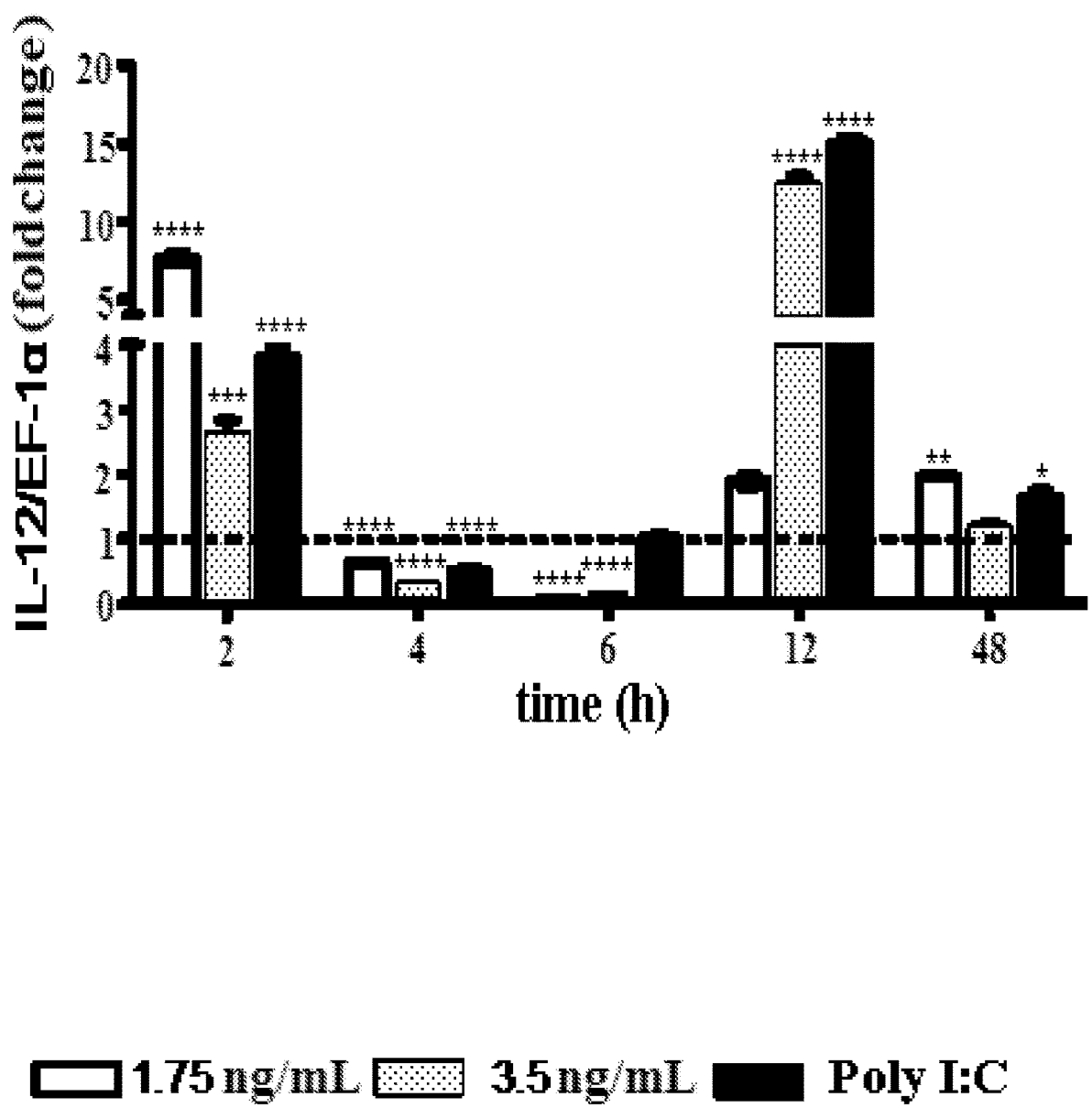
FIG. 30 shows the kinetics expression analysis of il-10, il-12 and ifn-I transcripts in SHK-1 cells pre-incubated with NC 1.75 and 3.5 ng/mL. Data are shown as fold change of mRNA for each gene compared to non-stimulated control cells, standardized for the housekeeping gene ef-1α and presented as measurements±standard error for each well in triplicate. As positive control, Poly I:C (Commercially available from Sigma-Aldrich division of Milipore, Catalog No. P9582) was used. Asterisks indicate statistically-significant differences between the means and the control without treatments and analyzed with Sidak multiple comparison test (*$p<0.05$, $p<0.01$ and *$p<0.001$, segmented line correspond at control without treatment).
Figure 31:
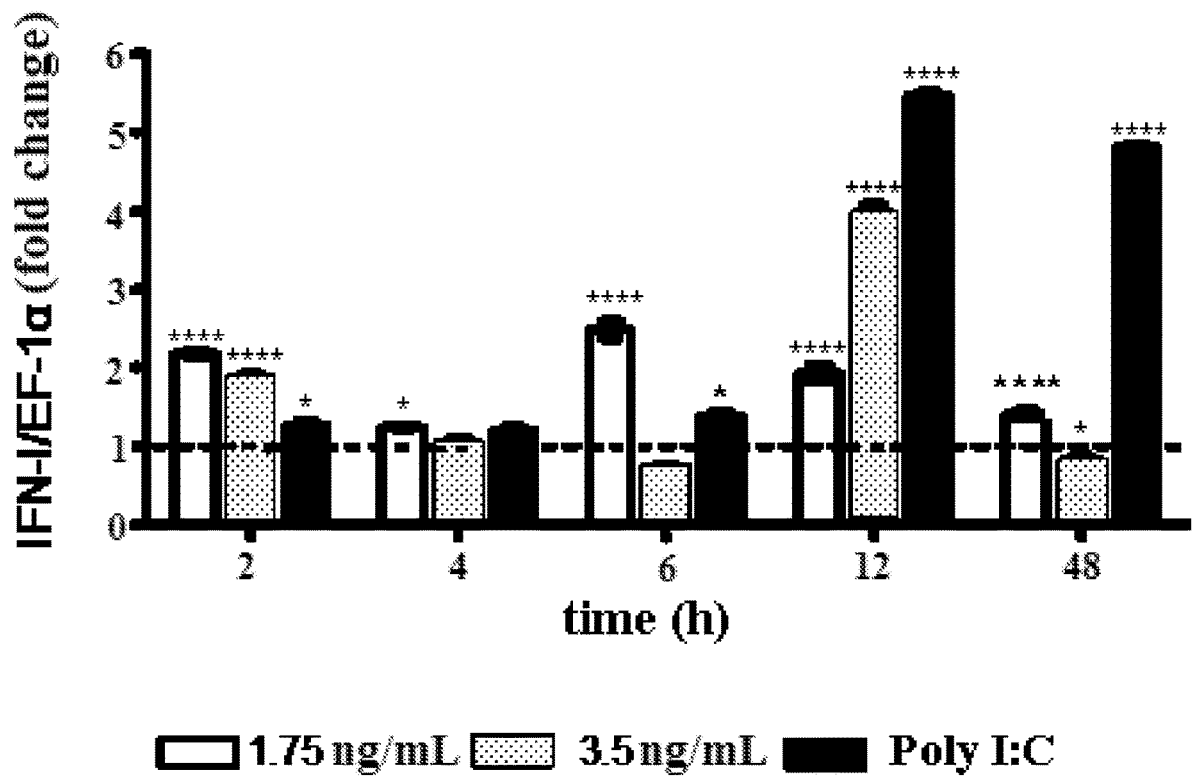
FIG. 31 shows the kinetics expression analysis of il-10, il-12 and ifn-I transcripts in SHK-1 cells pre-incubated with NC 1.75 and 3.5 ng/mL. Data are shown as fold change of mRNA for each gene compared to non-stimulated control cells, standardized for the housekeeping gene ef-1α and presented as measurements±standard error for each well in triplicate. As positive control, Poly I:C (Commercially available from Sigma-Aldrich division of Milipore, Catalog No. P9582) was used. Asterisks indicate statistically-significant differences between the means and the control without treatments and analyzed with Sidak multiple comparison test (*$p<0.05$, $p<0.01$ and *$p<0.001$, segmented line correspond at control without treatment).
Figure 32:
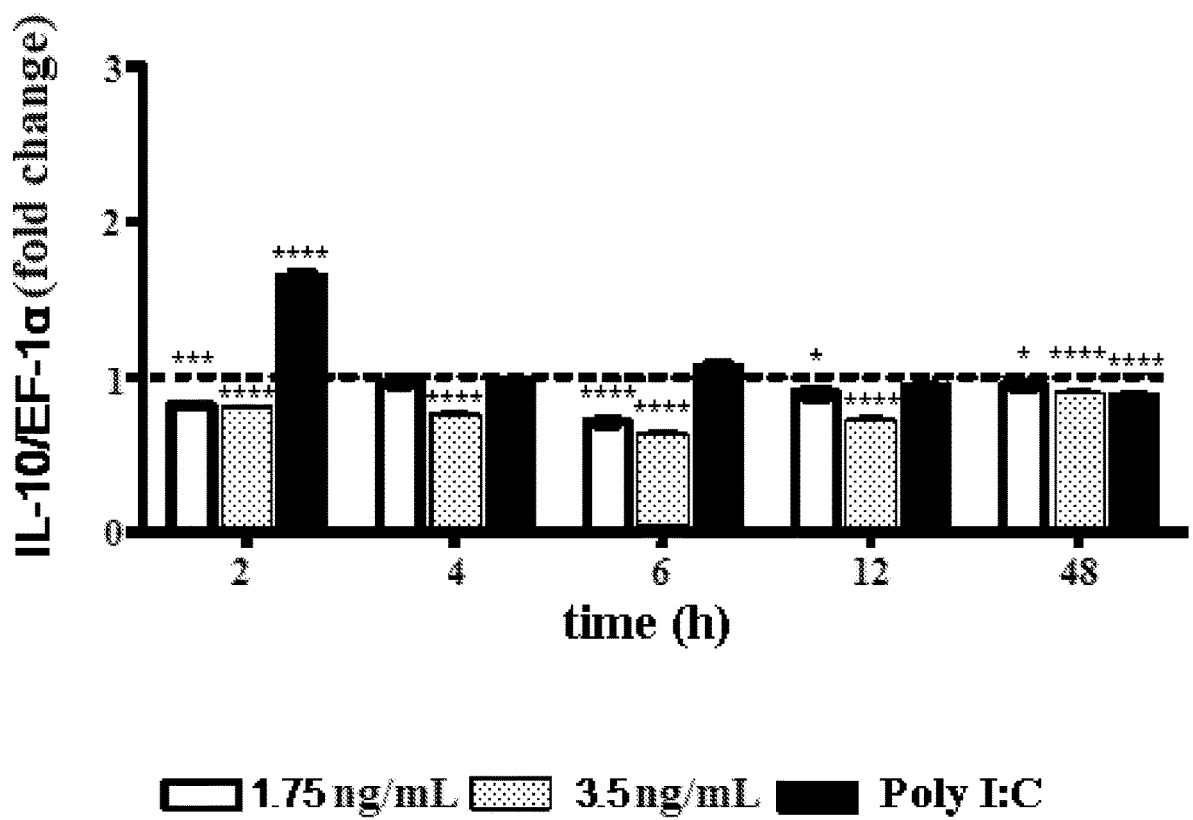
FIG. 32 shows the kinetics expression analysis of il-10, il-12 and ifn-I transcripts in SHK-1 cells pre-incubated with NC 1.75 and 3.5 ng/mL. Data are shown as fold change of mRNA for each gene compared to non-stimulated control cells, standardized for the housekeeping gene ef-1α and presented as measurements±standard error for each well in triplicate. As positive control, Poly I:C (Commercially available from Sigma-Aldrich division of Milipore, Catalog No. P9582) was used. Asterisks indicate statistically-significant differences between the means and the control without treatments and analyzed with Sidak multiple comparison test (*$p<0.05$, $p<0.01$ and *$p<0.001$, segmented line correspond at control without treatment).
Figure 33:
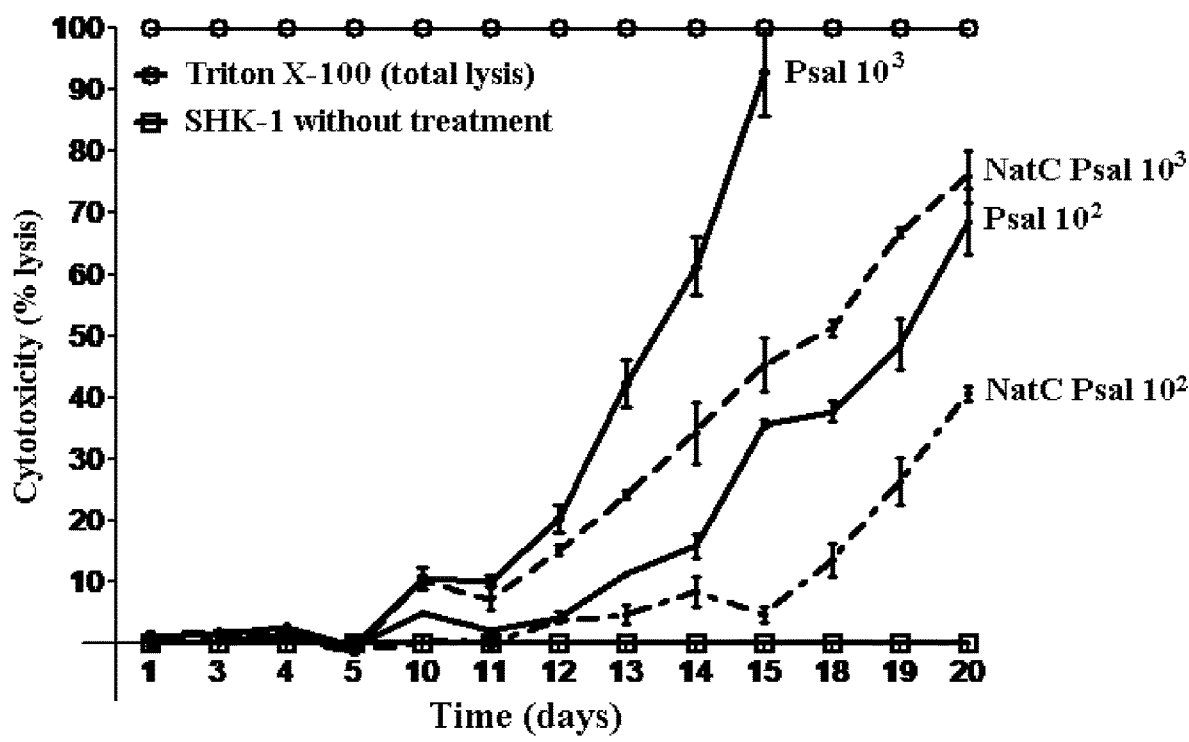
FIG. 33 shows results of a cytotoxicity assay in SHK-1 cells with NC treatment on infected SHK-1 cells culture supernatants. SHK-1 cells were incubated with NC 3.5 ng/mL for 12 h previously and after challenge with *P. salmonis* at $10^2$ and $10^3$ bacteria/mL respectively. Supernatant samples were taken in the corresponding days to measure LDH activity. The results are presented as the percentage of cytotoxicity evaluated as the LDH activity, and are presented as means±standard error of each well in triplicated. Control: corresponds to untreated cells (without NC).
Figure 34:
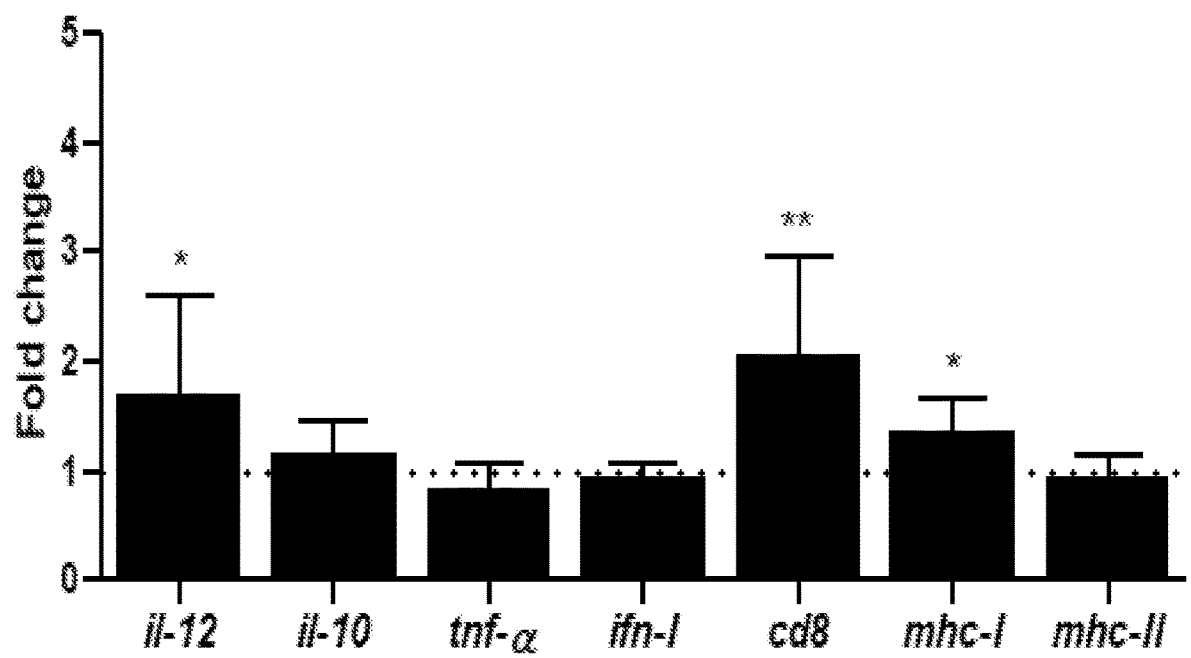
FIG. 34 results for the gene expression profile of immune markers in head kidney of fish fed with NC-supplemented diet. Head kidney was obtained for expression analysis of interleukin-12 (il-12), interleukin-10 (il-10), tumor necrosis factor-α (tnf-α), interferon I (ifn-I), cd8, class I major histocompatibility complex-related protein (mhc-I) and class II major histocompatibility complex-related protein (mhc-II) and by RT-qPCR. Graphs depict average fold change of expression using the control group (dotted line) as calibrator and the mRNA of ef-1α as normalizer. Asterisks depict statistically-significant differences calculated with the Sidak multiple comparison test ($p<0.05$; $p<0.01$, *$p<0.001$, ****$p<0.0001$, segmented line correspond at control without treatment).
Figure 35:
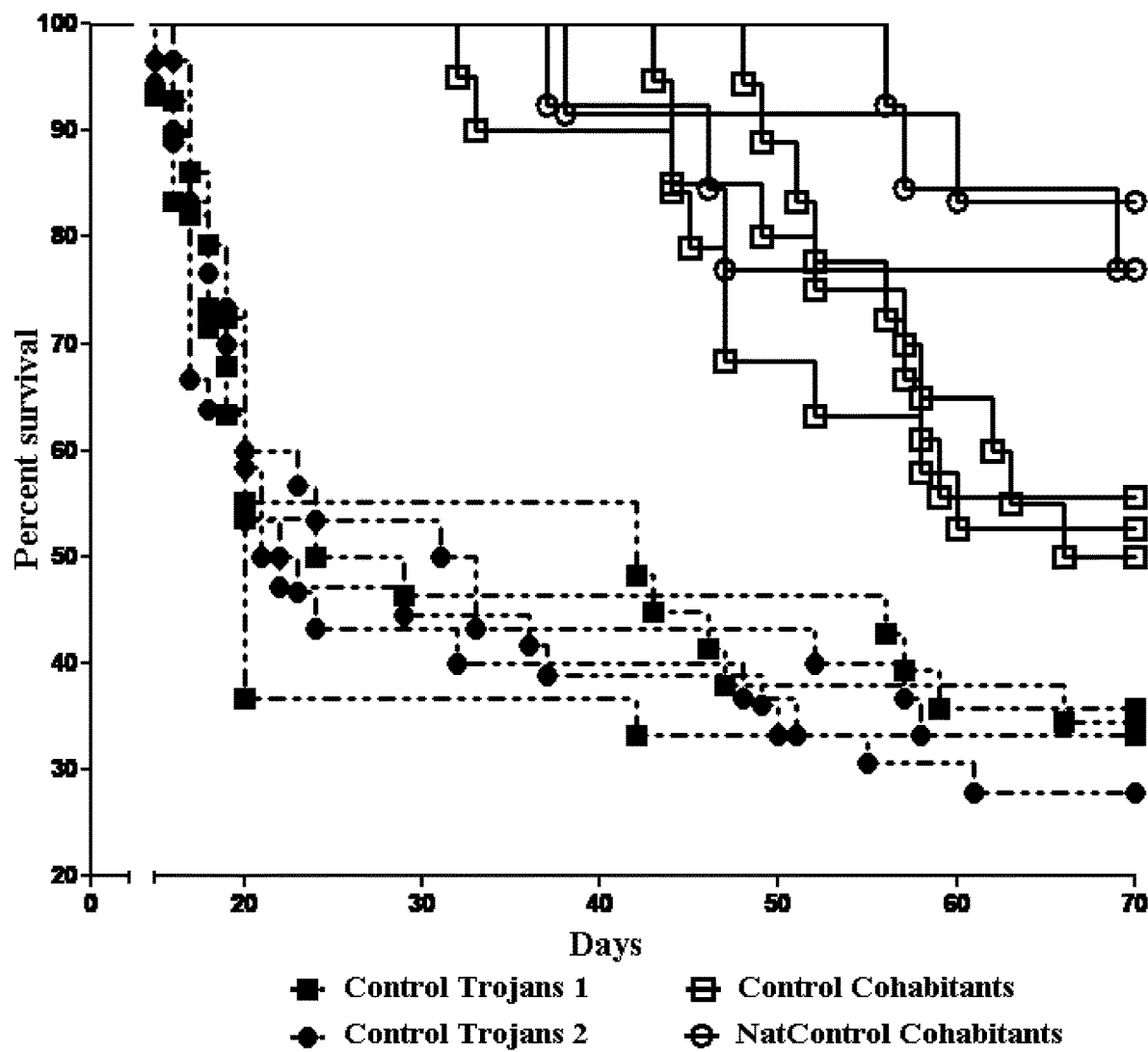
FIG. 35 illustrates the percentage of survival in shedders (fish injected intraperitoneally with *Piscirickettsia salmonis*, and thus presenting a contagious individual; control Shedders 1 and 2, black and gray dashed lines), allocated in tanks containing control co-habitants fish fed without NC supplementation (Control non-infected cohabitants, gray lines) and co-habitants fish fed with NC diet (NC cohabitant, black lines).
Figure 36:
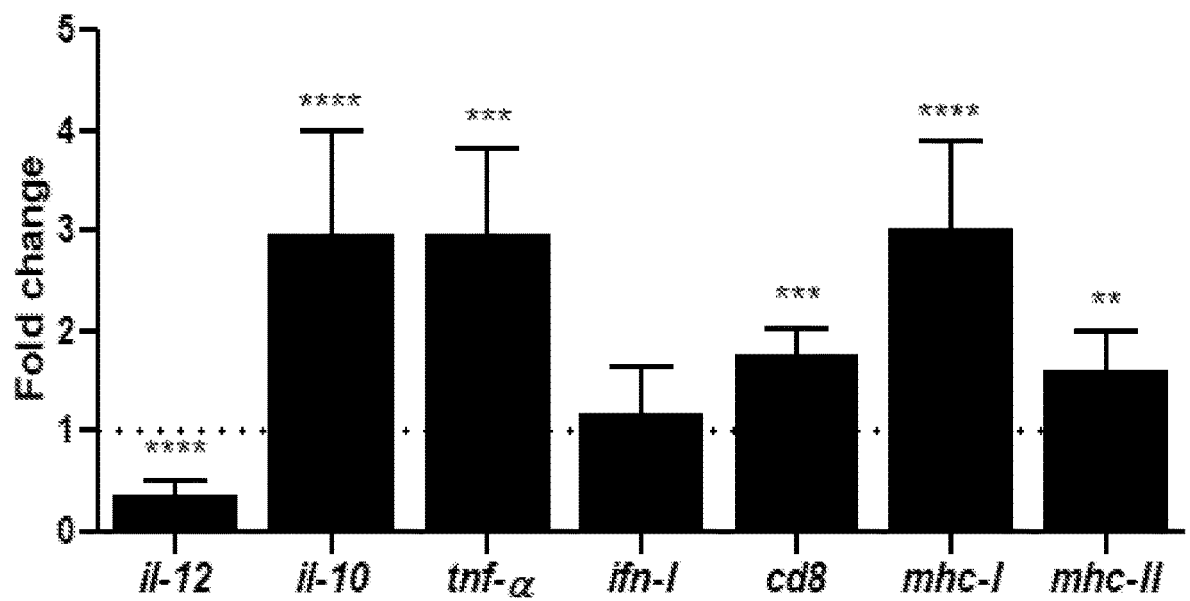
FIG. 36 measures the gene expression profile of immune markers in head kidney of fish fed with NC-supplemented diet and survivor to challenge with *P. salmonis*. The head kidney of survivor fish was obtained for gene expression analysis of interleukin-12 (il-12), interleukin-10 (il-10), tumor necrosis factor-α (tnf-α), interferon I (ifn-I), cd8, class I major histocompatibility complex-related protein (mhc-I) and class II major histocompatibility complex-related protein (mhc-II), and by RT-qPCR. Graphs depict average fold change of expression using the control group (dotted line) as calibrator and the mRNA of ef-1α as normalizer. Asterisks depict statistically-significant differences calculated with the Sidak multiple comparison test (*$p<0.05$; $p<0.01$, *$P<0.001$, ****$p<0,0001$, segmented line correspond at control without treatment).

FIGS. 22-24 provides cumulative mortality curves for Gold 71 diet tanks. For each chart, the upper curve measures the shredder population, the lower curve measures the cohabitation population.

FIGS. 25-28 provides cumulative mortality curves for N-1 diet tanks. For each chart, the upper curve measures the shredder population, the lower curve measures the cohabitation population. Horizontal dotted line indicates cumulative mortality of cohabitant population at end of study period, showing when the shredder population achieves an equivalent mortality.

The Gold 71 diet achieved a Hazard Ratio of 44% (95% confidence interval=23%-86%) viz the control diet. That is, the probability of dying with Gold 71 diet was 56% lower than the control group. The N-1 diet achieved a Hazard Ratio of 40% (95% confidence interval=21%-74%) viz the control diet. That is, the probability of dying with N-1 diet was 60% lower than the control group.

| | | Comparison mortality per replicates of each diet Log Rank (Mantel-Cox) | | | | | | | |
|---|---|---|---|---|---|---|---|---|---|
| D | Tank | #10 Sig. | #11 Sig. | #12 Sig. | 14 Sig. | 15 Sig. | 16 Sig. | 17 Sig. | 18 Sig. |
| C | #10 | = | 0.113 | 0.099 | 0.734 | 0.661 | 0.084 | 0.647 | 0.591 |
| 7 | #11 | 0.113 | = | 0.983 | 0.189 | 0.056 | 0.949 | 0.279 | 0.034 |
| N | #12 | 0.099 | 0.983 | = | 0.184 | 0.053 | 0.972 | 0.274 | 0.031 |
| N | #14 | 0.734 | 0.189 | 0.184 | = | 0.473 | 0.146 | 0.841 | 0.381 |
| C | #15 | 0.661 | 0.056 | 0.053 | 0.473 | = | 0.043 | 0.365 | 0.862 |
| N | #16 | 0.084 | 0.949 | 0.972 | 0.146 | 0.043 | = | 0.248 | 0.025 |
| 7 | #17 | 0.647 | 0.279 | 0.274 | 0.841 | 0.365 | 0.248 | = | 0.286 |
| C | #18 | 0.591 | 0.034 | 0.031 | 0.381 | 0.862 | 0.025 | 0.286 | = |

Key:
D = Diet.
C = Control,
7 = Gold 71,
N = N-1.

Figure 21:
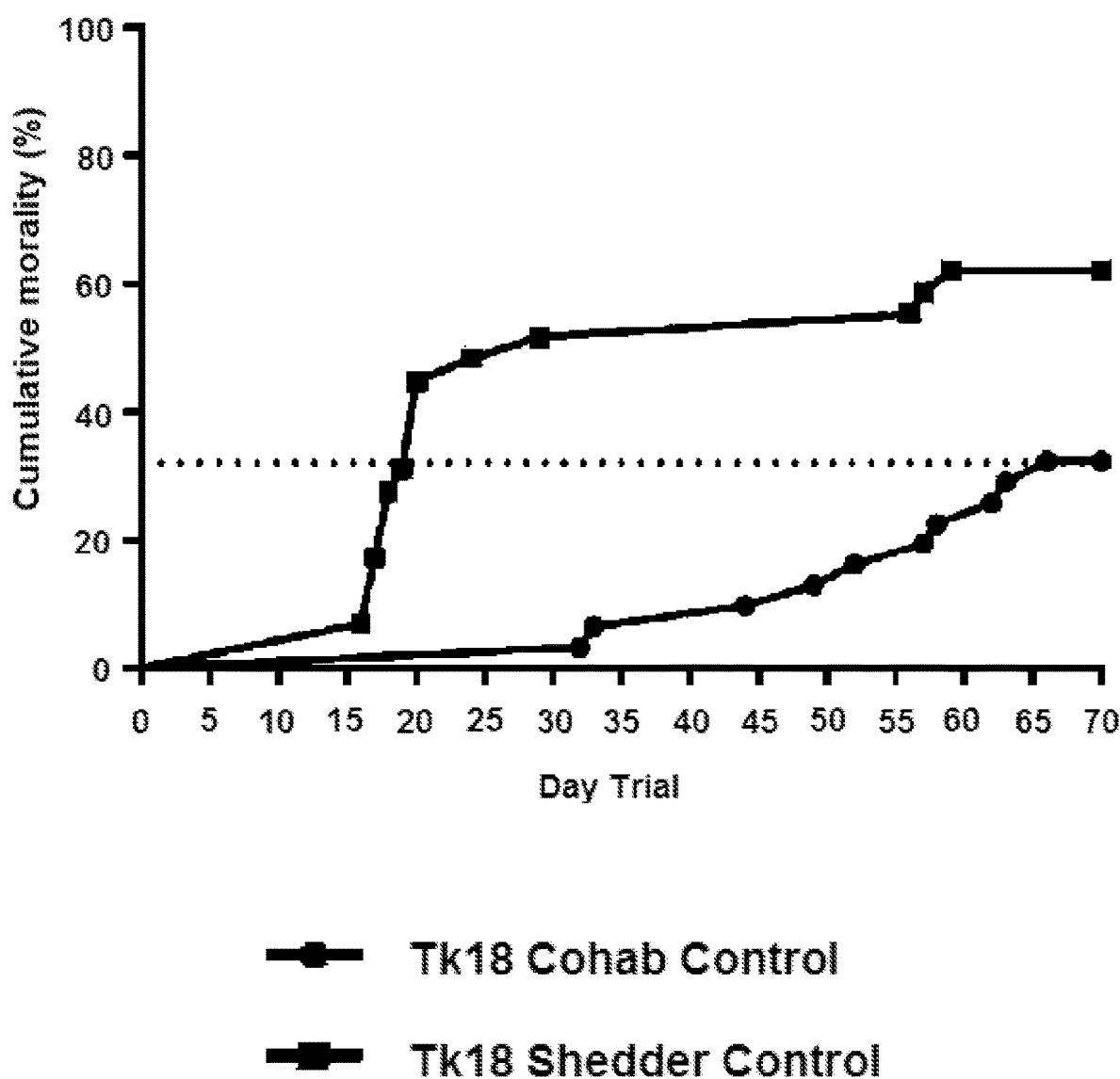
FIG. 21 provides cumulative mortality curves for tank number 18.

Each experimental produced greater weight gain than did the industry-standard control diet. FIG. 21 provides a summary of weight samples by diet/stage of the study.

| | Sampling Basal | | | Time 0 | | | Time 14 | | | Time 70 | | |
|---|---|---|---|---|---|---|---|---|---|---|---|---|
| | Ctl | Gold | N-1 | Ctl | Gold | N-1 | Ctl | Gold | N-1 | Ctl | Gold | N-1 |
| n | 105 | 105 | 105 | 105 | 105 | 105 | 105 | 105 | 105 | 63 | 51 | 76 |
| Min | 116 | 116 | 116 | 190,1 | 164.1 | 160 | 237.2 | 219.2 | 228.5 | 257.6 | 251 | 258 |
| 25% | 138.9 | 142.2 | 141.4 | 219 | 211.8 | 214.3 | 291.3 | 284.7 | 288.1 | 320 | 353 | 345.4 |
| ñ | 148.2 | 150.9 | 150.6 | 230.8 | 233.9 | 236.4 | 314.2 | 306 | 310.3 | 362.8 | 397.6 | 381 |
| 75% | 159 | 158.9 | 158.8 | 248.5 | 252.3 | 250 | 333.7 | 332 | 330.9 | 402.6 | 416.6 | 421.6 |
| Max | 177 | 168 | 172 | 287.2 | 294.2 | 289 | 393.3 | 412 | 381 | 476 | 518.8 | 487.2 |
| CoV | 9.11 | 7.94 | 8.57 | 8.92 | 11.92 | 10.84 | 9.65 | 11.84 | 10.59 | 14.34 | 13.87 | 12.07 |
| µ | 147.4 | 148.9 | 148.8 | 232.6 | 230.7 | 231.8 | 312.6 | 308.1 | 309 | 363.1 | 386.4 | 381.7 |
| σ | 13.43 | 11.83 | 12.75 | 20.74 | 27.5 | 25.13 | 30.17 | 36.48 | 32.72 | 52.09 | 53.58 | 46.07 |
| εµ | 1.311 | 1.154 | 1.244 | 2.024 | 2.683 | 2.453 | 2.944 | 3.561 | 3.193 | 6.563 | 7.503 | 5.285 |
| µ(L95) | 144.8 | 146.6 | 146.4 | 228.6 | 225.4 | 226.9 | 306.7 | 301 | 302.6 | 350 | 371.4 | 371.1 |
| µ(U95) | 150 | 151.2 | 151.3 | 236.7 | 236 | 236.7 | 318.4 | 315.1 | 315.3 | 376.2 | 401.5 | 392.2 |
| ñ(L95) | 144.2 | 145.4 | 147.4 | 224.5 | 223.9 | 224.3 | 302 | 298.4 | 301.4 | 350.8 | 375 | 368.6 |
| ñ(U95) | 152 | 154.4 | 154 | 238.1 | 241.3 | 241 | 320.4 | 315.2 | 320 | 375.4 | 405 | 397.4 |

Key:
Cl1 = Control diet,
Gold = Gold 71 diet
N = Number of values,
Min = Minimum value.
25% = 25$^{th}$ Percentile.
ñ = Median.
75% = 75$^{th}$ Percentile.
Max = Maximum value.
CoV = Coefficient of variation (in percent).
µ = Mean.
σ = Std. Deviation.
εµ = Std. Error of Mean.
µ(L95) = Lower 95% CI of mean.
µ(U95) = Upper 95% CI of mean.
ñ(L95) = Lower 95% CI of median.
ñ(U95) = Upper 95% CI of median Cumulative mortality: During the trial the Shedder group had a cumulative mortality of 68.7%, starting the outbreak at day 8 post-challenge and stabilizing on day 24th. Due to this shedder mortality the cohabitants of control group reach a cumulative mortality of 30% at day 70 of trial.

The start of mortality in the shedder group occurred between 8 and 15 days after the inoculation, and for the cohabitant control group the outbreak occurs between days 32 and 43. For cohabitant of Gold 71 and N1 diet the SRS outbreak was registered between days 32 and 46 days, and 36 to 52 post inoculation respectively. Diet N1 was the one that resisted better the start of the outbreak, with 9 days of difference with control group and 6 days with Gold diet 71.

At the end of the challenge was possible to see some level of protection in the two evaluated diets. Both diets, Gold 71 and N1 obtained an average cumulative mortality of 15 and 15.4% respectively (see table). Also was possible to see that diets replicates do not differed significantly within groups (see table), but in both cases significant differences were observed with respect to the control diet (p value of 0.046 and 0.016 respectively).

When evaluating the relative percentage of survival (RPS) in the Gold 71 and N1 diets (see table), it was observed that they obtained similar values of 50 and 48.1 respectively, that is to say that they improve the survival by ~50% with respect to fish fed a control diet.

At evaluation, the protection measure of each diet (Hazard Ratio, CI 95%) shows that it can be observed that the N-1 diet reduces a 60% the probability of dying in the cohabitant group, and diet Gold 71 reduces the probability of death by 56%.

Productivity Parameters:

During the experimental feeding period, not significant differences were observed in the productive parameters, registering similar growths during the 14 days of evaluation (see table). During the SRS challenge, the productive results was deficient, being diet Gold 71 which obtained the best conversion and growth factor, followed by the N1 diet, being control diet the one with the lowest results. The results were maintained when evaluating with and without tank 13 Diet Gold 71, sinistered on day 48 post challenge (see tables).

| Productive parameters during experimental feeding period (14d) | | | | | | | | | | |
|---|---|---|---|---|---|---|---|---|---|---|
| D | Tk | $gms_0$ | $n_0$ | $g_{14}$ | $n_{14}$ | x | $\Delta gms$ | FCR | % SGR | TGC | % SFR |
| C | 10 | 233.3 | 35 | 311.9 | 30 | 5 | 33.7% | 0.78 | 2.07 | 2.99 | 1.62 |
| 7 | 11 | 229.8 | 35 | 301.8 | 30 | 5 | 31.3% | 0.78 | 1.95 | 2.79 | 1.52 |
| N | 12 | 230.8 | 35 | 306.6 | 30 | 5 | 32.8% | 0.75 | 2.03 | 2.91 | 1.53 |
| 7 | 13 | 226.5 | 35 | 308.6 | 30 | 5 | 36.2% | 0.70 | 2.21 | 3.16 | 1.54 |
| N | 14 | 229.8 | 35 | 308.3 | 30 | 5 | 34.1% | 0.73 | 2.10 | 3.01 | 1.53 |
| C | 15 | 232.5 | 35 | 308.2 | 30 | 5 | 32.5% | 0.75 | 2.01 | 2.89 | 1.51 |
| N | 16 | 234.8 | 35 | 312.1 | 30 | 5 | 32.9% | 0.75 | 2.03 | 2.94 | 1.52 |
| 7 | 17 | 235.9 | 35 | 313.8 | 30 | 5 | 33.0% | 0.76 | 2.04 | 2.95 | 1.54 |
| C | 18 | 232.1 | 35 | 317.7 | 30 | 5 | 36.9% | 0.65 | 2.24 | 3.24 | 1.46 |

Key:
D = Diet.
C = Control, N = N-1, 7 = Gold 71.
Tk = tank number.
$gms_0$ = average fish weight (grams) at time = 0.
$n_0$ = number of fish at t = 0.
$g_{14}$ = average fish weight (grams) at time = 14.
$n_{14}$ = number of fish at t = 14.
x = number of sampling.
$\Delta gms$ = change in average fish weight (in percent).
FCR = Food Conversion Ratio at end.
Mortality at end was zero for each tank.

After 70 days, the productivity of the various tanks was as follows:

| Productive parameters during Challenge *P. salmortis* (70d) | | | | | | | | | | | |
|---|---|---|---|---|---|---|---|---|---|---|---|
| D | Tk | $gms_0$ | $n_0$ | $g_{70}$ | ✝ | S | $\Delta gms$ | FCR | SGR % | TGC | SFR % |
| C | 10 | 311.9 | 30.0 | 373.2 | 26.7 | 73.3 | 19.7 | 7.22 | 0.19 | 0.36 | 1.35 |
|   |    | 344.4 | 30.0 | 357.5 | 66.7 | 33.3 | 3.8 |      |      |      |      |
| 7 | 11 | 301.8 | 30.0 | 382.8 | 10.0 | 90.0 | 26.8 | 4.92 | 0.27 | 0.48 | 1.32 |
|   |    | 354.7 | 30.0 | 390.1 | 76.7 | 23.3 | 10.0 |     |      |      |      |
| N | 12 | 306.6 | 30.0 | 386.9 | 10.0 | 90.0 | 26.2 | 4.72 | 0.26 | 0.47 | 1.21 |
|   |    | 345.6 | 30.0 | 373.5 | 63.3 | 36.7 | 8.1 |      |      |      |      |
| 7* | 13 | 308.6 | 30.0 | 381.1 | 10.0 | 90.0 | 23.5 | 3.90 | 0.22 | 0.42 | 0.88 |
|   |    | 360.2 | 30.0 | 381.6 | 70.0 | 30.0 | 6.0 |      |      |      |      |
| N | 14 | 308.3 | 30.0 | 390.8 | 26.7 | 73.3 | 26.8 | 5.28 | 0.28 | 0.48 | 1.45 |
|   |    | 352.5 | 30.0 | 393.5 | 86.7 | 13.3 | 11.6 |     |      |      |      |
| C | 15 | 308.2 | 30.0 | 341.2 | 30.0 | 70.0 | 10.7 | 7.27 | 0.14 | 0.20 | 1.03 |
|   |    | 344.8 | 30.0 | 378.7 | 63.3 | 36.7 | 9.8 |      |      |      |      |
| N | 16 | 312.1 | 30.0 | 369.0 | 10.0 | 90.0 | 18.2 | 5.68 | 0.23 | 0.34 | 1.33 |
|   |    | 361.7 | 30.0 | 422.9 | 66.7 | 33.3 | 16.9 |     |      |      |      |
| 7 | 17 | 313.8 | 30.0 | 390.5 | 20.0 | 80.0 | 24.4 | 4.34 | 0.26 | 0.44 | 1.11 |
|   |    | 356.5 | 30.0 | 396.2 | 66.7 | 33.3 | 11.1 |     |      |      |      |

| Productive parameters during Challenge *P. salmortis* (70d) |||||||||||
|---|---|---|---|---|---|---|---|---|---|---|
| D | Tk | gms$_0$ | n$_0$ | g$_{70}$ | ♰ | S | Δgms | FCR | SGR % | TGC | SFR % |
| C | 18 | 317.7 | 30.0 | 375.1 | 33.3 | 66.7 | 18.1 | 5.65 | 0.19 | 0.33 | 1.05 |
|   |    | 355.1 | 30.0 | 377.7 | 60.0 | 40.0 | 6.4  |      |      |      |      |

Key:
D = Diet.
C = Control, N = N-1, 7 = Gold 71.
Tk = tank number.
gms$_0$ = average fish weight (grams) at time = 0.
n$_0$ = number of fish at t =0.
g$_{70}$ = average fish weight (grams) at time = 70.
♰ = Cumulative Mortality (in percent).
S = Cumulative survivorship (in percent).
n$_{14}$ = number of fish at t =14.
x = number of sampling.
Δgms = change in average fish weight (in percent).
FCR = Food Conversion Ratio at end.
For each tank, cohabitant data are on the top line, shedder data are on the bottom line.
* = The productive parameters of tank 13 were considered until day 48 of the study.

The data from Tank #13 are incomplete due to apparatus failure. Presenting the data set excluding the results of tank #13 is as follows:

| Productive parameters during Challenge *P. salmortis* (70d) Excluding the results of tank #13 |||||||||||
|---|---|---|---|---|---|---|---|---|---|---|
| D | Tk | gms$_0$ | n$_0$ | g$_{70}$ | ♰ | S | Δgms | FCR | SGR % | TGC | SFR % |
| C | 10 | 311.9 | 30.0 | 373.2 | 26.7 | 73.3 | 19.7 | 7.40 | 0.19 | 0.30 | 1.39 |
|   |    | 344.4 | 30.0 | 357.5 | 66.7 | 33.3 | 3.8  |      |      |      |      |
| 7 | 11 | 301.8 | 30.0 | 382.8 | 10.0 | 90.0 | 26.8 | 5.05 | 0.27 | 0.48 | 1.35 |
|   |    | 354.7 | 30.0 | 390.1 | 76.7 | 23.3 | 10.0 |      |      |      |      |
| N | 12 | 306.6 | 30.0 | 386.9 | 10.0 | 90.0 | 26.2 | 4.85 | 0.26 | 0.47 | 1.24 |
|   |    | 345.6 | 30.0 | 373.5 | 63.3 | 36.7 | 8.1  |      |      |      |      |
| N | 14 | 308.3 | 30.0 | 390.8 | 26.7 | 73.3 | 26.8 | 5.40 | 0.28 | 0.48 | 1.49 |
|   |    | 352.5 | 30.0 | 393.5 | 86.7 | 13.3 | 11.6 |      |      |      |      |
| C | 15 | 308.2 | 30.0 | 341.2 | 30.0 | 70.0 | 10.7 | 7.45 | 0.14 | 0.20 | 1.05 |
|   |    | 344.8 | 30.0 | 378.7 | 63.3 | 36.7 | 9.8  |      |      |      |      |
| N | 16 | 312.1 | 30.0 | 369.0 | 10.0 | 90.0 | 18.2 | 5.85 | 0.23 | 0.34 | 1.37 |
|   |    | 361.7 | 30.0 | 422.9 | 66.7 | 33.3 | 16.9 |      |      |      |      |
| 7 | 17 | 313.8 | 30.0 | 390.5 | 20.0 | 80.0 | 24.4 | 4.45 | 0.26 | 0.44 | 1.14 |
|   |    | 356.5 | 30.0 | 396.2 | 66.7 | 33.3 | 11.1 |      |      |      |      |
| C | 18 | 317.7 | 30.0 | 375.1 | 33.3 | 66.7 | 18.1 | 5.78 | 0.19 | 0.33 | 1.07 |
|   |    | 355.1 | 30.0 | 377.7 | 60.0 | 40.0 | 6.4  |      |      |      |      |

Key:
D = Diet.
C = Control, N = N-1, 7 = Gold 71.
Tk = tank number.
gms$_0$ = average fish weight (grams) at time = 0.
n$_0$ = number of fish at t =0.
g$_{70}$ = average fish weight (grams) at time = 70.
♰ = Cumulative Mortality (in percent).
S = Cumulative survivorship (in percent).
n$_{14}$ = number of fish at t =14.
x = number of sampling.
Δgms = change in average fish weight (in percent).
FCR = Food Conversion Ratio at end.
For each tank, cohabitant data are on the top line, shedder data are on the bottom line.

In general, these parameters are not evaluated during the challenges with *P. salmonis*, since there are several factors that are detrimental to a good diet, for example the high density that is handled in these studies and the daily mortality that generates additional stress on the surviving fish and decreasing their appetite.

qPCR DNA Analysis:

Twenty seven (27) samples of head kidney and liver fixed in RNA were sent for analysis. These samples corresponded to 18 cohab fish samples (12 mortalities and 6 survivors) and 9 shedder fish (6 mortalities and 3 survivors). Where the liver of each sample was analyzed, obtaining value of Ct (Threshold Cycle) and the quantification of bacteria mg/tissue (theoretical value) per sample.

| Quantification of *Piscirickettsia salmortis* by qPCR ||||||
|---|---|---|---|---|---|
| Day | Hlth | Ct | Quantification | No. Tank | Shedder or Cohab | Diet |
| 16 | De-ceased | ~34 | 2.184 (**) | 19 11 | Shedder | Gold 71 |
| 16 | ceased | ~20 | 36.924.686 | 21 14 | Shedder | N-1 |

-continued

Quantification of *Piscirickettsia salmortis* by qPCR

| Day | Hlth | Ct | Quantification | No. | Tank | Shedder or Cohab | Diet |
|---|---|---|---|---|---|---|---|
| 16 | | ~18 | 330.127.315 (*) | 28 | 18 | Shedder | Control |
| 32 | | ~22 | 13.872.549 | 152 | 11 | Cohab | Gold 71 |
| 32 | | 0 | | 154 | 18 | Cohab | Control |
| 36 | | ~37 | 348 *(*) | 161 | 14 | Cohab | N-1 |
| 43 | | 0 | | 170 | 15 | Cohab | Control |
| 44 | | ~32 | 10.629(**) | 175 | 18 | Cohab | Control |
| 46 | | ~17 | 437.435.897 (*) | 180 | 17 | Shedder | Gold 71 |
| 46 | | 0 | | 181 | 17 | Cohab | Gold 71 |
| 47 | | ~20 | 70.810.811 | 183 | 15 | Shedder | Control |
| 48 | | ~20 | 32.956.403 | 189 | 16 | Shedder | N-1 |
| 50 | | ~20 | 77.054.545 | 195 | 11 | Cohab | Gold 71 |
| 52 | | ~18 | 313.663.133 (*) | 200 | 12 | Cohab | N-1 |
| 52 | | ~19 | 92.815.013 | 202 | 18 | Cohab | Control |
| 61 | | ~20 | 92.278.107 | 230 | 14 | Cohab | N-1 |
| 61 | | 0 | | 231 | 17 | Cohab | Gold 71 |
| 62 | | 0 | | 232 | 18 | Cohab | Control |
| 70 | Sur- | ~23 | 10.545.673 | 242 | 10 | Cohab | Control |
| 70 | vivor | ~28 | 455.154 | 250 | 10 | Shedder | Control |
| 70 | | 0 | | 275 | 11 | Cohab | Gold 71 |
| 70 | | ~22 | 15.149.233 | 282 | 11 | Shedder | Gold 71 |
| 70 | | ~23 | 4.391.691 | 312 | 12 | Cohab | N-1 |
| 70 | | ~36 | 471 (**) | 316 | 12 | Shedder | N-1 |
| 70 | | 0 | | 409 | 16 | Cohab | N-1 |
| 70 | | ~26 | 1.438.701 | 444 | 17 | Cohab | Gold 71 |
| 70 | | 0 | | 475 | 18 | Cohab | Control |

The 9 shedder fish analyzed showed 100% positivity, both in mortalities and in the surviving fish evaluated. In the cohab group, 8 samples without Ct were recorded, of which 5 corresponded to mortalities and 3 to surviving fish.

Average quantification of *Piscirickettsia salmonis* by qPCR by diet

| | Control | | | Gold 71 | | | N-1 | | |
|---|---|---|---|---|---|---|---|---|---|
| Gp | Average | Min. | Max | Average | Min. | Max | Average | Min. | Max |
| Co | 34457105 | 10629 | 92815013 | 30788598.3 | 1438701 | 77054545 | 102583319.8 | 348 | 313663133 |
| ☥ | 46412821 | 10629 | 92815013 | 45463547 | 13872549 | 77054545 | 135313862.7 | 348 | 313663133 |
| S | 10545673 | 10545673 | 10545673 | 1438701 | 1438701 | 1438701 | 4391691 | 4391691 | 4391691 |
| Sh | 133797760 | 455154 | 330127315 | 150862438 | 2184 | 437435897 | 23293853.3 | 471 | 36924686 |
| ☥ | 200469063 | 70810811 | 330127315 | 218719040.5 | 2184 | 437435897 | 34940544.5 | 32956403 | 36924686 |
| S | 455154 | 455154 | 455154 | 15149233 | 15149233 | 15149233 | 471 | 471 | 471 |
| TT | 84127433 | 10629 | 330127315 | 90825518 | 2184 | 437435897 | 68602120 | 348 | 313663133 |

Key:
Gp = Group,
Co = cohabitator,
Sh = inoculated shedder,
☥ = deceased,
S = survivor,
TT = Grand Totals.

The bacterial quantification showed a relationship between the Ct and the amount of mg/tissue bacteria recorded, at lower Ct greater amount of bacteria. It was also observed that the amount of bacteria mg/tissue varied between groups and diets, being the diet Gold 71, the one that presented the highest amount of bacteria per mg/tissue in the shedder group, followed by the Control diet, being the N1 diet which obtained the lowest values (see tables). While in the cohabiting group, diet N1 obtained the highest quantification values, tripling the values recorded in the cohabiting group of the control and Gold 71 diets (see table).

Conclusions

After 70 days of SRS challenge under experimental conditions, it was observed that diets N1 and Gold 71 reduce the risk of mortality in similar percentages (60% and 56%). So it can be determined that both diets have similar efficacy levels, not registering significant differences between them. However, the delay in the start of the mortality in the diet N1 cohabitant group may suggest a bigger effectiveness of this diet against the disease.

Example 8

The objective of this study is to compare the efficacy against *Piscirickettsia salmonis* of N1 to Futerpenol™ brand aquaculture feed additive in an Atlantic salmon cohabitation challenge model.

Materials & Methods:

Experimental Design

Species: Atlantic salmon (*Salmo salar*), number of fish=540, having an average initial weight of 150 g (CV<15%) are obtained from the fish farm Caliboro, Trusal S.A, located in Los Angeles, Chile. The fish are sanitary analyzed to confirm the absence of pre-existing pathogens such as Infectious Pancreatic Necrosis Virus (IPNV), *Renibacterium salmoninarum* (BKD), Infectious Salmon Anemia Virus (ISA) and Piscine reovirus (PRV).

Feed is an industry-standard aquaculture feed. N1 is, as in the previous Example, a feed additive comprising 96% (w/w) dried seaweed powder (the dried seaweed contains a mixture of various types of seaweed but does not contain *Macrocystis pyrifera* seaweed) and 2% (w/w) andrographolides. Futerpenol™ is a commercially-available feed additive purporting to have the composition as described in Paula MIRANDA-CAMPOS et al., Veterinary Composition Of Marine Algae And *Andrographis* Sp. Extracts, Which Can Be Used To Treat Infections In Fish, Patent Cooperation Treaty publication No. WO 2016/161534. It is labeled for use at 1 kg Futerpenol™ per ton of industry-standard aquaculture feed.

As in the previous Example, the trial begins with an acclimatization period on day −20. Eighteen aquaculture tanks, each of a 350 L capacity, are used. Each is configured to house 35 Atlantic salmon. As in the previous Example, we divide the tanks into two groups of nine tanks, one for the "shedder" (inoculated) group and the other for the non-infected group. Starting weights of the fish average ~160 g/fish for both populations. The fish are kept in fiberglass ponds in a 70/30 water reuse system during the acclimatization and experimental period and a 90/10 water reuse system during the challenge with *P. salmonis*. The ponds have a water flow that allow a replacement of 1.2 spare parts hour prior to the challenge and 0.8 L/h during the challenge with *P. salmonis*, supplied with seawater directly from the sea at room temperature and salinity and during the challenge the water are maintained at 15° C. by a natural gas boiler. In addition, incoming seawater is filtered at 60 □m and disinfected with a UV system. The ponds are illuminated with fluorescent lights located on the roof of the building, with a photoperiod of 24 hours light.

At day=0, a measurement of weight and length of each of the fish is made. At day=1, we begin delivery of the experimental diets and three experimental groups were set up in triplicate: industry-standard feed as the control diet, industry-standard feed supplemented with Futerpenol™ at the labeled amount and industry-standard feed supplemented with N-1 as discussed above. Acclimatization lasts 14 days.

On day=15, the fish are transferred to a unit, to begin the challenge by cohabitation with "Shedder" (or "Trojan") fish (i.e., fish that have been inoculated with *P. salmonis*). Prior to the transfer, basal samples of 5 fish per pond are taken. Two hundred seventy (270) healthy fish are inoculated with *P. salmonis*. The inoculation is performed intra-peritoneally (IP) by injecting 0.2 mL (approximately $8.5 \times 10^3$ bacteria) of *P. salmonis* strain EM90 from the Fraunhofer laboratory, with an inoculum titer of ~100 DICT50/mL, obtaining a theoretical bacterial quantification of $10^5$ bacteria/mL ($4.3 \times 10^3$ bacteria/mL). The inoculation procedure is as in the previous Example. The "Shedder" (inoculated) fish are then distributed in nine 350 L ponds, 30 Shedders/pond. In addition, an equal number of healthy (non-inoculated) fish are transferred into each pond to co-habit with the Shedders. Each pond therefore includes 30 Shedder fish and 30 non-inoculated or "cohabiting" fish. The fish are so maintained for 70 days. During this period different ponds are fed different test diets. Throughout the study the food is supplied manually at apparent satiety at least four times a day, trying to recover at least 15% of the food not consumed, to ensure satiety. Unconsumed food is collected twice a day by flushing method. Then 30 pellets are counted for each pond collected and weighed, with this the amount of pellets not consumed per pond can be estimated. The amount of food not consumed is calculated by multiplying the amount of pellets not consumed by the average weight of 1 dry pellet. Fish are weighed and measured daily. The mortalities generated during the trial are identified by pond and by whether the individual has been inoculated. On the 70th day, the entire surviving population is sacrificed and we record each individual fish's weight, length, degree of internal necropsy, individual photography and organ sampling.

During the main challenge, samples of the previous kidney and liver are taken at the entire mortality of cohabiting fish and 1 Shedder from each pond, for confirmation of *P. salmonis*. The same samples are taken at day 70 (final sampling), using 10 cohabitants and 1 surviving Shedder from each pond. The samples are stored at −20° C. We analyze organ tissue samples (including Shedders and co-inhabitants, and including mortalities and survivors) by qPCR, by means of DNA detection, as in the previous Example.

In addition, necropsy is performed on each fish, assessing the gastrointestinal content at all mortality, defining the degree of this content as; empty (no stool or only in the distal intestine), full (food in the middle and posterior intestine), half of the distal intestine (food in 50% of the distal intestine) or last stretch of the distal intestine (food in 25% of the distal intestine). FIG. 15 indicates the different gastrointestinal regions.

Liver, anterior kidney and intestine samples are taken before 10% of mortality, 10 cohabitants and 1 surviving Shedder per pond and are fixed in formalin for histoscore analysis. Also, the following information of all the fish is recorded: Pond of origin, Group, Weight, Length, and an individual photograph of mortality and 11 survivors per pond. At the end of the study all surviving fish are euthanized with an anesthetic overdose. The elimination of all euthanized fish is recorded during and at the end of the study. Fundación Chile ensures that the elimination is carried out in accordance with all relevant guidelines, codes of good practice, procedures and legal regulations.

To evaluate the continuity of the study when evaluating two replicates of the Futerpenol™ diet, compared to the 3 replicas of the N1 and Control diet, after the 48th post-challenge week, cumulative mortality is evaluated, to verify if there are significant differences.

Calculations and Parameters to Evaluate:

The fish population is weighed and measured to assess growth performance parameters, such as weight gain percentage (WI), feed conversion rate (FCR), specific growth rate (SGR), rate Specific feed (SFR) and condition factor (K). The cumulative mortality curves are analyzed using the Kaplan-Meier function and statistically evaluated with the Log Rank test, with the GraphPad™ Prism V6 statistical program. The effectiveness of the diets is determined by the Relative Survival Percentage Survival (RPS) method (Ellis, 1988). We predict results similar to that shown in the following Table: Survival Summary. For each diet in isolation, we compare the results of the different tanks to measure the variance of results for each diet.

TABLE

Survival Summary
Comparative Mortality
Inoculated (I) vs Non-Inoculated (C)

| Diet | | | Mortality | | Survival | | Odds Ratios C:I | D:Ctl |
|---|---|---|---|---|---|---|---|---|
| Control | P10 | C | 8 | 27% | 22 | 73% | | |
| | | I | 22 | 73% | 8 | 27% | | |
| | P15 | C | 10 | 33% | 20 | 67% | | |
| | | I | 21 | 70% | 9 | 30% | | |
| | P18 | C | 15 | 50% | 15 | 50% | | |
| | | I | 22 | 73% | 8 | 27% | | |
| | Total | C | 33 | 37% | 57 | 63% | 2.28 | 1.00 |
| | | I | 65 | 72% | 25 | 28% | | 1.00 |
| N-1 | P12 | C | 3 | 10% | 27 | 90% | | |
| | | I | 19 | 63% | 11 | 37% | | |
| | P14 | C | 5 | 17% | 25 | 83% | | |
| | | I | 16 | 53% | 14 | 47% | | |
| | P16 | C | 1 | 3% | 29 | 97% | | |
| | | I | 13 | 43% | 17 | 57% | | |
| | Total | C | 9 | 10% | 81 | 90% | 1.93 | 1.42 |
| | | I | 48 | 53% | 42 | 47% | | 1.68 |
| Futerpenol™ | P11 | C | 9 | 30% | 21 | 70% | | |
| | | I | 24 | 80% | 6 | 20% | | |
| | P13 | C | 10 | 33% | 20 | 67% | | |
| | | I | 21 | 70% | 9 | 30% | | |

TABLE-continued

Survival Summary
Comparative Mortality
Inoculated (I) vs Non-Inoculated (C)

| Diet | | | Mortality | | Survival | | Odds Ratios | |
|---|---|---|---|---|---|---|---|---|
| | | | | | | | C:I | D:Ctl |
| | P17 | C | 12 | 40% | 18 | 60% | | |
| | | I | 18 | 60% | 12 | 40% | | |
| | Total | C | 31 | 34% | 59 | 66% | 2.19 | 1.04 |
| | | I | 63 | 70% | 27 | 30% | | 1.08 |

Notes:
Each tank starts with 30 Inoculated and 30 Cohabitant
I, C = Inoculation status.
I = Inoculated,
C = Non-inoculated cohabitant
P = pond number
C:I = Survival Odds Ratio, Non-Inoculated vs Inoculated
D:Ctl = Survival Odds Ratio, (Experimental) Diet vs Control Diet An Odds Ratio is the ratio of the odds of an event occurring under two different conditions. For example, one can compare non-inoculated to inoculated fish, to determine how much more likely non-inoculated fish are to survive viz inoculated fish. A survival ratio of ~2 means that non-inoculated (cohabitant) fish are, on average, twice as likely to survive as are inoculated (shedder or "Trojan") fish. One can also use odds ratios to compare the odds of survival between different diets. For example, one can compare survival of fish fed the control diet viz fish fed the N–1 supplemented or the Futerpenol™ supplemented diet. Odds ratios of ~1.5 means that fish fed the experimental diet are about 50% (i.e., 1.5 times) more likely to survive than are fish fed the control diet. In contrast, odds ratios of ~1.05 mean that fish fed on the experimental diet are only about five percent (i.e., 1.05 times) more likely to survive than are fish fed the control diet. While these differences intuitively may not appear large, in practice they are: an odds ratio of 1.5 demonstrates ten times the incremental benefit of an odds ratio of 1.05. For example, in a population of 100 fish, the difference in additional surviving fish is 5 fish vs 50 fish.

Cumulative Mortality:

The start of mortality in the shedder groups is one to two weeks after inoculation, and for the cohabitant groups the outbreak occurs roughly four to six weeks after combining with the inoculated fish. As observed in the previous Example 7, diet N1 slows the start of the outbreak most effectively, having the first detected infected cohabitants almost two weeks later than those in the control diet groups and a week after than in the Futerpenol™ groups.

On the control diet the inoculated (Shedder) group has a cumulative mortality of ~70%, and the non-inoculated (cohabitant) group has a cumulative mortality of ~35%, both roughly in line with the results previously observed with Example 7 above. Supplementation with N–1 also increases survival for both inoculated and cohabitants, increasing the likelihood of surviving by 68% and 42% respectively, both roughly in line with the results previously observed with Example 7 above. Supplementation with Futerpenol™ also increases survival (viz the control diet) for both inoculated and cohabitants, albeit the increase is slight, increasing the likelihood of surviving by only 8% and 4% respectively. Supplementation with N–1 thus provides roughly ten times the incremental benefit as does Futerpenol™.

At the end of the challenge was possible to see some level of protection in both evaluated diets, albeit N1 provides roughly ten times the incremental benefit as Futerpenol™.

Conclusions:

After 70 days of SRS challenge under experimental conditions, diets supplemented with N1 or with Futerpenol™ each reduce the risk of mortality, albeit supplementation with N1 produces approximately ten times the benefit of supplementation with Futerpenol™. Part of the superiority of N–1 may be due to the delay in the start of the mortality in the diet N1 group.

SUMMARY

Given our disclosure, the artisan can readily make modifications to it. For example, while our testing used a mixture of dried seaweeds that does not include *Macrocystis pyrifera* seaweed, the artisan can vary the kind and ratio of the various seaweed species to suit the desired diet of the cultured sea creatures. We thus intend the legal coverage of our patent to be defined not by the specific examples and experiments we disclose here, but by our appended legal claims and their permissible equivalents.

In our legal claims, for economy of language we use the term "fish" to encompass not only gill-bearing, craniate aquatic animals (e.g., salmon, trout, tuna etc.), but also aquatic crustaceans (e.g., shrimp, prawn, krill, lobster, crabs etc.). We use the term "seaweed" to encompass kelp, a type of seaweed.

We thus intend our patent to cover, for example:

1. A marine feed additive comprising from 2% to 7% (w/w) andrographolide and from 70% to 98% (w/w) dried whole seaweed comprising insoluble plant material.

2. The marine feed additive of the above paragraph number 1, where the dried seaweed is powdered.

3 The marine feed additive of the above paragraph number 2, where the dried seaweed does not contain *Macrocystis pyrifera* seaweed.

4. The marine feed additive of the above paragraph number 1, comprising from 2% to 3% (w/w) andrographolide and at least 95% (w/w) dried whole seaweed comprising insoluble plant material.

5. The marine feed additive of the above paragraph number 1, further comprising a compound selected from the group consisting of: grape seed extract, shisandra berry extract, and curcuminoids.

6. The marine feed additive of the above paragraph number 5, comprising 71% (w/w) dried whole seaweed comprising insoluble plant material, 10% (w/w) grape seed extract, 10% (w/w) shisandra berry extract, 4.75% (w/w) curcuminoids and 2% (w/w) andrographolides.

7. The marine feed additive of the above paragraph number 1, further comprising marine feed, the marine feed additive and the marine feed physically combined to form a marine feed mixture, the marine feed additive and the marine feed present in a weight:weight ratio of about 0.5 parts marine feed additive of the above paragraph number 1 per 1000 parts marine feed.

8. The marine feed additive of the above paragraph number 1, further comprising marine feed, the marine feed additive and the marine feed physically combined to form a marine feed mixture, the marine feed additive of the above paragraph number 1 present in a ratio sufficient that fish fed on said marine feed mixture grow faster than do fish fed on said marine feed alone.

9. The marine feed additive of the above paragraph number 1, further comprising marine feed, the marine feed additive and the marine feed physically combined to form a marine feed mixture, the marine feed additive of the above paragraph number 1 present in a ratio sufficient that fish fed on said marine feed mixture convert a higher percentage of said marine feed to body mass than do fish fed on said marine feed alone.

10. The marine feed additive of the above paragraph number 1, further comprising marine feed, the marine feed additive and the marine feed physically combined to form a marine feed mixture, the marine feed additive of the above paragraph number 1 present in a ratio sufficient that fish fed on said marine feed mixture are less susceptible to marine pathogen infection than are fish fed on said marine feed alone.

11. A method of increasing the growth rate of fish grown in aquaculture, the method comprising administering to fish grown in aquaculture the marine feed additive of the above paragraph number 1.

12. A method of increasing the conversion of marine feed to body mass of fish grown in aquaculture, the method comprising administering to fish grown in aquaculture the marine feed additive of the above paragraph number 1.

13. A method of increasing the resistance of fish grown in aquaculture to marine pathogen infection, the method comprising administering to fish grown in aquaculture the marine feed additive of the above paragraph number 1.

The invention claimed is:

1. A marine feed additive comprising from 2% to 7% (w/w) andrographolide and from 70% to 98% (w/w) dried whole seaweed comprising insoluble plant material.

2. The marine feed additive of claim 1, where the dried seaweed is powdered.

3. The marine feed additive of claim 2, where the dried seaweed does not contain *Macrocystis pyrifera* seaweed.

4. The marine feed additive of claim 1, comprising from 2% to 3% (w/w) andrographolide and at least 93% (w/w) dried whole seaweed comprising insoluble plant material.

5. The marine feed additive of claim 1, further comprising a compound selected from the group consisting of: grape seed extract, shisandra berry extract, and curcuminoids.

6. The marine feed additive of claim 5, comprising 71% (w/w) dried whole seaweed comprising insoluble plant material, 10% (w/w) grape seed extract, 10% (w/w) shisandra berry extract, 4.75% (w/w) curcuminoids and 2% (w/w) andrographolides.

7. The marine feed additive of claim 1, further comprising marine feed, the marine feed additive and the marine feed physically combined to form a marine feed mixture, the marine feed additive and the marine feed present in a weight:weight ratio of about 0.5 parts marine feed additive per 1000 parts marine feed.

8. The marine feed additive of claim 1, further comprising marine feed, the marine feed additive and the marine feed physically combined to form a marine feed mixture, the marine feed additive present in a ratio sufficient that fish fed on said marine feed mixture grow faster than do fish fed on said marine feed alone.

9. The marine feed additive of claim 1, further comprising marine feed, the marine feed additive and the marine feed physically combined to form a marine feed mixture, the marine feed additive present in a ratio sufficient that fish fed on said marine feed mixture convert a higher percentage of said marine feed to body mass than do fish fed on said marine feed alone.

10. The marine feed additive of claim 1, further comprising marine feed, the marine feed additive and the marine feed physically combined to form a marine feed mixture, the marine feed additive present in a ratio sufficient that fish fed on said marine feed mixture are less susceptible to marine pathogen infection than are fish fed on said marine feed alone.

11. The marine feed mixture of claim 10, wherein the marine feed additive is present in an amount sufficient that salmon fed on said marine feed mixture are less susceptible to *Piscirickettsia salmonis* infection than are salmon fed on said marine feed alone.

12. The marine feed mixture of claim 10, wherein the marine feed additive is present in an amount sufficient that shrimp fed on said marine feed mixture are less susceptible to white-spot syndrome virus infection than are shrimp fed on said marine feed alone.

13. A method of decreasing the risk of infection of fish grown in aquaculture, the method comprising administering to fish grown in aquaculture the marine feed additive of claim 1.

14. The method of claim 13, wherein the marine feed additive is present in an amount sufficient that salmon fed on said marine feed additive are less susceptible to *Piscirickettsia salmonis* infection than are salmon not fed on said marine feed additive.

15. The method of claim 13, wherein the marine feed additive is present in an amount sufficient that shrimp fed on said marine feed additive are less susceptible to white-spot syndrome virus infection than are shrimp not fed on said marine feed additive.

16. A method of decreasing the risk of infection of fish grown in aquaculture, the method comprising administering to fish grown in aquaculture the marine feed mixture of claim 10.

17. The method of claim 16, wherein the marine feed additive is present in an amount sufficient that salmon fed on said marine feed mixture are less susceptible to *Piscirickettsia salmonis* infection than are salmon not fed on said marine feed mixture.

18. The method of claim 16, wherein the marine feed additive is present in an amount sufficient that shrimp fed on said marine feed mixture are less susceptible to white-spot syndrome virus infection than are shrimp not fed on said marine feed mixture.

19. A method of increasing the growth rate of fish grown in aquaculture, the method comprising administering to fish grown in aquaculture the marine feed additive of claim 1.

20. A method of increasing the conversion of marine feed to body mass of fish grown in aquaculture, the method comprising administering to fish grown in aquaculture the marine feed additive of claim 1.

21. A method of increasing the resistance of fish grown in aquaculture to marine pathogen infection, the method comprising administering to fish grown in aquaculture the marine feed additive of claim 1.

* * * * *